(12) United States Patent
Fuchss et al.

(10) Patent No.: US 12,344,604 B2
(45) Date of Patent: Jul. 1, 2025

(54) IMIDAZOLONYLQUINOLINE COMPOUNDS AND THERAPEUTIC USES THEREOF

(71) Applicant: Merck Patent GmbH, Darmstadt (DE)

(72) Inventors: Thomas Fuchss, Bensheim-Auerbach (DE); Axel Becker, Seeheim-Jugenheim (DE); Holger Kubas, Bad Homburg (DE); Ulrich Graedler, Weinheim (DE)

(73) Assignee: Merck Patent GmbH, Darmstadt (DE)

( * ) Notice: Subject to any disclaimer, the term of this patent is extended or adjusted under 35 U.S.C. 154(b) by 806 days.

(21) Appl. No.: 17/442,703

(22) PCT Filed: Mar. 25, 2020

(86) PCT No.: PCT/EP2020/058425
§ 371 (c)(1),
(2) Date: Sep. 24, 2021

(87) PCT Pub. No.: WO2020/193660
PCT Pub. Date: Oct. 1, 2020

(65) Prior Publication Data
US 2022/0144828 A1    May 12, 2022

(30) Foreign Application Priority Data
Mar. 27, 2019    (EP) ..................................... 19165664

(51) Int. Cl.
*C07D 471/04*    (2006.01)
*A61P 35/00*    (2006.01)

(52) U.S. Cl.
CPC ............ *C07D 471/04* (2013.01); *A61P 35/00* (2018.01); *C07B 2200/05* (2013.01)

(58) Field of Classification Search
CPC .. A61P 35/00; C07B 2200/05; C07B 2200/13
See application file for complete search history.

(56) References Cited

U.S. PATENT DOCUMENTS 7,612,083 B2    11/2009    Griesgraber

FOREIGN PATENT DOCUMENTS

| CA | 2981364 A1 | 10/2016 | |
|---|---|---|---|
| CA | 2981365 A1 | 10/2016 | |
| CN | 108752336 A | * 11/2018 | ................ A61P 1/02 |
| RU | 2 308 456 | 10/2007 | |
| WO | 2016/155884 | 5/2020 | |

OTHER PUBLICATIONS

Fuchss. WO 2016/155884. English Translation. (Year: 2016).*
Guerra Garcia et al. Seminars in Radiation Oncology. 2022, 32(1), pp. 3-14. (Year: 2022).*
Ueno et al. Int. J. Mol. Sci. 2022, 23(1), 523. (Year: 2022).*
Zhu, X. CN-108752336-A. English Translation. (Year: 2018).*

Smyth et al., "A twist of nature —the significance of atropisomers in biological systems", Nat. Prod. Rep., vol. 32, Aug. 18, 2015, pp. 1562-1583.
International Search Report in PCT/EP2020/058425 dated May 12, 2020.
Written Opinion in PCT/EP2020/058425 dated May 12, 2020.
Davis E. Smith, et al., "Exploiting Atropisomerism to Increase the Target Selectivity of Kinase Inhibitors," Angewandte Chemie, International Edition, vol. 54, No. 40, Sep. 28, 2015, pp. 11754-11759.
Kenyu Yoshida, et al., "Synthesis, Resolution, and Biological Evaluation of Atropisomeric (a R )- and (a S)-16-Methyllamellarins N: Unique Effects of the Axial Chirality on the Selectivity of Protein Kinases Inhibition," *Journal of Medicinal Chemistry*, vol. 56, No. 18, Jan. 1, 2013, pp. 7289-7301.
Monika Gupta et al., "Deuteration as a Tool for Optimization of Metabolic Stability and Toxicity of Drugs", Glob J Pharmaceu Sci., vol. 1, Issue 4, Mar. 2017, pp. 1-11.
Byrn et al. " Pharmaceutical Solids: A Strategic Approach to Regulatory Considerations", Pharmaceutical Research, vol. 12, No. 7, Jul. 1995, pp. 945-954.

(Continued)

*Primary Examiner* — Eric Olson
*Assistant Examiner* — Samuel L Galster
(74) *Attorney, Agent, or Firm* — Grüneberg and Myers PLLC

(57) ABSTRACT

Atropisomers, solid forms, salt forms, and deuterated derivatives of the ATM inhibitor 8-(1,3-Dimethyl-1H-pyrazol-4-yl)-1-(3-fluoro-5-methoxypyridin-4-yl)-7-methoxy-3-methyl-1,3-dihydroimidazo[4,5-c]quinolin-2-one as well as compositions thereof are provided. The stable atropisomers do not interconvert and are represented by the following formulae.

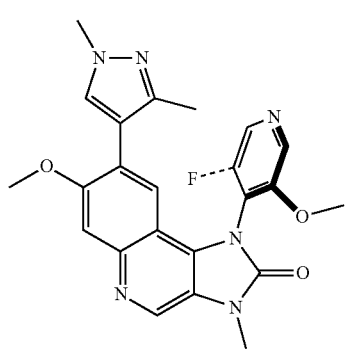

Compound 1

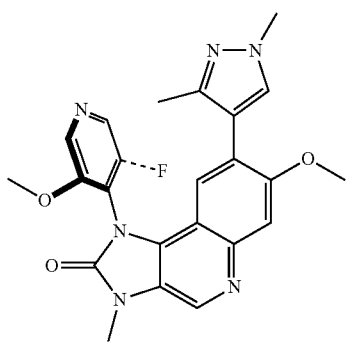

Compound 2

8 Claims, 38 Drawing Sheets

(56) References Cited

OTHER PUBLICATIONS

Lian Yu, "Amorphous pharmaceutical solids: preparation, characterization and stabilization", Advanced Drug Delivery Reviews, vol. 48, May 16, 2001, pp. 27-42.
Mino R. Caira, "Crystalline Polymorphism of Organic Compounds", Topics in Current Chemistry, XP-001156954, vol. 198, Jan. 1, 1999, pp. 163-208.
Office Action issued in Canadian Patent Application No. 3,134,874 on Jan. 29, 2025, 4 pages.

* cited by examiner

Annotated ¹H NMR Spectrum of Compound 1 (annotated numbers denote the assignments).

Annotated $^{13}C$ NMR Spectrum of Compound 1
(annotated numbers denote the assignments).

Annotated ¹⁹F NMR Spectrum of Compound 1 (annotated numbers denote the assignments).

UV-Vis-Spectrum of Compound 1 in Methanol.

HPLC chromatogram of Compounds 1 and 2.

Flowchart of the Preparation of Compounds 1 and 2.

A: Crystal Structure of Compound-1-Dibenzoyl-D-tartrate.

The absolute structure has been determined on the basis of the (2S,3S)-Dibenzoyl-D-tartrate.

B: XRPD of Compound-1-Dibenzoyl-D-tartrate.

Crystal Structure of Compound-2-Dibenzoyl-L-tartrate.

The absolute structure has been determined on the basis of the (2$R$,3$R$)-Dibenzoyl-L-tartrate.

Non-sink Dissolution Behavior in FaSSIF of Compound 1 and specific salts thereof.

Parent batch = Compound 1

XRPD of Solid Form of Compound 1 Fumarate

XRPD of Solid Form of Compound 1 Napsylate

XRPD of Solid Form of Compound 1 Edisylate.

XRPD of Solid Form A2 of Compound 1.

XRPD of Solid Form A1 of Compound 1.

XRPD of Solid Form A3 of Compound 1.

XRPD of Solid Form NF9 of Compound 1.

XRPD of Solid Form H1 of Compound 1 Hydrate.

XRPD of Solid Form H2 of Compound 1 Hydrate.

XRPD of Solid Form NF19 of Compound 1.

Strong Tumor Growth Inhibition by Irradiation and Concomitant Oral Compound 1 (6 x 5 days, 2 Gy; FaDu SCCHN Tumor Model)

*In vivo* evaluation of anti-tumor activity of Compound 1 and comparative ATM inhibitor in combination with olaparib, in HBCx-10 patient-derived triple-negative breast cancer xenograft model

- Vehicle
- Olaparib 50mg/kg 1qd x 49
- ATMix (3d+/4d-) x 7
- Olaparib + AMTix (3d+/4d-) x 7
- Olaparib + Compound 1 100 mg/kg (3d+/4d-) x 7

DSC heating curve of Form A2 of Compound 1

TGA heating curve of Form A2 of Compound 1

DVS water uptake isotherm (25 °C) of Form A2 of Compound 1

DSC heating curve of Form A1 of Compound 1

TGA heating curve of Form A1 of Compound 1

DVS water uptake isotherm (25 °C) of Form A3 of Compound 1

DSC heating curve of Form H2 of Compound 1

TGA heating curve form H2 of Compound 1

DVS water uptake isotherm (25°C) of Form H2 of Compound 1 (hydrate).

DSC heating curve of Compound 1 Fumarate (Form "NF6")

TGA heating curve of Compound 1 Fumarate (Form "NF6")

DVS water uptake isotherm (25 °C) of Compound 1 Fumarate (Form "NF6")

DSC heating curve of Compound 1 Napsylate (NF7)

TGA heating curve of Compound 1 Napsylate (NF7)

DVS water uptake isotherm (25 °C) of Compound 1 Napsylate (NF7)

DSC heating curve of Compound 1 Edisylate (NF8)

TGA heating curve of Compound 1 Edisylate (NF8)

DVS water uptake isotherm (25 °C) of Compound 1 Edisylate (NF8)

XRPD of a methanolate of Compound 1 in solid form S1

XRPD of a hydrate/methanolate of Compound 1 in solid form S2

XRPD of a THF solvate of Compound 1 in solid form S3

XRPD of a dioxane solvate of Compound 1 in solid form NF11

XRPD of a chloroform solvate of Compound 1 in solid form NF15

XRPD of an acetic acid solvate of Compound 1 in solid form NF16

XRPD of an acetic acid solvate of Compound 1 in solid form NF18

XRPD of a 1,4-dioxane solvate of Compound 1 in solid form NF29

XRPD of a dichloromethane solvate of Compound 1 in solid NF32

XRPD of a NMP (N-Methyl-2-pyrrolidon) solvate of Compound 1 in solid NF33

XRPD of an acetonitrile solvate of Compound 1 in solid form NF35

XRPD of a 1,4-dioxane solvate of Compound 1 in solid form NF36

XRPD of a dimethylacetamide solvate of Compound 1 in solid form NF37

IMIDAZOLONYLQUINOLINE COMPOUNDS AND THERAPEUTIC USES THEREOF

CROSS-REFERENCE TO RELATED APPLICATIONS

This application is a National Stage entry under § 371 of International Application No. PCT/EP2020/058425, filed on Mar. 25, 2020, and which claims the benefit of European Application No. 19165664.4, filed on Mar. 27, 2019. The content of each of these applications is hereby incorporated by reference in its entirety.

BACKGROUND OF THE INVENTION

Field of the Invention

The present invention provides atropisomers and deuterated derivatives of the ATM inhibitor 8-(1,3-Dimethyl-1H-pyrazol-4-yl)-1-(3-fluoro-5-methoxypyridin-4-yl)-7-methoxy-3-methyl-1,3-dihydroimidazo[4,5-c]quinolin-2-one as well as pharmaceutically acceptable salts, and solid forms thereof. These compounds are useful in the inhibition, regulation and/or modulation of signal transduction by ATM kinase. The invention also provides compositions comprising said atropisomers, solid forms, pharmaceutically acceptable salts and deuterated derivatives of the present invention as well as methods of using these compositions in the treatment of various disorders that relate to ATM kinase, in particular cancer.

Description of Related Art

The serine/threonine protein kinase ATM (ataxia telangiectasia mutated kinase) belongs to the PIKK family of kinases with catalytic domains, which are homologous to the phospho-inositide-3 kinases (PI3 kinase, PI3K). These kinases are involved in a variety of key cellular functions, such as cell growth, cell proliferation, migration, differentiation, survival and cell adhesion. In particular, these kinases respond to DNA damage by activating cell cycle arrest and DNA repair programs (DDR: DNA damage response). ATM is a product of the ATM gene and plays a key role in the repair of damage to the DNA double strand (DSB: double strand breaks) by homologous recombination and non-homologous end-to-end joining (NHEJ). This type of double-strand damage is particularly cytotoxic.

One of the main features of tumors in humans is their genomic instability, with the specific defects of the DNA repair mechanism not yet known in most cancers. This instability represents the therapeutic starting point for chemotherapy, which has been predominantly practiced for some time. In addition, there are a few syndromes in which the underlying genetic factor is a loss of function-associated mutation of a gene that modulates the response to DNA double-strand damage. This includes ataxia telangiectasia, which is caused by a defective ATM gene. A common feature of all these syndromes is that they cause extreme radiation sensitivity (Lavin & Shiloh (1997) Annu. Rev. Immunol. 15: 177; Rotman & Shiloh (1998) Hum. Mol. Genet. 7: 1555, the entirety of which is hereby incorporated herein by reference). ATM-deficient cells are accordingly sensitive to agents and other measures that cause damage to the DNA duplex, making ATM an attractive target for chemo- and radiation-sensitization in cancer treatment.

In summary, ATM (ataxia telangiectasia mutated kinase) is a key regulator of DNA double-strand break repair, which is induced by widely used radio- and chemotherapy. ATM relays a widespread signal to a multitude of downstream effectors including p53. Unrepaired double strand breaks lead to activation of checkpoint responses, cell cycle arrest and ultimately tumor cell death. Hence, ATM has become an attractive intervention point to inhibit repair of induced double strand breaks.

The compound Wortmannin was among those initially investigated in this context and showed a radiosensitisation that could be attributed inter alia to inhibition of ATM. However, it was not suitable for therapeutic uses due to in vivo toxicity. Starting from the chemical structure of the PI3K inhibitor LY294002, KuDOS Pharmaceuticals identified the ATM inhibitor: KU-55933 (2-morpholino-6-(thianthren-1-yl)-4H-pyran-4-one). With this compound the sensitization to ionizing radiation and DNA double strand-damaging chemo-therapeutic agents was accomplished (Hickson, I., et al. (2004), Cancer Res 64, 9152-9159, the entirety of which is hereby incorporated herein by reference). However, KU-55933 was found to be unsuitable for in vivo use, presumably due to its high lipophilicity. KU-60019 (2-((2S,6R)-2,6-dimethylmorpholino)-N-(5-(6-morpholino-4-oxo-4H-pyran-2-yl)-9H-thioxanthen-2-yl)-acetamide) and KU-559403 (2-(4-methylpiperazin-1-yl)-N-[5-(6-morpholino-4-oxopyran-2-yl)thioxanthen-2-yl] acetamide) were subsequently developed, and KU-559403 was hailed promising enough to enter clinical trial for the treatment of advanced solid tumors.

There are further ATM inhibitors that support the above notion in that they are currently in clinical development, e.g. AZD0156, AZD1390 and M3541, including clinical studies involving their combination with radiotherapy.

While much progress has been made in the field of ATM inhibitors, there remains a need to provide a compound that has high inhibition of ATM kinase but also beneficial selectivity over other kinases, beneficial bioavailability and/or reduced off-target effects.

SUMMARY OF THE INVENTION

The provision of small molecules which effectively inhibit, regulate and/or modulate signal transduction by ATM kinase is desirable and one object of the present invention. It is furthermore desirable to provide ATM inhibitors that are selective, i.e. have no or significantly lower activity against other kinases. It is furthermore desirable to provide ATMi inhibitors that show beneficial properties with regard to known targets causing undesired side effects. One object therefore is to provide compounds that have reduced off-target effects and/or associated toxicities. Furthermore, it is an object of the present invention to provide an ATM inhibitor with good bioavailability. It is a further or alternative object of the present invention to provide an ATM inhibitor with advantageous solid form properties, such as favourably low hygroscopicity and/or other physical properties.

At least one object as outlined above and further objects is/are solved by atropisomers and deuterated derivatives of the ATM inhibitor 8-(1,3-dimethyl-1H-pyrazol-4-yl)-1-(3-fluoro-5-methoxypyridin-4-yl)-7-methoxy-3-methyl-1,3-dihydroimidazo[4,5-c]quinolin-2-one (Compound Y) as well as solid forms, pharmaceutically acceptable salts and compositions thereof.

One aspect of the invention provides two compounds, which are atropisomers of Compound Y, and represented by the formulae:

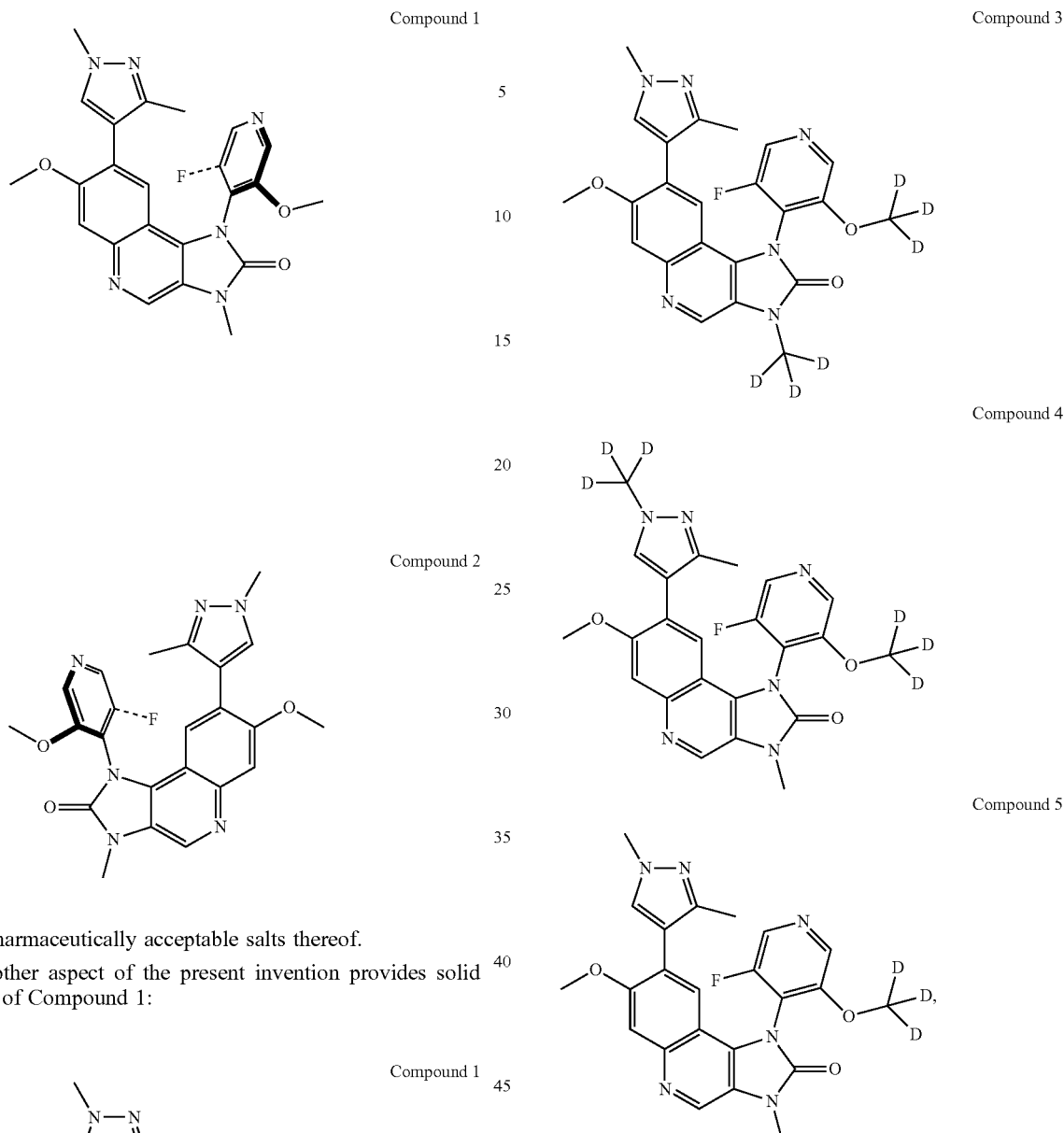

and pharmaceutically acceptable salts thereof.

Another aspect of the present invention provides solid forms of Compound 1:

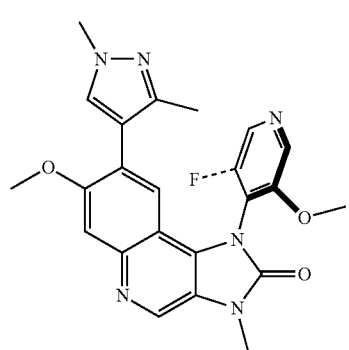

Compound 1

Another aspect relates to certain particularly advantageous pharmaceutically acceptable salts of Compound 1, in particular Compound 1 fumarate, Compound 1 edisylate and Compound 1 napsylate, which may also be collectively referred to as "Compounds 1-a" hereinafter.

Another aspect of the present invention provides deuterated compounds 3, 4, and 5, which are represented by the following formulae:

or atropisomers or pharmaceutically acceptable salts thereof.

DETAILED DESCRIPTION OF THE INVENTION

Figure 1:
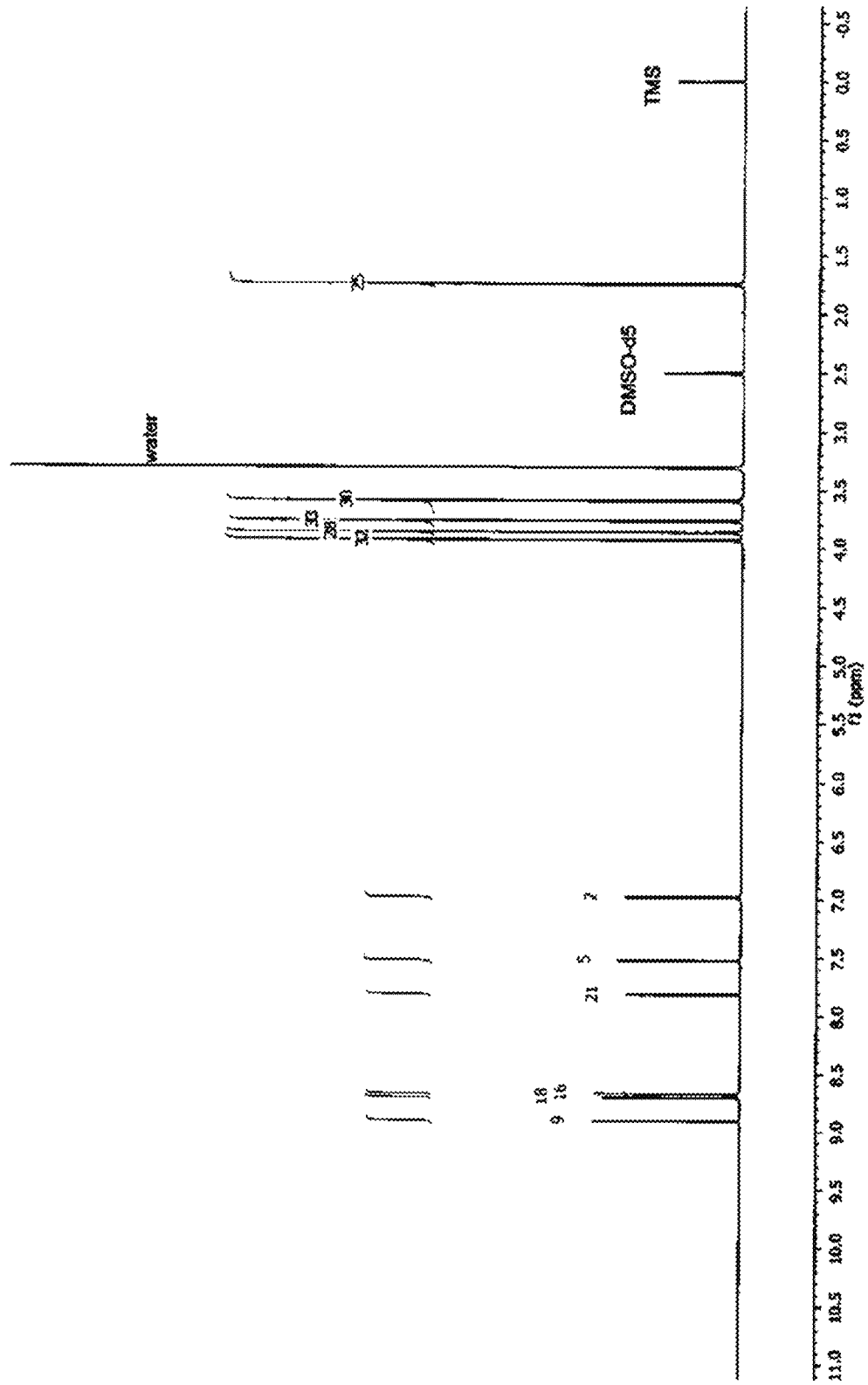
FIG. 1 depicts an annotated $^1$H NMR spectrum of Compound 1.

International patent application WO 2016/155884, the entirety of which is hereby incorporated by reference, describes imidazolonyl quinoline compounds that effectively inhibit, regulate and/or modulate signal transduction by ATM kinase. Such compounds include Compound Y:

Compound Y

Compound Y is designated as Example 4 in WO 2016/155884 and is active in a variety of assays and therapeutic models demonstrating selective inhibition of ATM kinase over P3Kalpha, PI3Kbeta, PI3Kdelta, PI3Kgamma and mTOR (in enzymatic and cellular assays).

The terms used here for the definition of the compounds are generally based on the rules of the IUPAC organisation for chemical compounds and in particular organic compounds.

It has now been surprisingly found that Compound Y exists in the form of two atropisomers, which can be isolated and are beneficially stable, and that said atropisomers exhibit surprising and very desirable characteristics.

According to one aspect, the present invention provides the following two compounds, which are atropisomers of Compound Y:

8-(1,3-Dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one (Compound 1) and 8-(1,3-Dimethyl-1H-pyrazol-4-yl)-1-(Ra)-(3-fluoro-5-methoxy-pyridin-4-yl)-7-methoxy-3-methyl-1,3-dihydro-imidazo[4,5-c]quinolin-2-one (Compound 2), as well as pharmaceutically acceptable salts thereof.

Compounds 1 and 2 are represented by the following formulae:

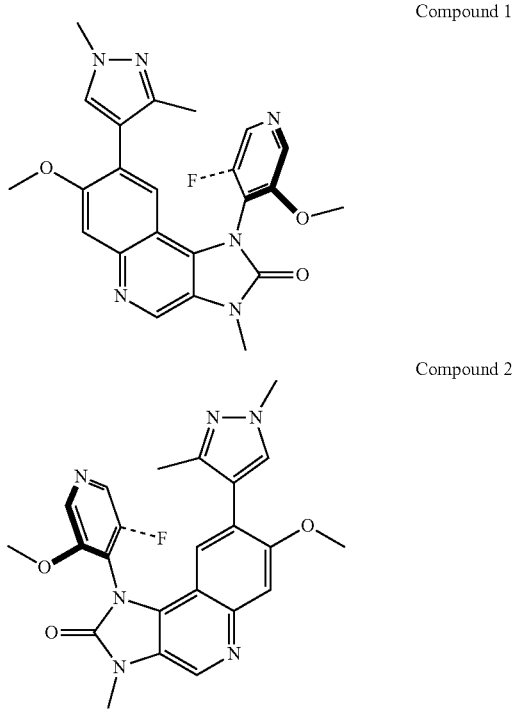

Compound 1

Compound 2 wherein the bold and dashed sections of compounds 1 and 2 denote the partial rotation of the pyridine ring out of the plane in which the tricyclic ring is situated.

It will be appreciated by one of ordinary skill in the art that the term "atropisomer" as used herein refers to a stereoisomer which arises due to a restricted rotation around a single bond that creates a chiral axis. It will be further appreciated that the rotation barrier around said single bond has to be sufficiently high to permit the isolation of a single atropisomer. Said rotation barrier can result, for example, from steric interactions with other residues of the same molecule thereby restricting said rotation around said single bond. Both steric and electronic factors come into play and may reinforce or counteract one another.

The utilization of chiral compounds that contain asymmetric carbon atoms is well established in drug discovery, in principle. In particular, it is known in the art that racemic mixtures of two chiral compounds usually consist of one more active and one less active enantiomer as compared to the racemic mixture. Thus, the utilization of only one of the two enantiomers can be advantageous to improve the overall potency of the compound.

However, the utilization of atropisomers, which are stereoisomers that arise only due to a hindered rotation around a single bond, is generally seen as undesirable. In particular, atropisomers are commonly regarded as a liability in drug discovery, since the stability of these isomers depends on energy differences resulting from steric strain or other factors that create a barrier to the rotation around said single bond. In contrast to chiral compounds resulting from asymmetric carbon atoms, atropisomerism cannot be readily predicted. In particular, it is generally not possible to readily predict the stability of an atropisomer. In particular, the height of said energy barrier determines the time of the interconversion of two corresponding atropisomers. The interconversion of a biologically active atropisomer into the corresponding other atropisomer can, thus, reduce its biological activity and introduce off-target or other unwanted effects. Therefore, only stable atropisomers that possess a sufficiently high energy barrier may be suitable in drug discovery.

It has been surprisingly found that the atropisomers Compound 1 and Compound 2 do not significantly interconvert into the respective other atropisomer, even after extensive periods of time of more than ten years (a rotational half-life of >10 ten years was determined by computer simulations) and at temperatures exceeding room temperature. The inversion temperature of the atropisomers has been assessed as being more than 100° C. in solution. This very good stability has been confirmed experimentally. It renders those atropisomers readily suitable for pharmaceutical application, manufacture, formulation and provides for sufficient shelf-life.

Figure 2:
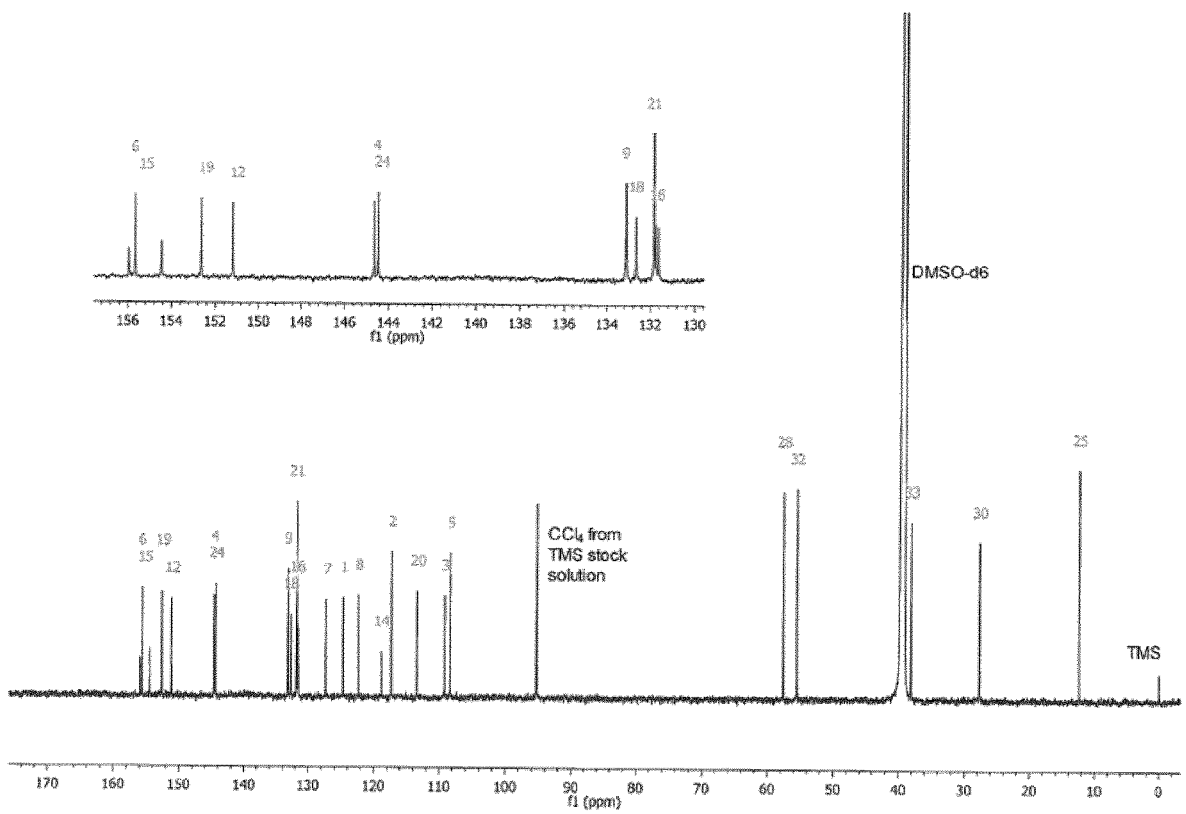
FIG. 2 depicts an annotated $^{13}$C NMR spectrum of Compound 1.
Figure 3:
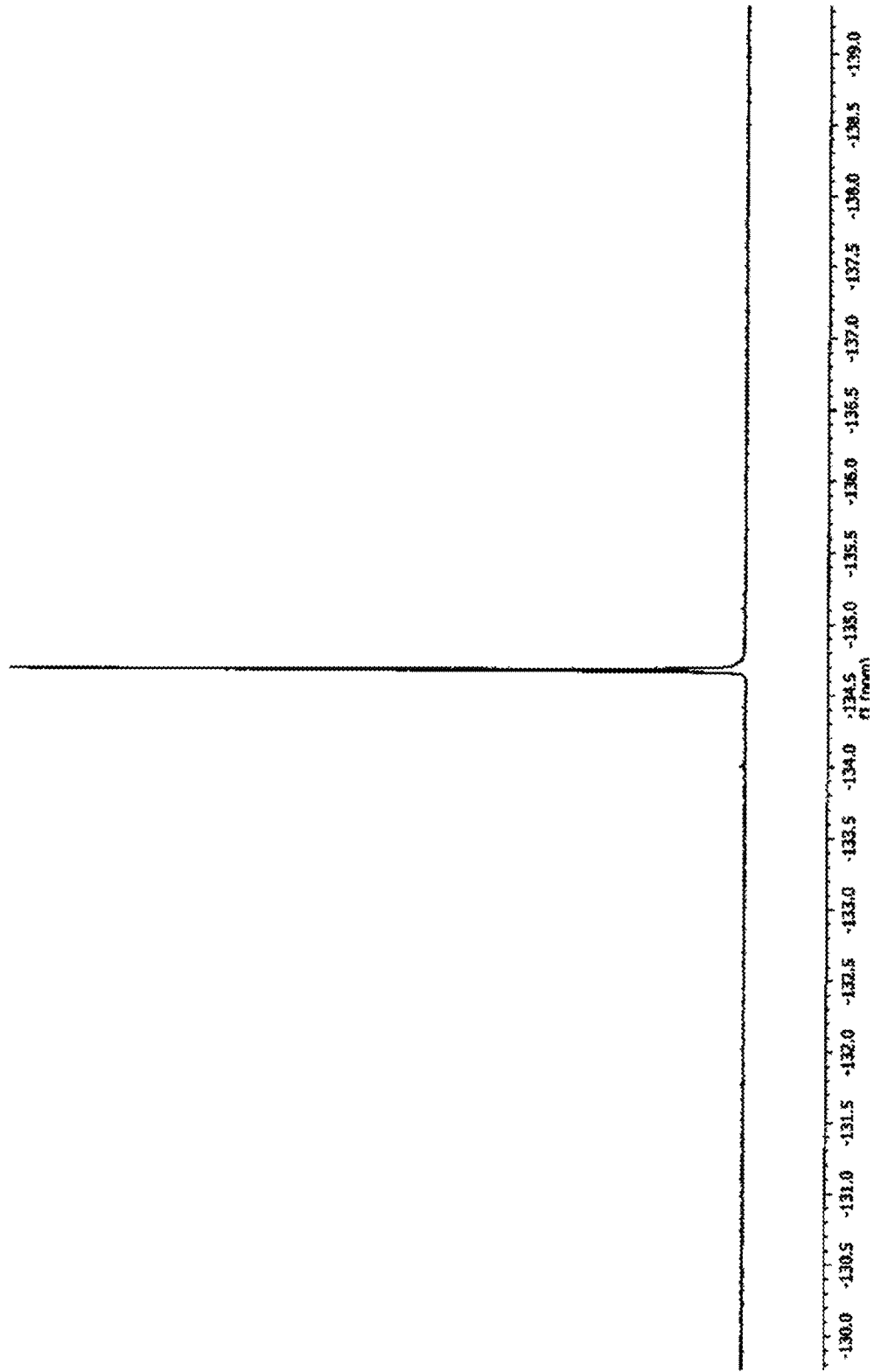
FIG. 3 depicts an annotated $^{19}$F NMR spectrum of Compound 1.
Figure 4:
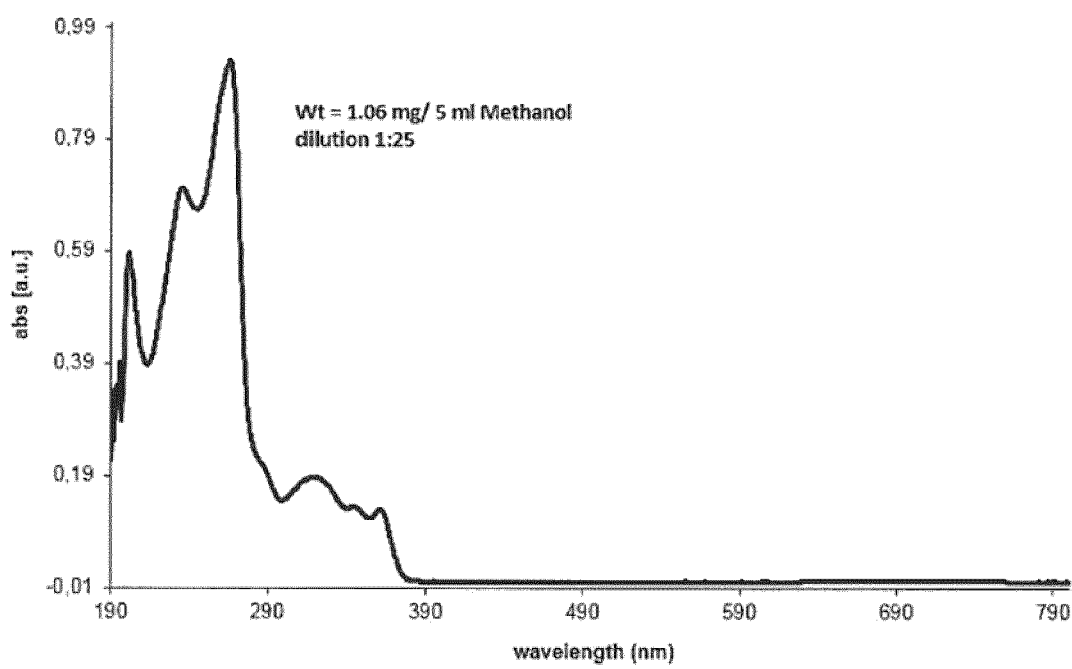
FIG. 4 depicts a UV-Vis spectrum of Compound 1 in Methanol.
Figure 7:
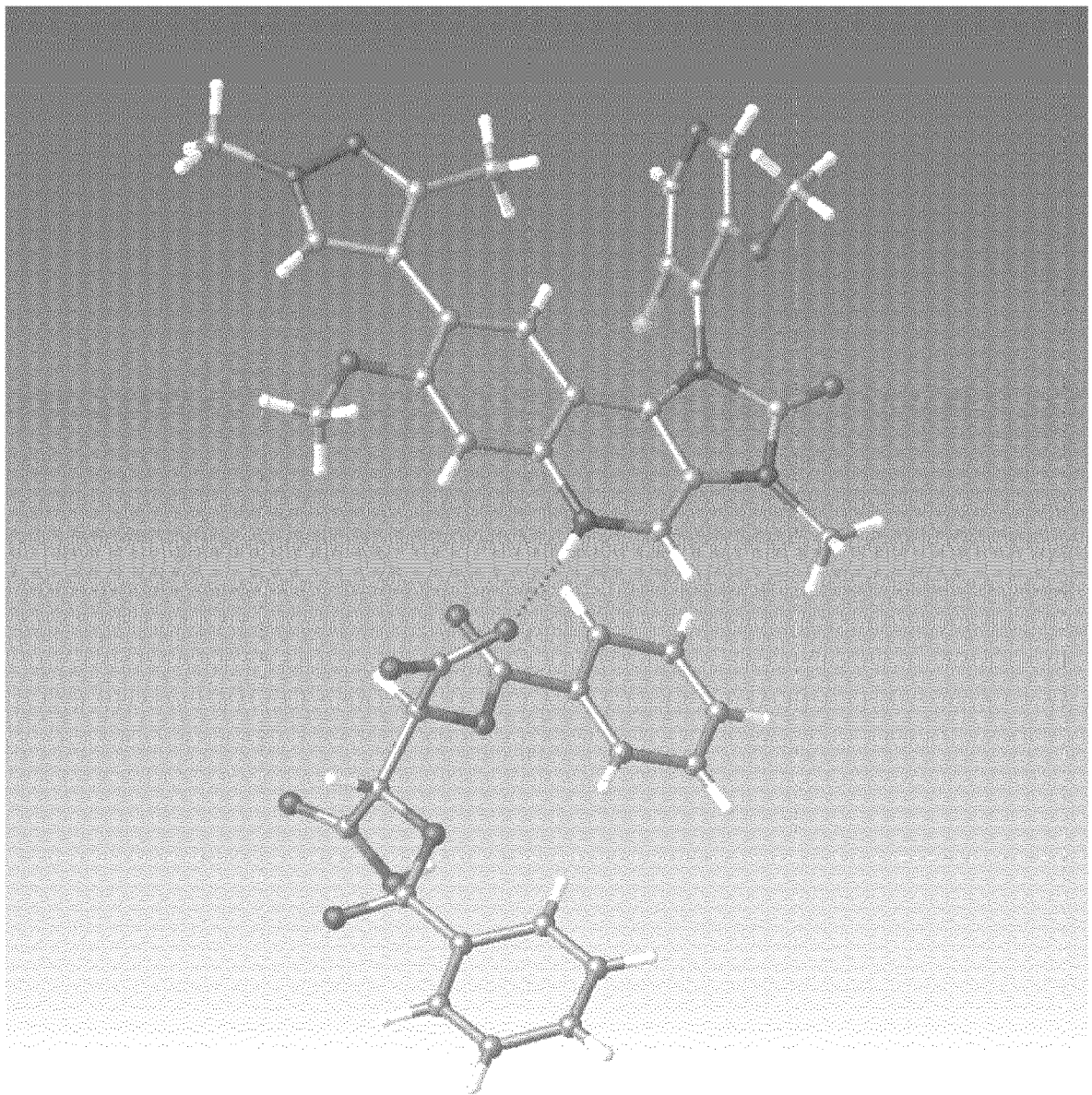
FIG. 7 depicts a crystal structure of Compound-1-Dibenzoyl-D-tartrate (A) and XRPD (B) thereof.
Figure 7:
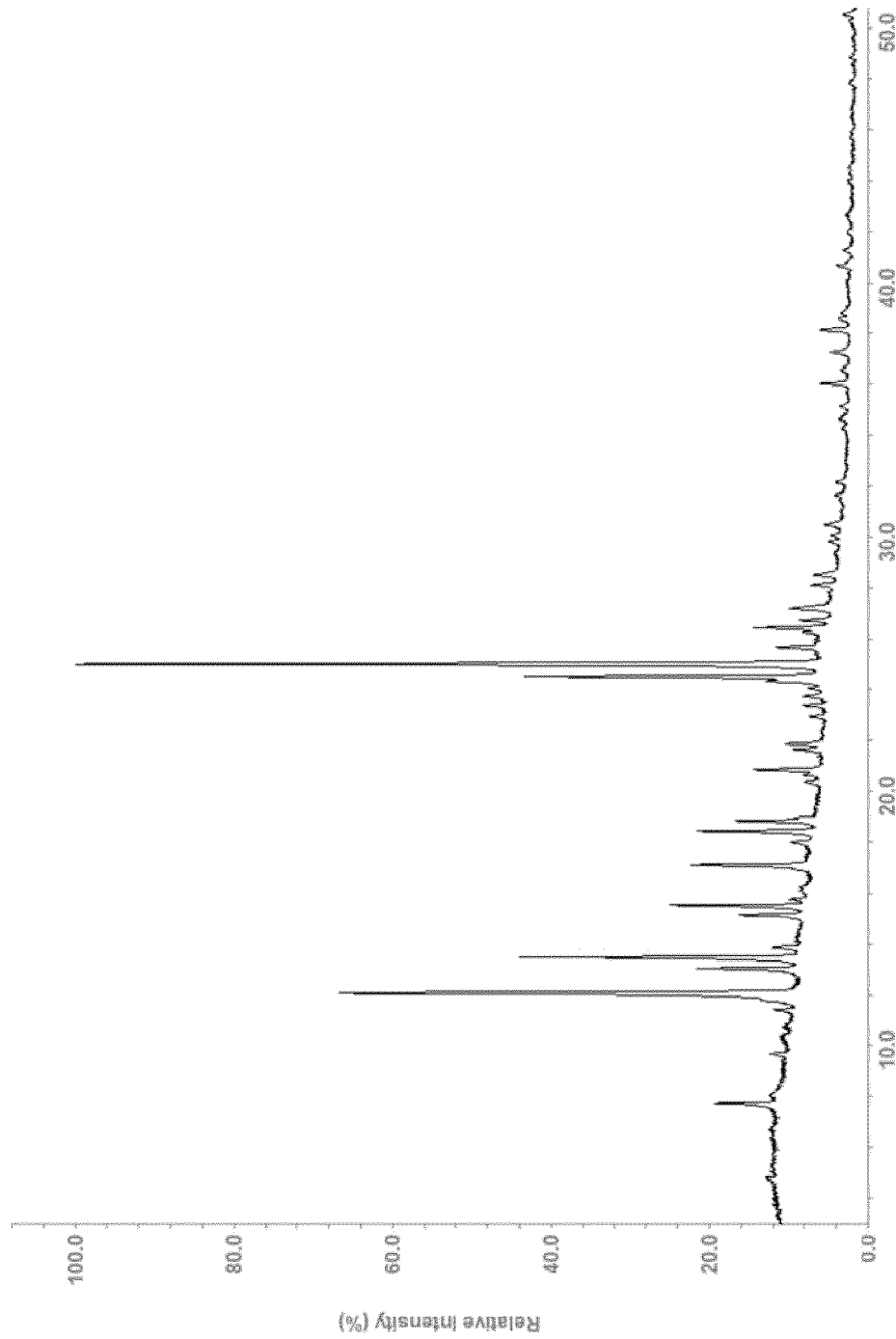
Figure 8:
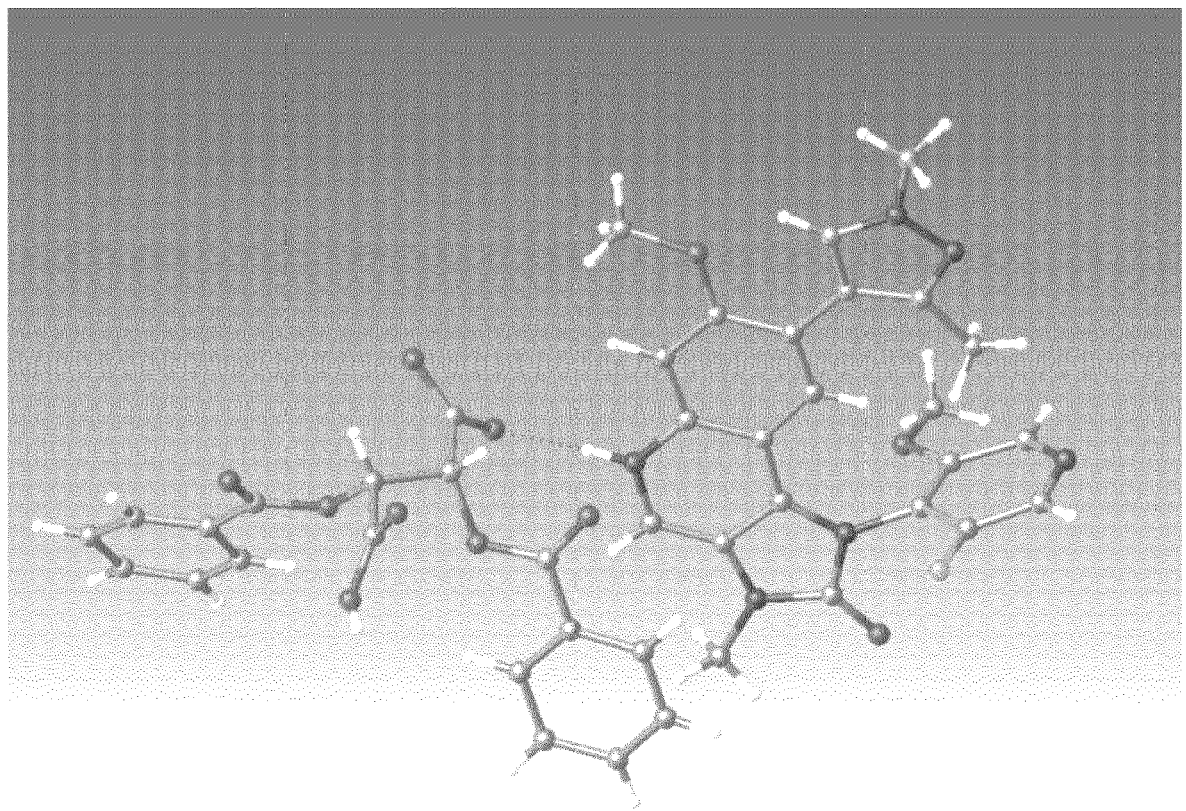
FIG. 8 depicts a crystal structure of Compound-2-Dibenzoyl-L-tartrate.
Figure 13:
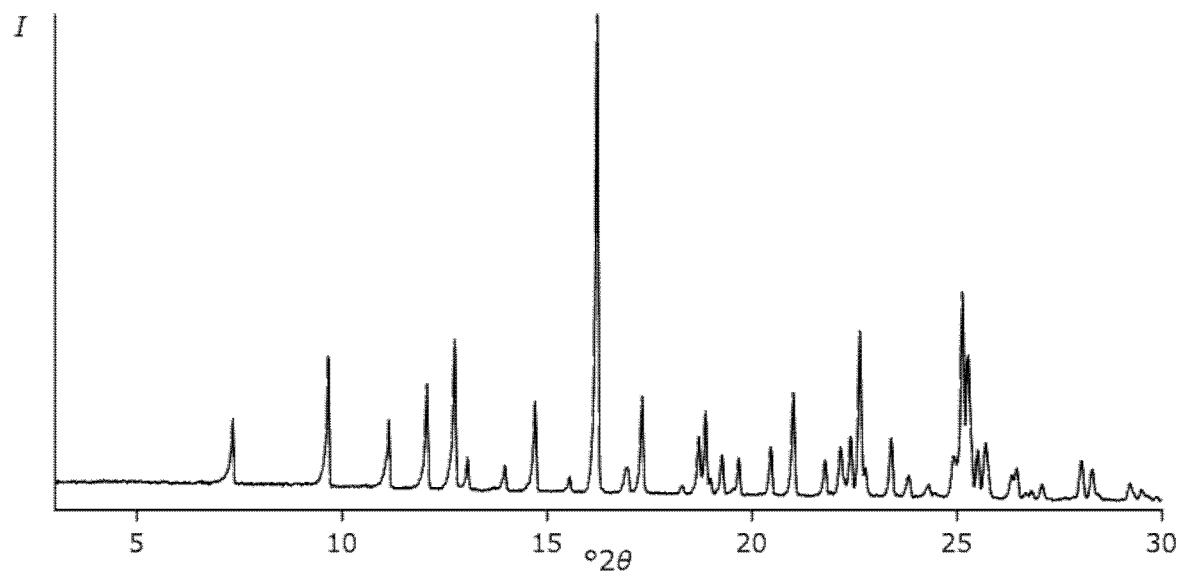
FIG. 13 depicts an X-ray powder diffraction (XRPD) pattern of solid Form A2 of Compound 1.

The absolute structure of Compound 1 has been determined on the basis of the (2S,3S)-Dibenzoyl-D-tartaric acid salt, as well as from X-ray diffraction of solid Form A2, which will be described in more detail below. The structure of Compound 1 has been proven by the results from spectroscopy (NMR, MS, IR and UV), X-ray diffraction, elementary analysis and polarimetry. $^1$H-, $^{13}$C- and $^{19}$F-NMR spectra of Compound 1 are shown in FIGS. 1 to 3, the UV-Vis-Spectrum is shown in FIG. 4. XRPD of solid form A2 of Compound 1 is illustrated in FIG. 13. Crystal structure and XRPD of Compound-1-Dibenzoyl-D-tartrate are shown in FIGS. 7A and B, the crystal structure of Compound-2-Dibenzoyl-L-tartrate is illustrated in FIG. 8.

Compounds 1 and 2 are very potent inhibitors of ATM kinase. As illustrated by Table 1, Compound 1 has evidently superior values of ATM inhibition in all assays as compared to Compound Y, which is a mixture of Compounds 1 and 2:

TABLE 1

| Assay/IC$_{50}$ | Compound 1 | Compound 2 | Compound Y |
|---|---|---|---|
| ATM (ATP conc. = 10 μM) | 0.20 nM | 0.63 nM | 0.22 nM |
| ATM (ATP conc. = 1000 μM) | 0.7 nM | 8.8 nM | 1.9 nM |
| pCHK2 (Cellular mechanistic ATM, HCT-116) | 13 nM | 76 nM | 86 nM |

Even further, said compounds are selective over related kinases, including mTOR (>30,000 nM), DNA-PK and, most notably, ATR. Surprisingly, both Compounds 1 and 2 are less potent inhibitors of ATR kinase as compared to Compound Y, i.e. more advantageous in terms of selectivity.

TABLE 2

| Assay/IC$_{50}$ | Compound 1 | Compound 2 | Compound Y |
|---|---|---|---|
| ATR | 10,000 nM | >28,000 nM | 5060 nM |
| pCHK1 (Cellular mechanistic ATR, HCT-116) | ≥24,000 nM | >30,000 nM | 7,900 nM |
| DNA-PK | 600 nM | 1,290 nM | 980 nM |
| pDNA-PK (Cellular mechanistic DNA-PK, HCT-116) | >30,000 nM | >30,000 nM | >30,000 nM |

While Compound 2 is not dissimilar to Compound Y as far as ATM inhibition is concerned (s. Table 1), it has significantly better selectivity over both ATR and DNA-PK than Compound Y, as apparent from above Table 2.

The compounds of the present invention can therefore be particularly advantageously used to selectively address specific DNA repair mechanisms, in particular homologous recombination, which specifically targets DNA double-strand damages.

A further advantage of the selective ATM inhibitors Compounds 1 and 2 is a reduction of toxicities, in particular in relation to off-target effects, and thus, a tolerability of higher compound dosages. Therefore, the compounds according to the invention open up new possibilities in cancer therapy, For example, Compounds 1 and 2, most preferably Compound 1, may be used in targeted combination therapies, for example comprising a potent and selective ATM inhibitor and a potent and selective other inhibitor, for instance ATR inhibitor.

Overall, Compound 1 has been found to have the most beneficial overall combination of properties. Surprisingly, it does not only have the best ATM inhibiting properties, but also best microsomal clearance values and lowest inhibition of phosphodiesterase (PDE) 2A1 as well as PDE4A1A and PDE4D2. Phosphodiesterase inhibition itself is associated with a variety of pharmacological effects, and PDE inhibitors are available as medicaments for the treatment of a diversity of conditions, including depression, multiple sclerosis and chronic obstructive pulmonary disease, to name but a few, all of which would constitute off-target effects in the present case. PDE4 inhibition is also known to be associated with the risk of inducing nausea and thus to be avoided. Therefore, high IC$_{50}$ values, i.e. poor inhibition of these off-targets, is desirable. As apparent from the following Table 3, Compound 1 has IC$_{50}$ values for PDE4 inhibition that are by a factor of about 5 higher than those of Compound Y.

TABLE 3

| Assay/IC$_{50}$ | Compound 1 | Compound 2 | Compound Y |
|---|---|---|---|
| CLint (human/rat/mouse) [μl/min/mg protein] | <10, <10, 22 | <10, <10, 103 | 19, 19, 61 |
| PDE2A1 | 2.2 μM | 3.9 μM | 1.4 μM |
| PDE4A1A | 5.2 μM | 0.93 μM | 1.1 μM |
| PDE4D2 | 3.0 μM | 0.44 μM | 0.6 μM |

Table 4 illustrates further advantageous parameters of Compound 1, including a favourably high bioavailability of about 80% and favourable properties regarding CYP and hERG (cardiac ion channel), the latter indicating that no safety-relevant interactions with the cardiac Kv11.1 hERG ion channel are to be expected.

TABLE 4

|  | Compound 1 |
|---|---|
| K$_i$ Kv11.1 hERG cardiac ion channel (patch clamp) | >30 μM |
| CYP inhibition | ≥20 μM |
| Bioavailability (predicted human parameter) | ~80% |

It was further surprisingly found that both Compounds 1 and 2 show a significantly improved solubility in biological buffer solutions (see Table 5 below) as compared to Compound Y. The predicted slow human plasma clearance and high bioavailability of Compound 1 contribute to appropriate low dose requirements.

TABLE 5

| Solubility | Compound 1 | Compound 2 | Compound Y |
|---|---|---|---|
| PBS, pH 7.4 | ~100 μg/ml | ~100 μg/ml | 19 μg/ml |
| FaSSiF, pH 6.5 | 242 μg/ml | 216 μg/ml | 52 μg/ml |
| FeSSiF, pH 5.0 | 731 μg/ml | ~800 μg/ml | 201 μg/ml |

The structures depicted for Compounds 1 or 2 are meant to include compounds that differ only in the presence of one or more isotopically enriched atoms. For example, H, C, N, in each case also include the heavier isotopes of these atoms. This applies, in particular to H, where deuterium or tritium can advantageously be employed, and to the replacement of a carbon by a $^{13}$C- or $^{14}$C-enriched carbon which is also within the scope of this invention. In certain preferred embodiments, no isotopically enriched atoms are used, instead the atoms are used in their naturally occurring forms regarding isotope distribution.

Reference to compounds or salts according to the present invention shall be regarded as also encompassing solvated forms, i.e. solvates thereof, that means solvates of both the free form or a salt. Solvates are taken to mean adducts of inert solvent molecules onto the compounds which form owing to their mutual attractive force. Solvates are, for example, mono- or dihydrates or alcoholates. Exemplary embodiments of solvates are disclosed in more detail below.

As set out above, the present invention provides two stable atropisomers, Compounds 1 and 2. Preparation of these two atropisomers is typically based on separation and purification techniques, as will be described in more detail below. The person skilled in the art appreciates that this may not yield perfectly pure products. However, the present invention provides Compound 1 substantially free of Compound 2, and Compound 2 substantially free of Compound 1. "Substantially free" in the present context shall preferably mean that substantially pure Compound 1 may contain at most 20% by weight of Compound 2 or salt thereof, preferably at most 15% by weight, more preferably at most 10% by weight, for instance at most 5% by weight, at most 2.5% by weight, at most 1% by weight, at most 0.5% by weight or at most 0.1% by weight of Compound 2 or salt thereof, the remainder to 100% being made up of Compound 1. In one example, substantially pure Compound 1 may consist of 99% by weight of Compound 1 and 1% by weight of Compound 2. The same applies vice versa to Compound 2, i.e. Compound 2 being substantially free of Compound 1 shall preferably mean that pure Compound 2 may contain at most 20% by weight of Compound 1 or salt thereof, with the preferred ranges disclosed for Compound 1 being equally applicable (vice versa) by analogy. Also, reference to Compound 1 or salt thereof, respectively Compound 2 or salt thereof, shall include all solvates and solid forms, such as those disclosed herein further below, even without specific mentioning, unless explicitly described otherwise.

In other embodiments, the present invention provides Compound 1 or 2 substantially free of impurities. As used herein, the term "substantially free of impurities" means that the compound shall not contain any significant amount of extraneous matter. Such extraneous matter may include residual Compound 1 or salt thereof, residual Compound 2 or salt thereof, residual solvents, or any other impurities that may result from the preparation of, and/or isolation of, Compound 1 or 2. In certain embodiments, Compound 1 may contain no more than 30% by weight extraneous matter, the remainder to 100% by weight being made up by Compound 1, preferably no more than 25% by weight, no more than 20% by weight, no more than 15% by weight, no more than 10% by weight, no more than 7.5% by weight, no more than 5% by weight, no more than 1% by weight, no more than 0.5% by weight or no more than 0.1% by weight. The same exemplary embodiments are valid, by analogy, to Compound 2. Also, as before, reference to Compound 1 or salt thereof, respectively Compound 2 or salt thereof, shall include all solvates and solid forms, such as those disclosed herein further below, unless explicitly described otherwise.

According to another embodiment, Compound 1 or 2, respectively, contains no more than about 5.0 area percent HPLC of total organic impurities and, in certain embodiments, no more than about 3.0 area percent HPLC of total organic impurities and, in certain embodiments, no more than about 1.5 area percent HPLC total organic impurities relative to the total area of the HPLC chromatogram. In other embodiments, Compound 1 or 2 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram. For instance, for the HPLC chromatogram, the method described in EXAMPLE 3.3 for the analysis of the purity of the respective atropisomers may be used. Again, reference to Compound 1 or salt thereof, respectively Compound 2 or salt thereof, shall include all solvates and solid forms, such as those disclosed herein further below, unless explicitly described otherwise.

According to another embodiment, the present invention provides a pharmaceutical composition that comprises an effective amount of Compound 1 or pharmaceutically acceptable salt thereof. In an alternative embodiment, the pharmaceutical composition comprises an effective amount of Compound 2 or pharmaceutically acceptable salt thereof. According to another embodiment, the present invention provides a method of preparing such compositions described herein (for example, a composition that can include an effective amount of either Compound 1 or 2). Reference to Compound 1 or 2 shall be read in the present context such that any amount of the respective other atropisomer can only amount to that in harmony with the definitions of "substantially free of" the respective other atropisomer, "substantially free of impurities" or total amount of impurities, respectively, i.e. would count towards the amount of the mentioned compound rather than being separately present. The same applies to the respective salts. As set out before, the reference to Compound 1 or 2 or salt thereof shall equally include any solid form or solvate, such as those further disclosed herein below, unless specifically described otherwise. In exemplary embodiments, Compound 1 is contained in the pharmaceutical composition in its free, i.e. non-salt form.

Still other embodiments provide a method of treating cancer using a compound or composition respectively pharmaceutical composition or pharmaceutically acceptable salt thereof as described herein. According to another embodiment, the present invention provides the use of a compound, pharmaceutically acceptable salt thereof or (pharmaceutical) composition according to the present invention in the manufacture of a medicament for treating cancer. In another embodiment, the present invention provides a compound or pharmaceutical composition, as described herein, for the use as a medicament, in particular for the treatment of cancer. Again, reference to a compound or salt thereof, shall include any solvate or solid form of those compounds or salts, such as those disclosed herein further below, unless explicitly described otherwise.

Free Form and Salts

The compounds according to the invention can be used in their free form, i.e. as shown by the formulae above. For instance, the free form of Compound 1 has been found to be particularly beneficial, and exemplary solid forms thereof, including a preferred solid form, will be described in more detail below.

On the other hand, the present invention also encompasses the use of these compounds in the form of their pharmaceutically acceptable salts, which can be derived from various organic and inorganic acids by procedures known in the art. Suitable pharmaceutically acceptable salts of the compounds according to the invention can be prepared by conventional methods. A compound according to the invention can be converted into the associated acid-addition salt using an acid, for example by reaction of the compound and an equivalent or excess amount of acid in a suitable solvent, such as, for example, THF or acetone followed by cooling crystallisation of the thus formed saturated solution. Alternatively, anti-solvent crystallisation or evaporation crystallisation may be employed.

Examples of suitable pharmaceutically acceptable salts of the compounds according to the present invention, in particular Compound 1, include an HCl salt, sulfate salt, tosylate salt, besylate salt, lactate salt, in particular L-lactate salt.

Preferred salts of compound 1 include a fumarate salt, a napsylate salt and an edisylate salt, which may also be collectively referred to as Compounds 1a in the following.

Compound 1 napsylate can be prepared from Compound 1 using naphthalenesulfonc acid and either THF or acetone as the solvent. Good crystallinity was obtained. The preferred ratio of Compound 1:napsylate is about 1:1.

Compound 1 edisylate can be obtained using ethanedisulfonic acid and cooling crystallization from acetone. The preferred ratio of Compound 1:napsylate is about 1:1. Good crystallinity was obtained.

Compound 1 fumarate can be obtained by anti-solvent vapour diffusion in THF using n-pentane as the anti-solvent and fumaric acid as the acid. The ratio of Compound 1:fumarate was shown to be about 1:0.9. The resulting salt has very favourable overall physical properties and good crystallinity. The fumarate salt is a preferred embodiment amongst the salts, partly due to the desirable absence of hygroscopic properties.

Detailed examples of suitable methods of preparing the fumarate, napsylate and edisylate salts of Compound 1 according to the present invention are disclosed in EXAMPLE 5.

Figure 9:
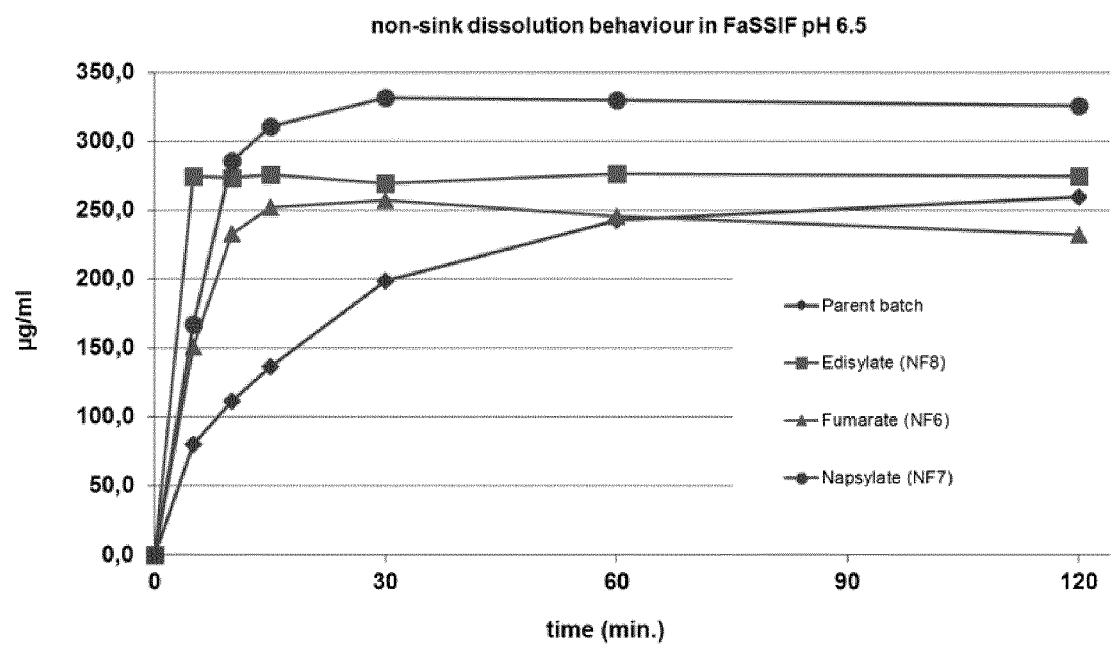
FIG. 9 depicts a chart of the non-sink dissolution behavior in FaSSIF of Compound 1 and specific salts thereof.

It has been found that these salts of Compound 1 show a faster initial dissolution rate than the parent Compound 1. The non-sink dissolution behavior in FaSSIF buffer solution (pH 6.5) of Compound 1 and specific salts thereof is exemplarily depicted in FIG. 9. The salts with advantageous dissolution behaviour are Compound 1 edisylate, Compound 1 fumarate and Compound 1 napsylate. The parent compound 1 was used in the form of a mixture of various crystalline and solvated forms.

It will be appreciated by one of ordinary skill in the art that the anionic moiety from the acid and Compound 1 are ionically bonded to form Compound 1-a. It is contemplated that Compound 1-a can exist in a variety of physical forms. For example, Compound 1-a can be in solution, suspension, or in solid form. In certain embodiments, Compound 1-a is in solid form. When Compound 1-a is in solid form, said compound may be amorphous, crystalline, or a mixture thereof. As used herein, the term "polymorph" refers to the different crystal structures in which a compound or salt thereof can crystallize.

In some embodiments, Compounds 1-a are crystalline solids substantially free of amorphous Compound 1-a. As used herein, the term "substantially free of amorphous Compound 1-a" means that the salt contains no significant amount of amorphous Compound 1-a. In certain embodiments, at least about 90% by weight of crystalline Compound 1-a is present, or at least about 95% by weight of crystalline Compound 1-a is present. In still other embodiments of the invention, at least about 99% by weight of crystalline Compound 1-a is present. These percentages are relative to the absolute weight of Compound 1-a (100 wt. %).

Figure 10:
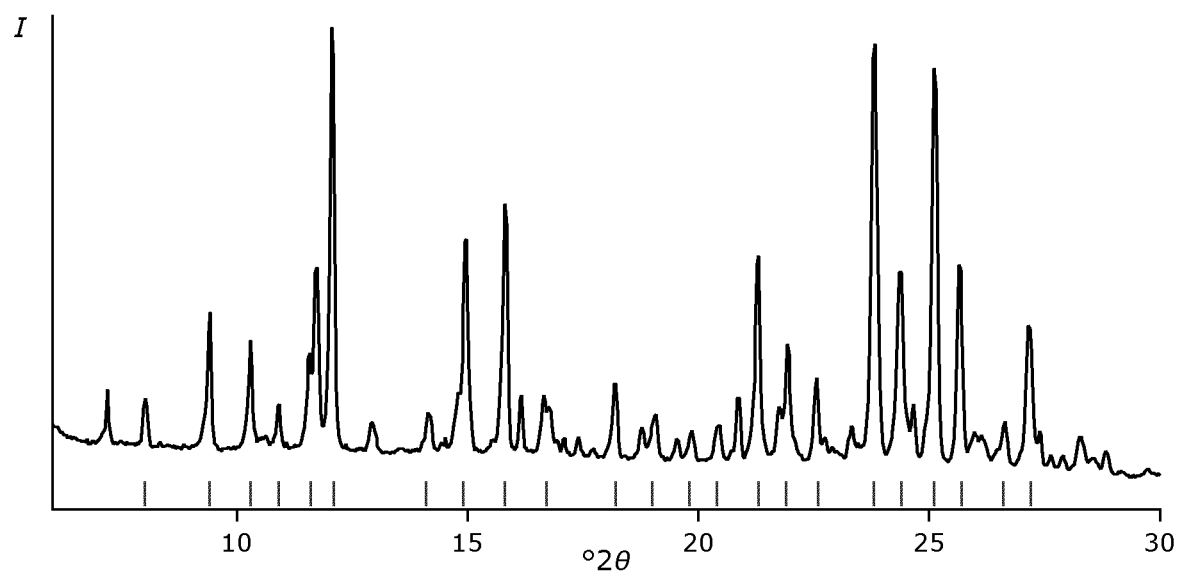
FIG. 10 depicts an X-ray powder diffraction (XRPD) pattern of a solid form of Compound 1 fumarate.

In an exemplary embodiment, the present invention provides a solid form of Compound 1 fumarate, characterized by a powder X-ray diffraction pattern substantially in line with that depicted in FIG. 10 and/or characterized by one or more peaks in its powder X-ray diffraction pattern selected from those at about

| Fumarate Salt | |
|---|---|
| Peak No. | °2-Theta |
| 1 | 8 |
| 2 | 9.4* |
| 3 | 10.3* |
| 4 | 10.9 |
| 5 | 11.6 |
| 6 | 12.1* |
| 7 | 14.1 |
| 8 | 14.9* |
| 9 | 15.8* |
| 10 | 16.7 |
| 11 | 18.2 |
| 12 | 19 |
| 13 | 19.8 |
| 14 | 20.4 |
| 15 | 21.3 |
| 16 | 21.9 |
| 17 | 22.6 |
| 18 | 23.8* |
| 19 | 24.4 |
| 20 | 25.1* |
| 21 | 25.7 |
| 22 | 26.6 |

Figure 31:
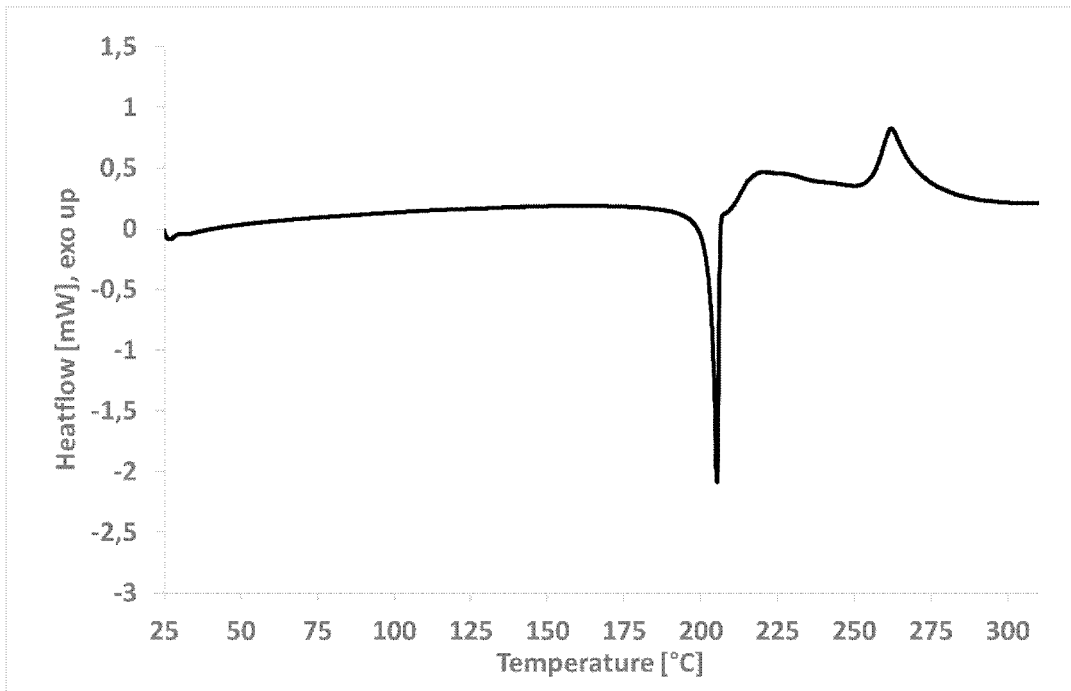
FIG. 31 depicts a DSC heating curve of Compound 1 Fumarate (Form NF6).
Figure 32:
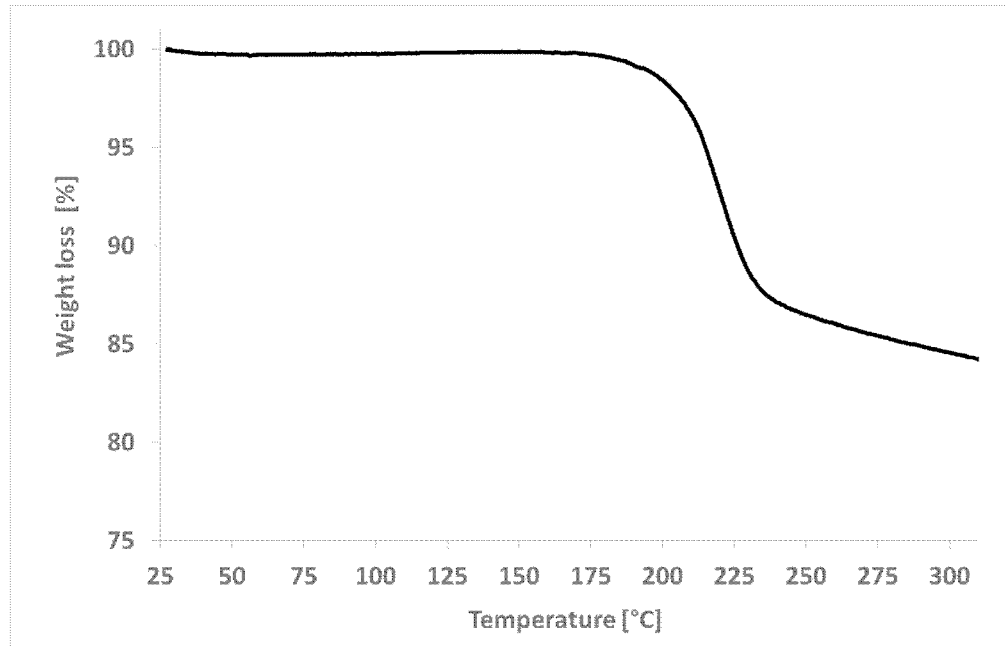
FIG. 32 shows a TGA heating curve of Compound 1 Fumarate (Form NF6).
Figure 33:
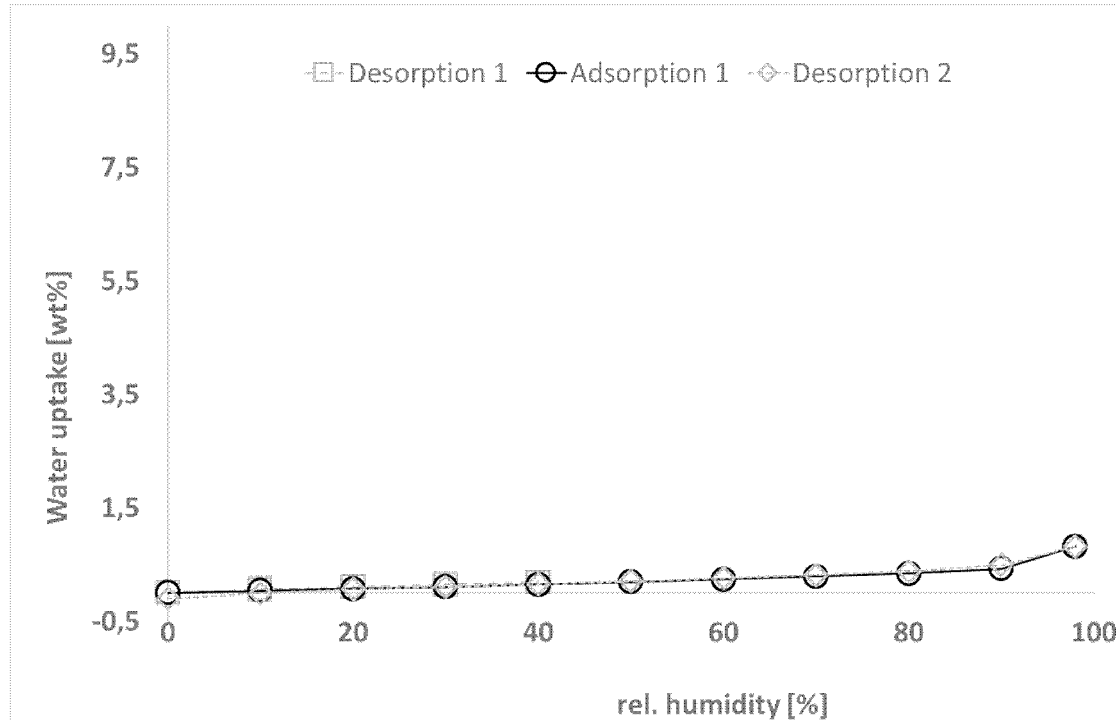
FIG. 33 shows a DVS water uptake isotherm (25° C.) of Compound 1 Fumarate (Form NF6).

The fumarate salt of Compound 1 is anhydrous. Its solid form may also be referred to as Fumarate-NF6. DSC heating curve, TGA heating curve and DVS water uptake isotherm (25° C.) of Fumarate-NF6 are depicted in FIGS. 31, 32 and 33. Results from non-sink dissolution measurements are provided in the table below (non-sink dissolution data in FaSSIF at pH 6.5, method described in the Experimental Section):

| Time (min) | Dissolved Fumarate (NF6) conc. |
|---|---|
| 5 | 150.9 µg/mL |
| 15 | 251.7 µg/mL |
| 30 | 257.0 µg/mL |
| 60 | 245.8 µg/mL |
| 120 | 232.2 µg/mL |

As used herein, the term "about", when used in reference to a degree 2-theta value refers to the stated value±0.3 degree 2-theta (° 2θ). In certain embodiments, "about" refers to ±0.2 degree 2-theta or ±0.1 degree 2-theta, most preferably ±0.2 degree 2-theta.

Any solid form respectively polymorph described herein may be characterized by one, two, three, four, five, six, seven, eight, nine, ten, eleven, twelve, thirteen, fourteen, fifteen, sixteen, seventeen, eighteen, nineteen, twenty or more of the XRD or XRPD peaks (° 2θ). Any solid form respectively polymorph described herein is preferably characterized by at least six XRD peaks (° 2θ, preferably ±0.2° 2θ). Preferred peaks for characterization of the solid form respectively polymorph are indicated by bold print and asterisks in the respective peak listings.

Figure 11:
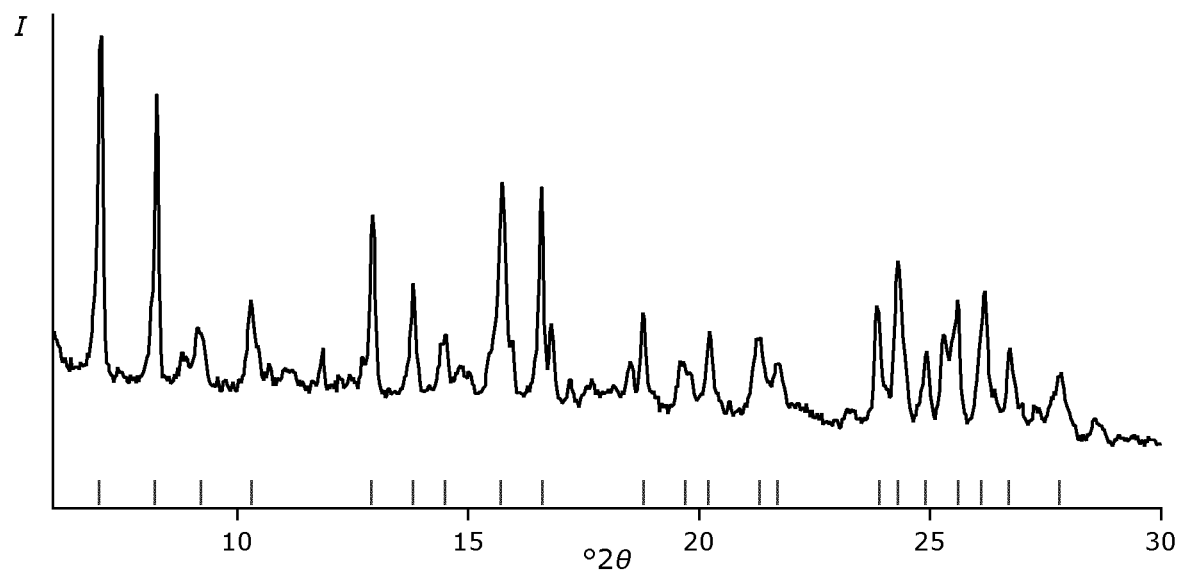
FIG. 11 depicts an X-ray powder diffraction (XRPD) pattern of a solid form of Compound 1 napsylate.

In a further exemplary embodiment, the present invention provides a solid form of Compound 1 napsylate, characterized by a powder X-ray diffraction pattern substantially in line with that depicted in FIG. 11 and/or characterized by one or more peaks in its powder X-ray diffraction pattern selected from those at about

| Napsylate salt | |
|---|---|
| Peak No. | °2-Theta |
| 1 | 7* |
| 2 | 8.2* |
| 3 | 9.2 |
| 4 | 10.3* |
| 5 | 12.9* |
| 6 | 13.8 |
| 7 | 14.5 |
| 8 | 15.7* |
| 9 | 16.6* |
| 10 | 18.8 |
| 11 | 19.7 |
| 12 | 20.2 |
| 13 | 21.3 |
| 14 | 21.7 |
| 15 | 23.9 |
| 16 | 24.3 |
| 17 | 24.9 |

Figure 34:
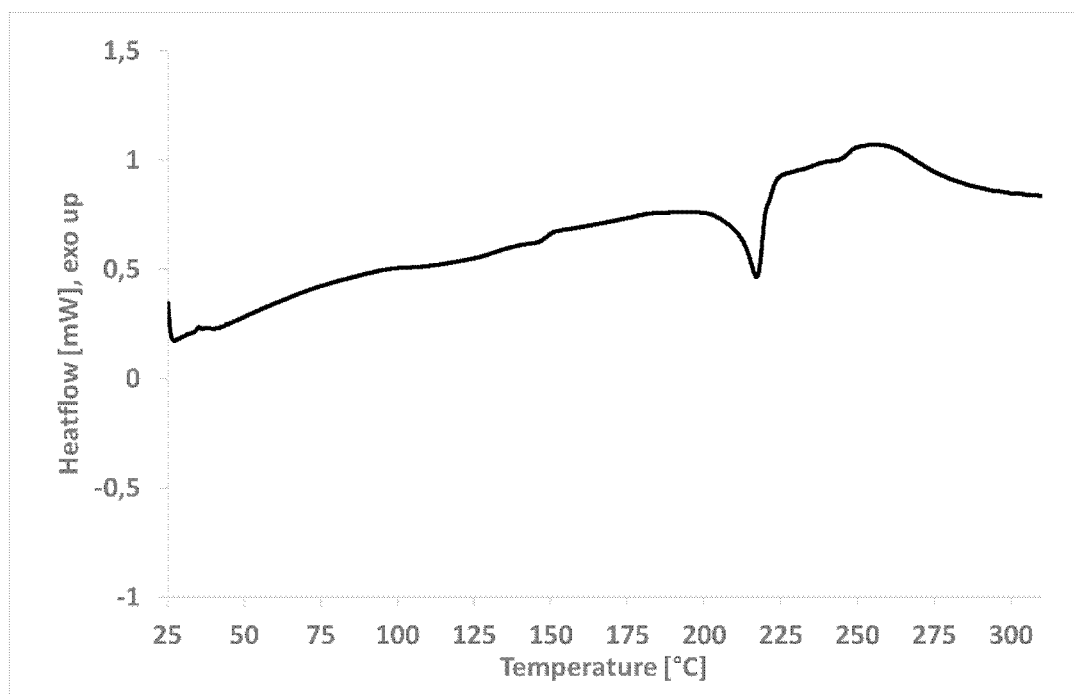
FIG. 34 depicts a DSC heating curve of Compound 1 Napsylate (NF7).
Figure 35:
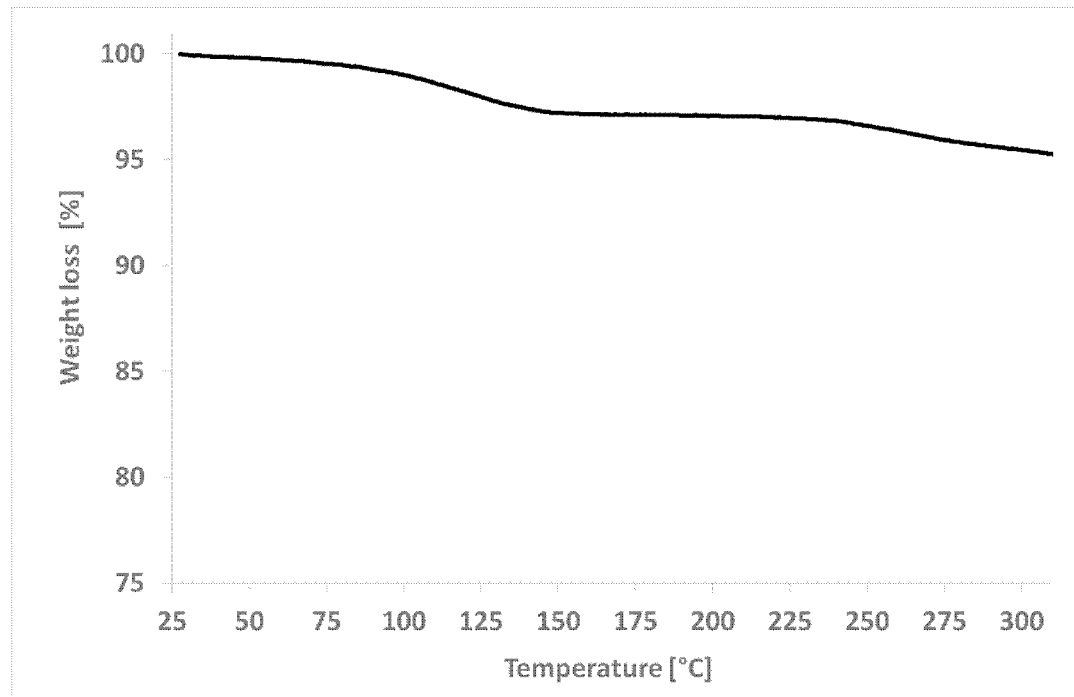
FIG. 35 shows a TGA heating curve of Compound 1 Napsylate (NF7)
Figure 36:
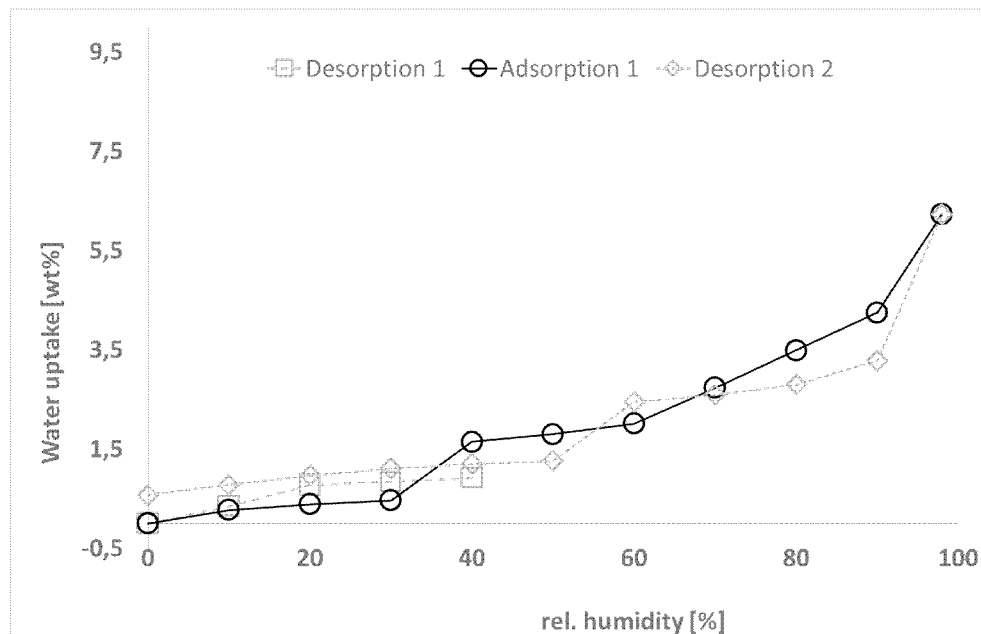
FIG. 36 depicts a DVS water uptake isotherm (25° C.) of Compound 1 Napsylate (NF7.)

Thermal and water adsorption properties of the napsylate salt of Compound 1 are illustrated in FIGS. 34, 35 and 36. The solid form obtained for the napsylate salt may also be referred to as Napsylate NF7. Furthermore, the dissolution behavior is represented by the following experimental non-sink dissolution data (FaSSIF, pH 6.5):

| Time (min) | Dissolved Napsylate conc. |
|---|---|
| 5 | 167.4 µg/mL |
| 15 | 310.6 µg/mL |
| 30 | 331.4 µg/mL |
| 60 | 329.7 µg/mL |
| 120 | 326.0 µg/mL |

Figure 12:
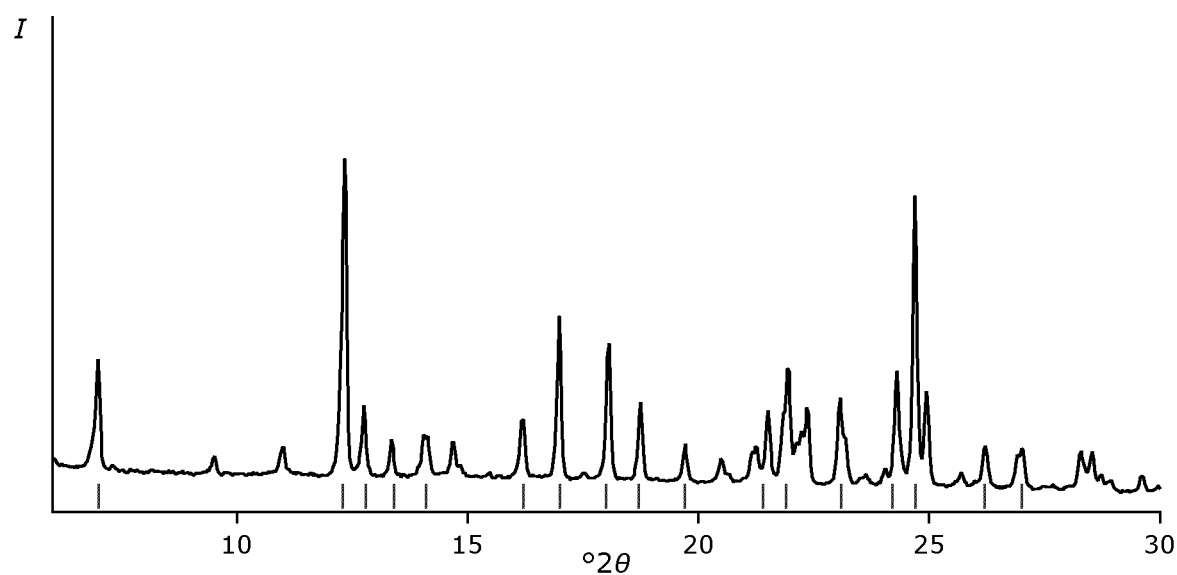
FIG. 12 depicts an X-ray powder diffraction (XRPD) pattern of a solid form of Compound 1 edisylate.

In a further exemplary embodiment, the present invention provides a solid form of Compound 1 edisylate, characterized by a powder X-ray diffraction pattern substantially in line with that depicted in FIG. 12 and/or characterized by one or more peaks in its powder X-ray diffraction pattern selected from those at about

| Edisylate Salt | |
|---|---|
| Peak No. | °2-Theta |
| 1 | 7* |
| 2 | 12.3* |
| 3 | 12.8 |
| 4 | 13.4 |
| 5 | 14.1 |
| 6 | 16.2 |
| 7 | 17* |
| 8 | 18* |
| 9 | 18.7 |
| 10 | 19.7 |
| 11 | 21.4 |
| 12 | 21.9* |
| 13 | 23.1 |
| 14 | 24.2 |
| 15 | 24.7* |
| 16 | 26.2 |
| 17 | 27 |

Figure 37:
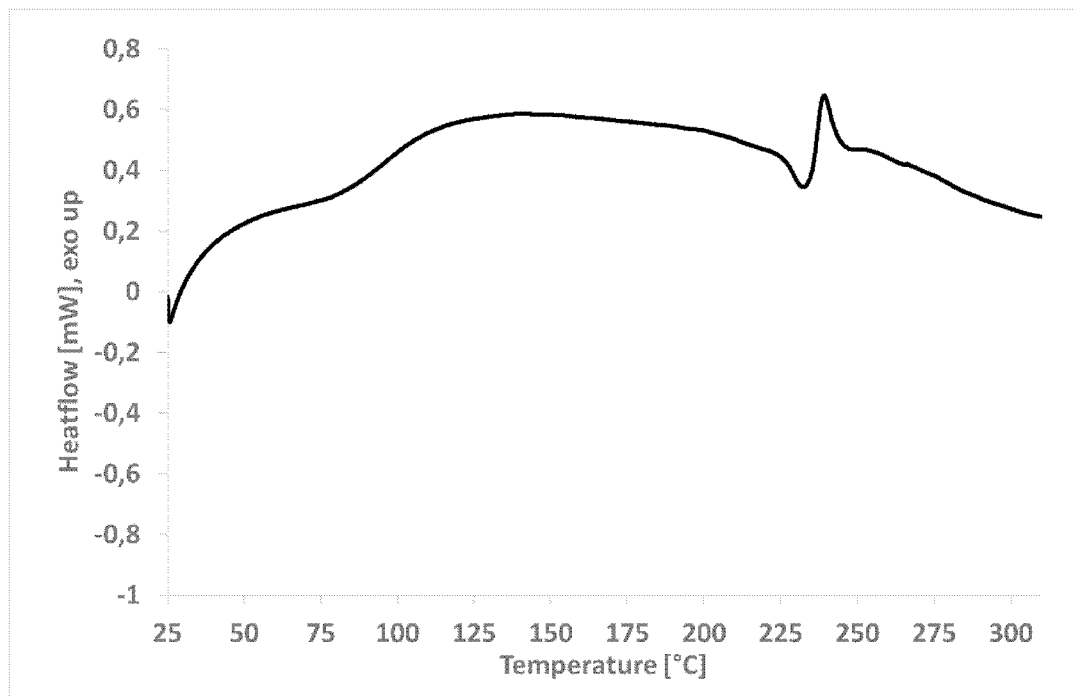
FIG. 37 depicts a DSC heating curve of Compound 1 Edisylate (NF8).
Figure 38:
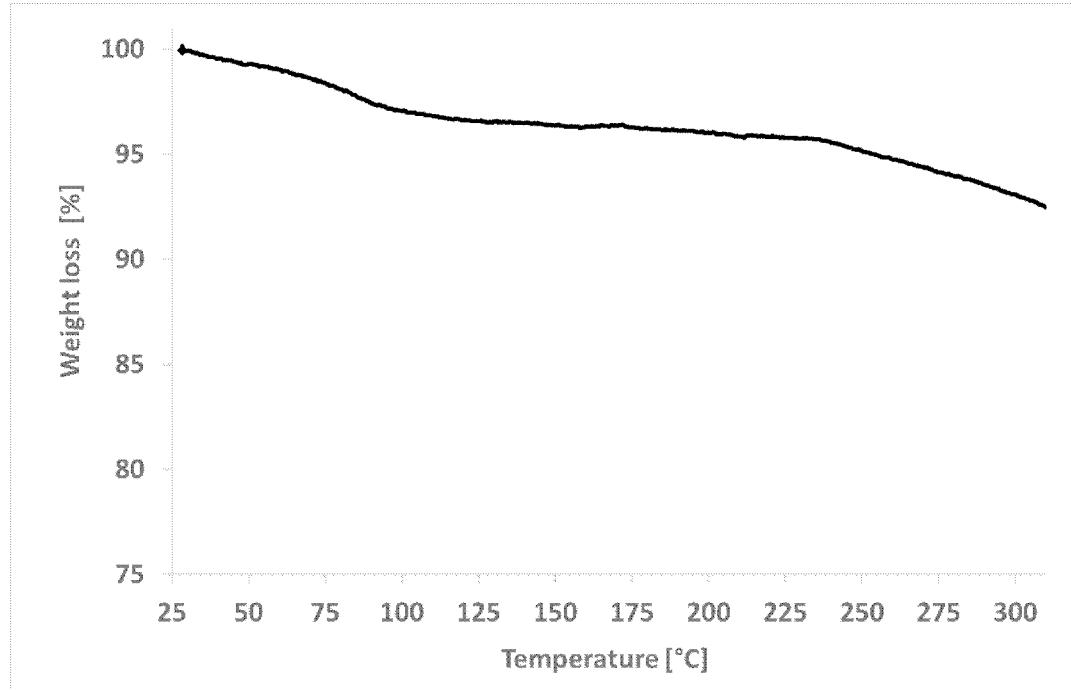
FIG. 38 shows a TGA heating curve of Compound 1 Edisylate (NF8).
Figure 39:
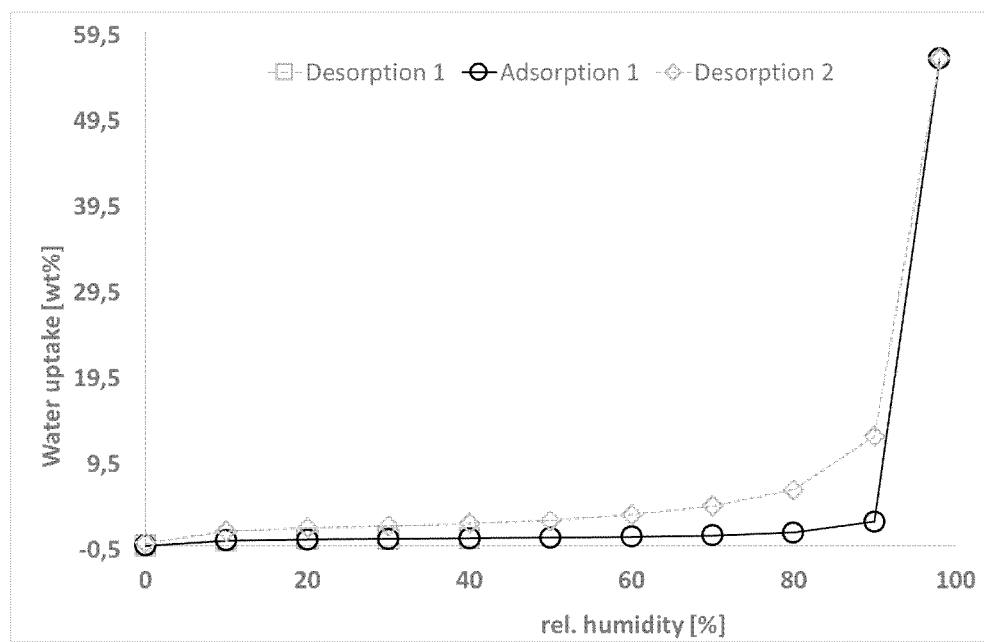
FIG. 39 depicts a DVS water uptake isotherm (25° C.) of Compound 1 Edisylate (NF8).
Figure 40:
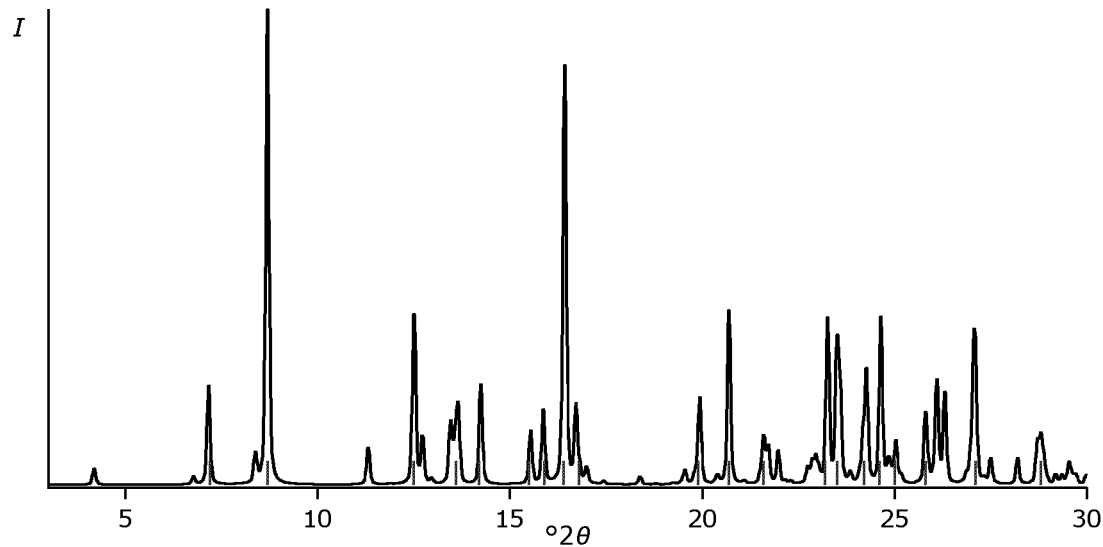
FIG. 40 shows a XRPD of a methanolate of Compound 1 in solid form S1.
Figure 41:
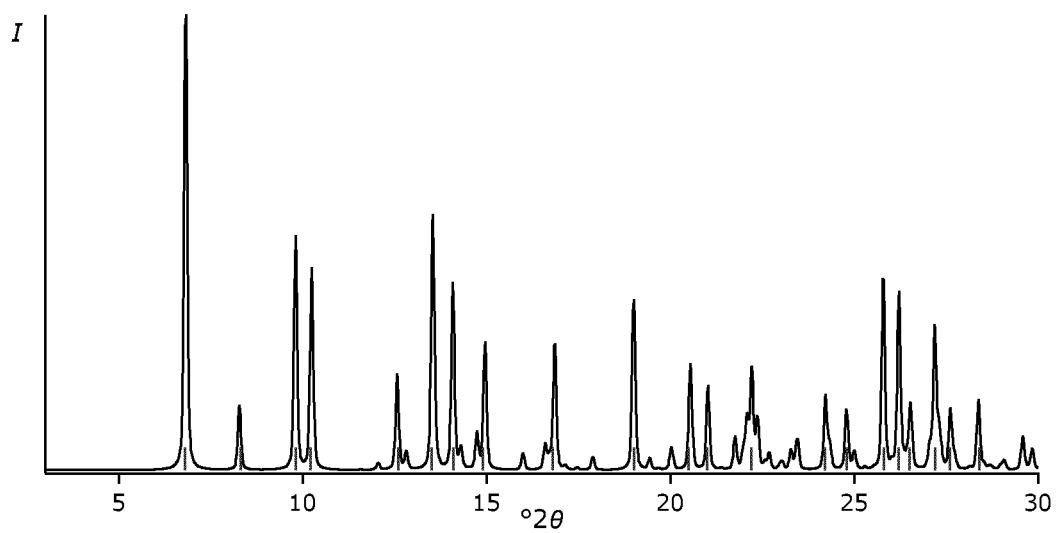
FIG. 41 depicts a XRPD of a mixed hydrate/methanolate of Compound 1 in solid form S2.
Figure 42:
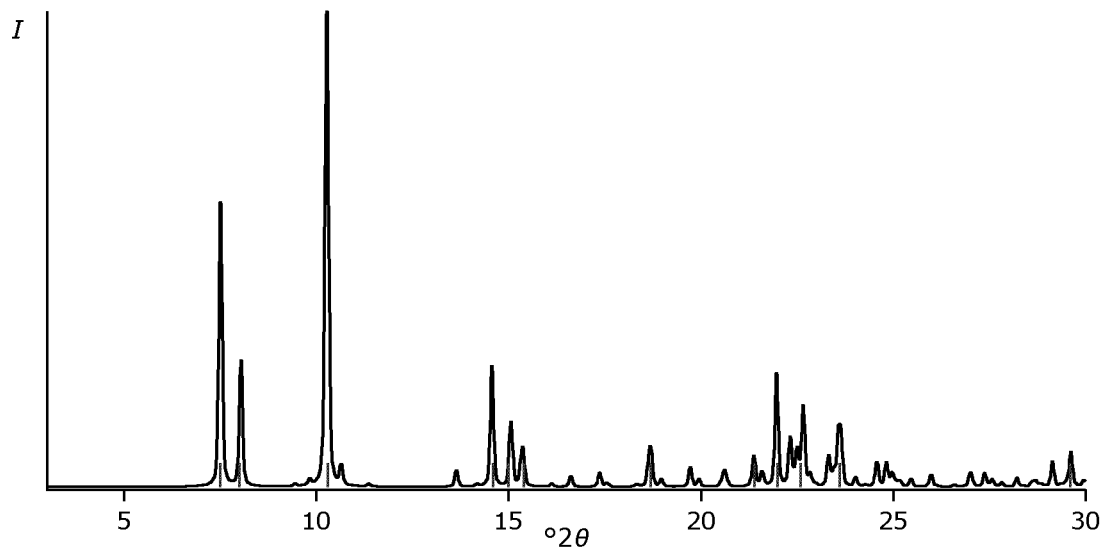
FIG. 42 shows a XRPD of a THF solvate of Compound 1 in solid form S3.
Figure 43:
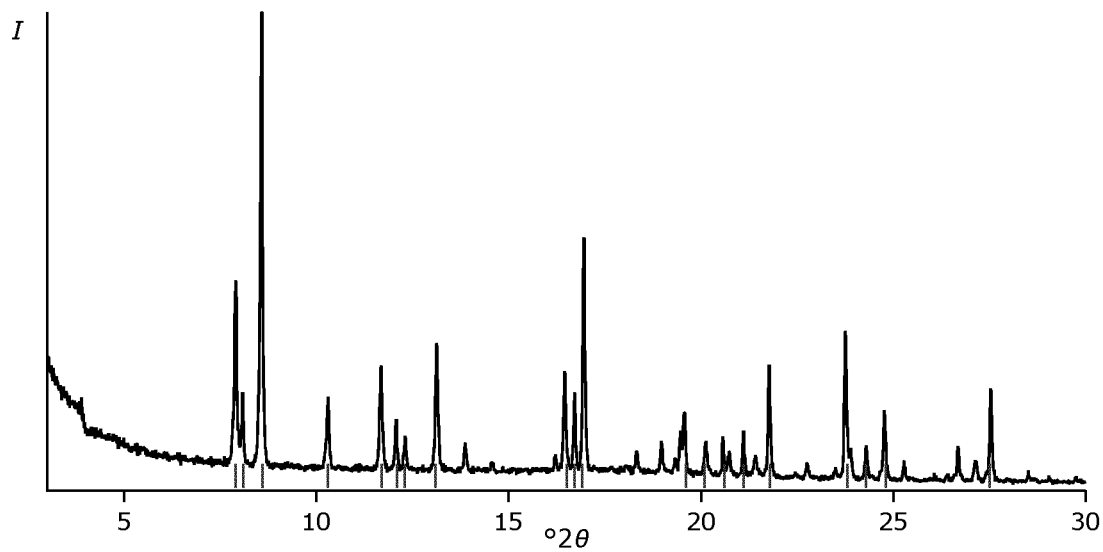
FIG. 43 depicts a XRPD of a dioxane solvate of Compound 1 in solid form NF11.
Figure 44:
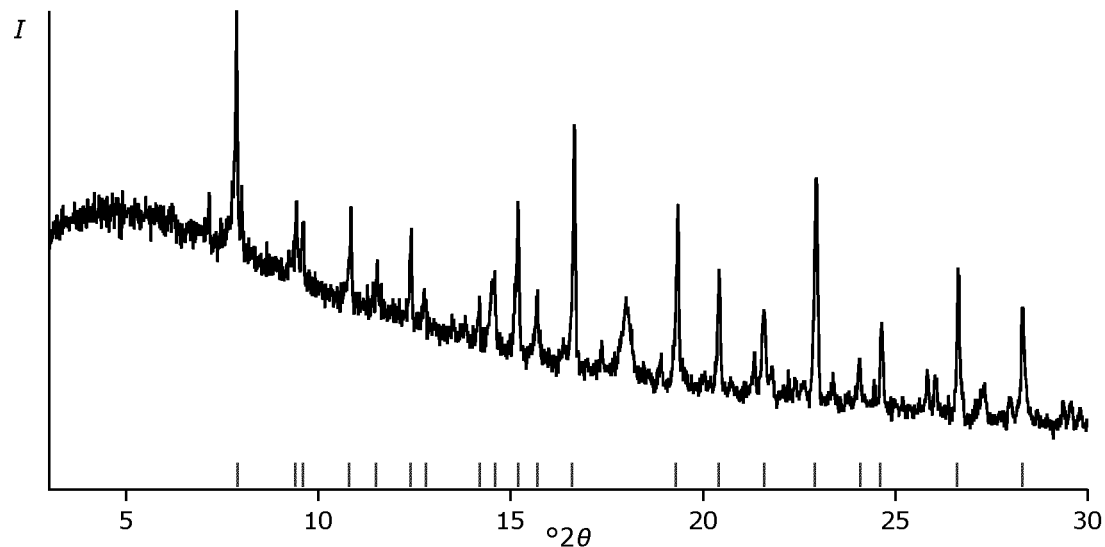
FIG. 44 shows a XRPD of a chloroform solvate of Compound 1 in solid form NF15.
Figure 45:
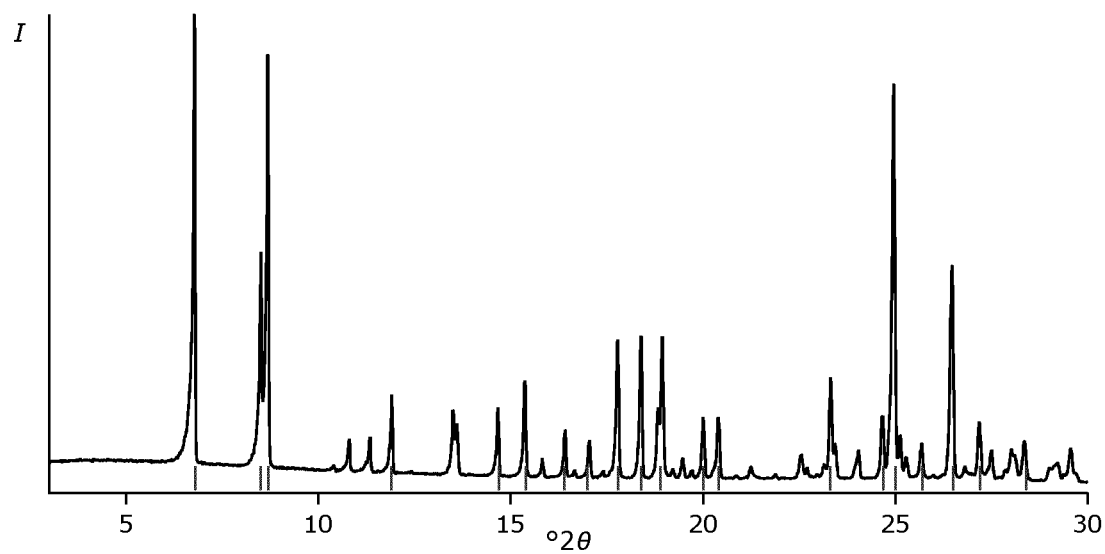
FIG. 45 depicts a XRPD of an acetic acid solvate of Compound 1 in solid form NF16.
Figure 46:
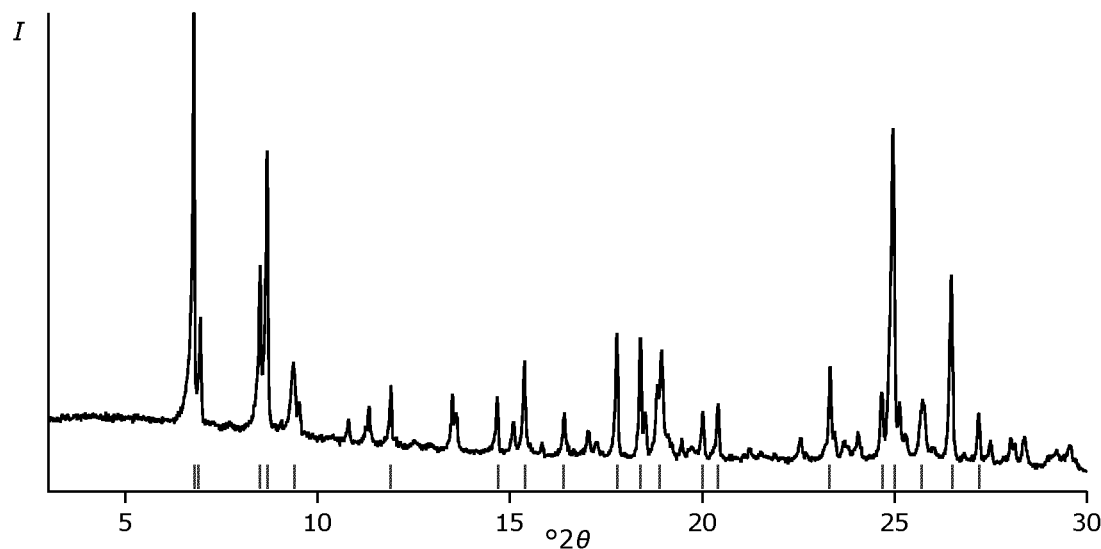
FIG. 46 shows a XRPD of an acetic acid solvate of Compound 1 in solid form NF18.
Figure 47:
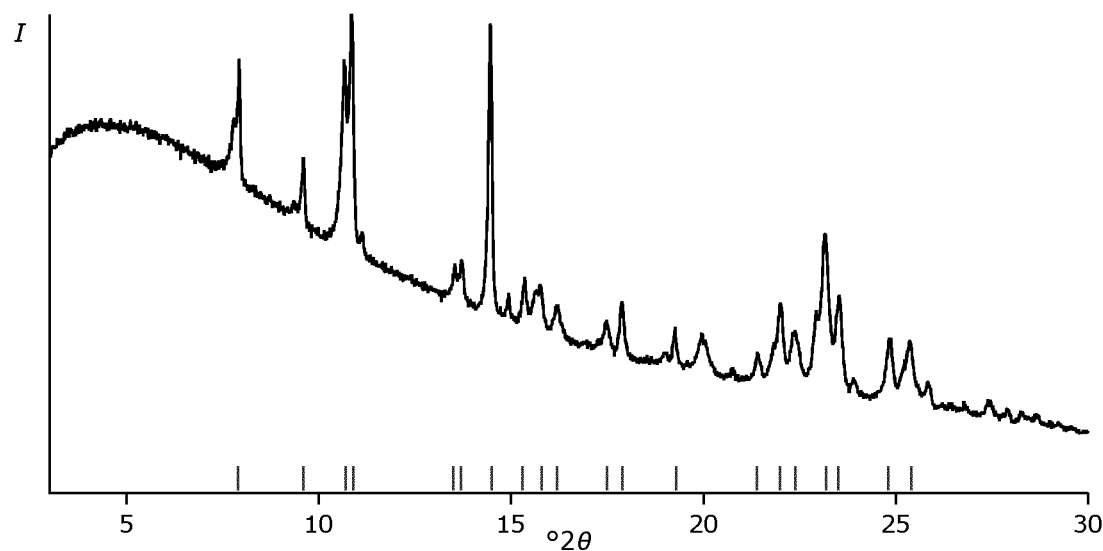
FIG. 47 depicts a XRPD of a 1,4-dioxane solvate of Compound 1 in solid form NF29.
Figure 48:
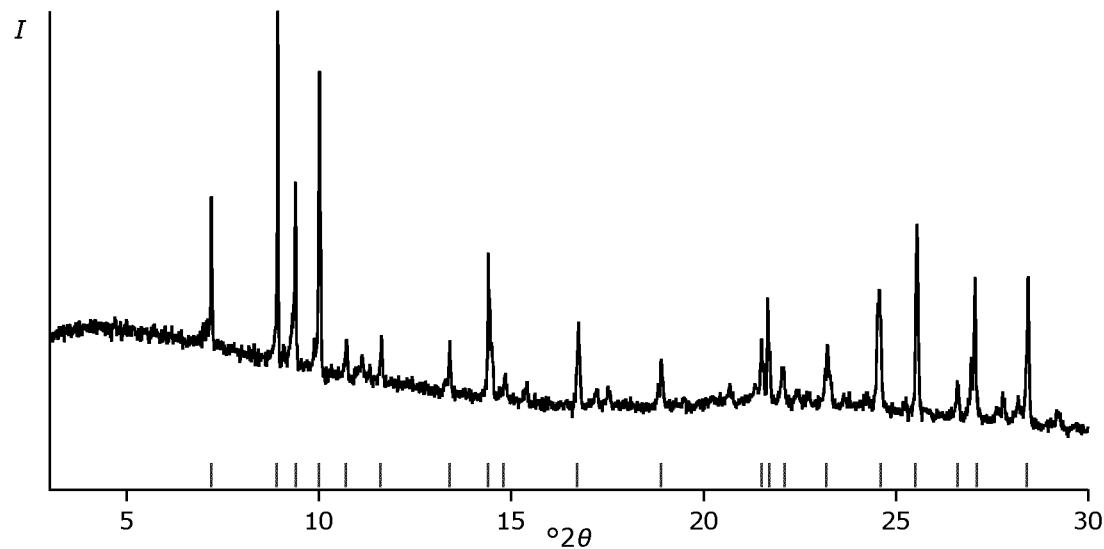
FIG. 48 shows a XRPD of a dichloromethane solvate of Compound 1 in solid form NF32.
Figure 49:
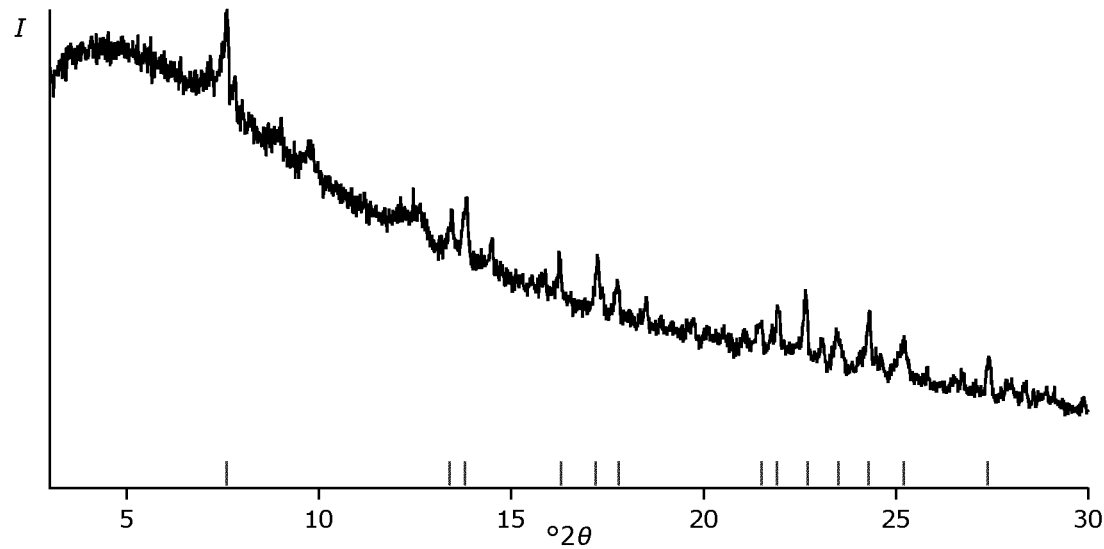
FIG. 49 depicts a XRPD of a NMP (N-Methyl-2-pyrrolidone) solvate of Compound 1 in solid form NF33.
Figure 50:
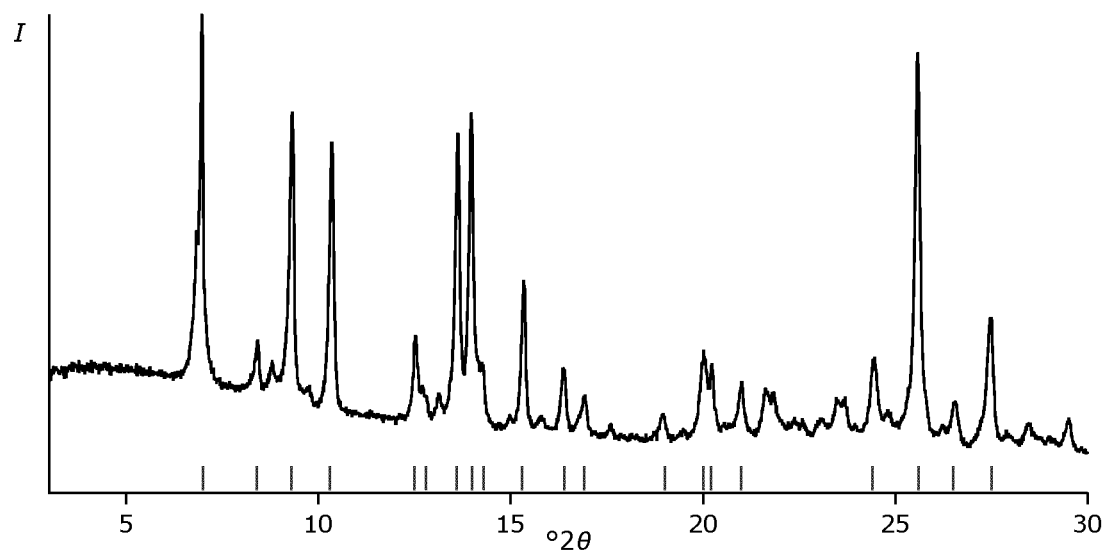
FIG. 50 shows a XRPD of an acetonitrile solvate of Compound 1 in solid form NF35.
Figure 51:
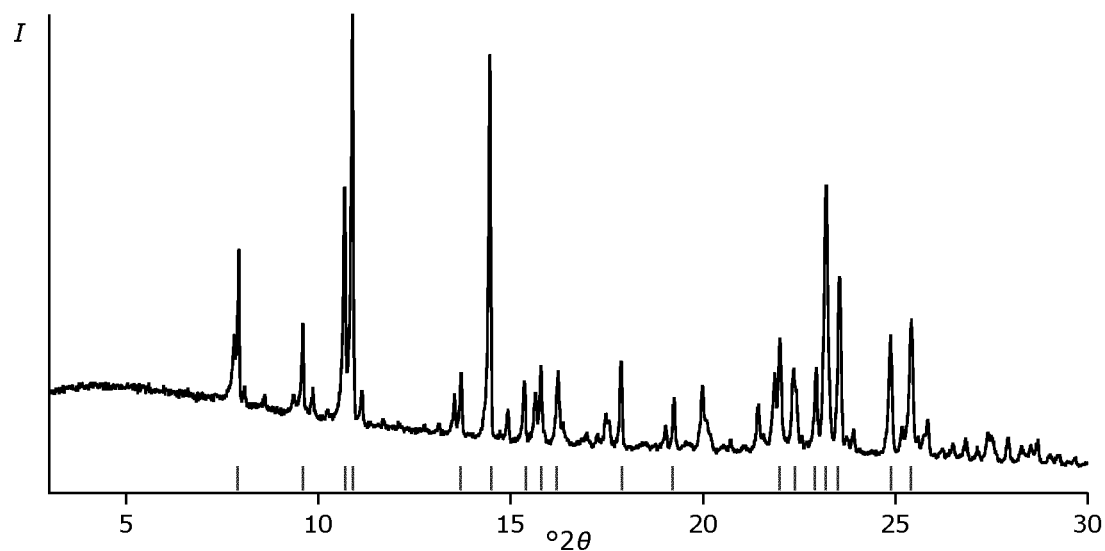
FIG. 51 depicts a XRPD of a 1,4-dioxane solvate of Compound 1 in solid form NF36.
Figure 52:
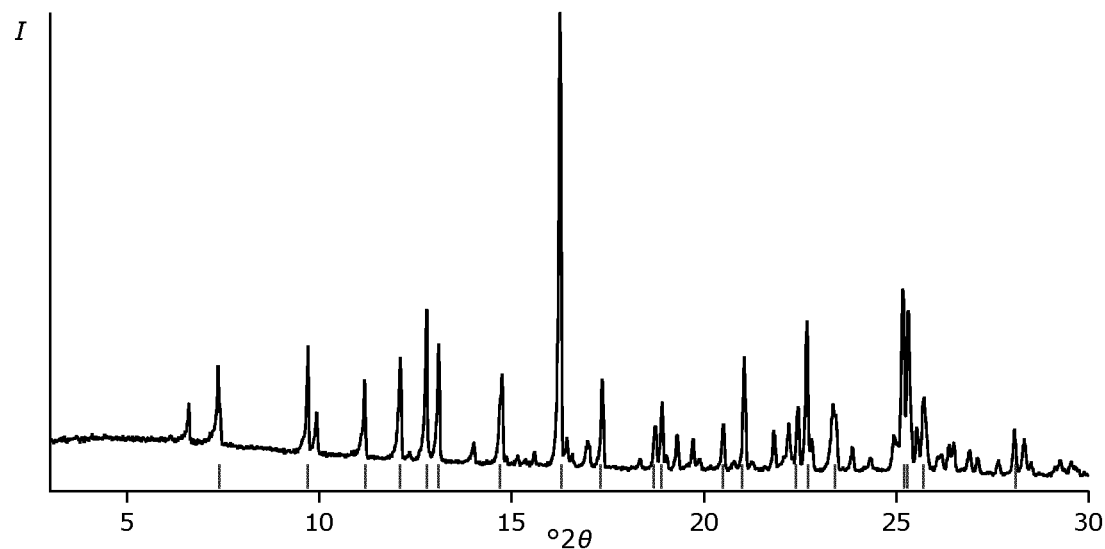
FIG. 52 shows a XRPD of a dimethylacetamide solvate of Compound 1 in solid form NF37.

Thermal properties and dissolution data of the edisylate salt of Compound 1 are illustrated by FIGS. 37, 38 and 39. The solid form of the edisylate salt may also be referred to as NF8. It is an anhydrous form/salt. Non-sink dissolution data (FaSSIF, pH 6.5) are provided in the table below:

| Time (min) | Dissolved edisyalte salt conc. |
|---|---|
| 5 | 274.5 μg/mL |
| 15 | 276.0 μg/mL |
| 30 | 269.2 μg/mL |
| 60 | 276.5 μg/mL |
| 120 | 274.7 μg/mL |

In harmony with what has been set out above with regard to Compounds 1 and 2, the present invention provides Compound 1-a or other salts of Compound 1 substantially free of Compound 2 or salt thereof. In further embodiments, Compound 1-a or another salt of Compound 1 is also provided substantially free of impurities. According to another embodiment, Compound 1-a or any other salt of Compound 1 contains no more than about 5.0 area percent HPLC of total organic impurities relative to the total area of the HPLC chromatogram. Exemplary and preferred ranges disclosed above for Compound 1 in connection with "substantially free of Compound 2 or salt thereof", "free of impurities" and area percent of total organic impurities are equally applicable here. The same applies, by analogy, to any of the salts of any of the compounds, and in particular atropisomeric compounds, according to the present invention According to another embodiment, the present invention provides a pharmaceutical composition that comprises an effective amount of a Compound 1-a. According to another embodiment, the present invention provides a method of preparing such compositions described herein (for example, a composition that can include an effective amount of Compound 1-a). Still other embodiment provides a method of treating cancer using Compound 1-a respectively a composition thereof according to the present invention. According to another embodiment, the present invention provides the use of a composition described herein in the manufacture of a medicament for treating cancer. Compound 1-a may be present in the (pharmaceutical) composition in the same amounts disclosed for Compound 1. With regard to the presence of the other atropisomer or salt thereof in the composition, respectively, the considerations set out above for Compound 1 equally apply by analogy.

Solid Forms and Solvates

According to another aspect, the present invention provides solid forms of Compound 1 or 2, in particular of Compound 1.

It will be appreciated by one of ordinary skill in the art that the compounds according to the present invention can exist in a variety of physical forms. For example, they can be in solution, suspension, or in solid form.

In certain preferred embodiments, Compound 1 is in solid form. Solid forms are generally preferred herein because they allow for the provision of solid pharmaceutical compositions. When Compound 1 is in solid form, said compound may be amorphous, crystalline, or a mixture thereof. Exemplary solid forms of Compound 1 are described in more detail below.

According to one embodiment, the present invention provides Compound 1 as an amorphous solid. Amorphous solids are well known to one of ordinary skill in the art and are typically prepared by such methods as lyophilization, spray-drying or crash precipitation.

In other embodiments, Compound 1 is a crystalline solid. As used herein, the term "polymorph" refers to the different crystal structures in which a compound can crystallize.

In some embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 90% by weight of crystalline Compound 1 is present, or at least about 95% by weight of crystalline Compound 1 is present. In still other embodiments of the invention, at least about 99% by weight of crystalline Compound 1 is present. These percentages are relative to the absolute weight of Compound 1 (100 wt. %). The same applies, mutatis mutandis, to the acceptable amorphous content in any crystalline form respectively polymorph of all compounds disclosed herein, including those described for the salts, anhydrous forms, solvates and other forms herein.

According to one aspect, the present invention provides a solid form of Compound 1, which is a solid form of anhydrous Compound 1, preferably crystalline anhydrous Compound 1. Five different polymorphic forms of anhydrous Compound 1 are described herein. In the context of the specific solid forms described in this section involving anhydrous forms and solvates, reference to Compound 1 shall be understood as a reference to the compound as such, i.e. its free (non-salt) form.

A first anhydrous crystalline form of Compound 1 is in the following referred to as "Form A2" and is a polymorph characterized by a powder X-ray diffraction (XRPD) pattern substantially in line with that depicted in FIG. 13, and has been found to be highly advantageous.

According to one embodiment, Form A2 is characterized by one or more peaks in its powder X-ray diffraction pattern selected from those at about 7.3, about 9.6, about 11.1, about 12.0, about 12.7, and about 16.2 degrees 2-theta. In some embodiments, Form A2 is characterized by two or more peaks in its powder X-ray diffraction pattern selected from those at about 7.3, about 9.6, about 12.7, about 16.2, about 22.6 and about 25.1 degrees 2-theta. In certain embodiments, Form A2 is characterized by three or more peaks in its powder X-ray diffraction pattern selected from those at about 7.3, about 9.6, about 12.7, about 16.2, about 22.6 and about 25.1 degrees 2-theta. In certain embodiments, Form A2 is characterized by four, five or substantially all of the peaks in its powder X-ray diffraction pattern selected from those at about 7.3, about 9.6, about 12.7, about 16.2, about 22.6 and about 25.1 degrees 2-theta. In particular embodiments, Form A2 is characterized by six or more or substantially all of the peaks in its X-ray powder diffraction pattern selected from those at about 7.3, 9.6, 11.1, 12.0, 12.7, 14.7, 16.2, 17.3, 18.9, 21.0, 22.6 and 25.1 degrees 2-theta.

In an exemplary embodiment, Form A2 may be characterized by one or more, preferably six and up to substantially all of the peaks in its X-ray powder diffraction (XRPD) pattern selected from those at about:

| Form A2 | |
|---|---|
| Peak No. | °2-Theta |
| 1 | 7.3* |
| 2 | 9.6* |
| 3 | 11.1* |
| 4 | 12.0* |
| 5 | 12.7* |
| 6 | 13.0 |
| 7 | 14.7 |
| 8 | 16.2* |
| 9 | 16.9 |
| 10 | 17.3 |
| 11 | 18.9 |
| 12 | 19.3 |
| 13 | 19.7 |
| 14 | 20.4 |
| 15 | 21.0 |
| 16 | 21.8 |
| 17 | 22.1 |
| 18 | 22.4 |
| 19 | 22.6 |
| 20 | 23.4 |
| 21 | 25.1 |
| 22 | 25.7 |
| 23 | 26.4 |
| 24 | 28.0 |
| 25 | 28.3 |

It will be appreciated that the above-described polymorphic form can be characterized, for example, by reference to any of the peaks in its respective X-ray diffraction (XRD) pattern. As set out before, bold print and asterisks designate peaks that may be preferred for the characterisation of a polymorph.

Form A2 may be characterized by one, two, three, four, five, six, seven, eight, nine, ten, eleven, twelve, thirteen, fourteen, fifteen, sixteen, seventeen, eighteen, nineteen, twenty or more of the XRPD peaks (° 2e) of the above table. Any polymorph described herein is preferably characterized by at least six XRD or XRPD peaks (° 2e, preferably ±0.2).

Form A2 may optionally be characterized in that is has a monoclinic crystal system and a $P2_1$ space group. Form A2 may be further characterized by one or more of the following parameters of its unit cell, as set out in the following Table:

| Form A2 | |
|---|---|
| a | 7.457 Å |
| b | 15.982 Å |
| c | 18.246 Å |
| α | 90.0° |
| β | 90.0° |

| Form A2 | |
|---|---|
| γ | 90.0° |
| V | 2174.5 Å$^3$ |

Figure 22:
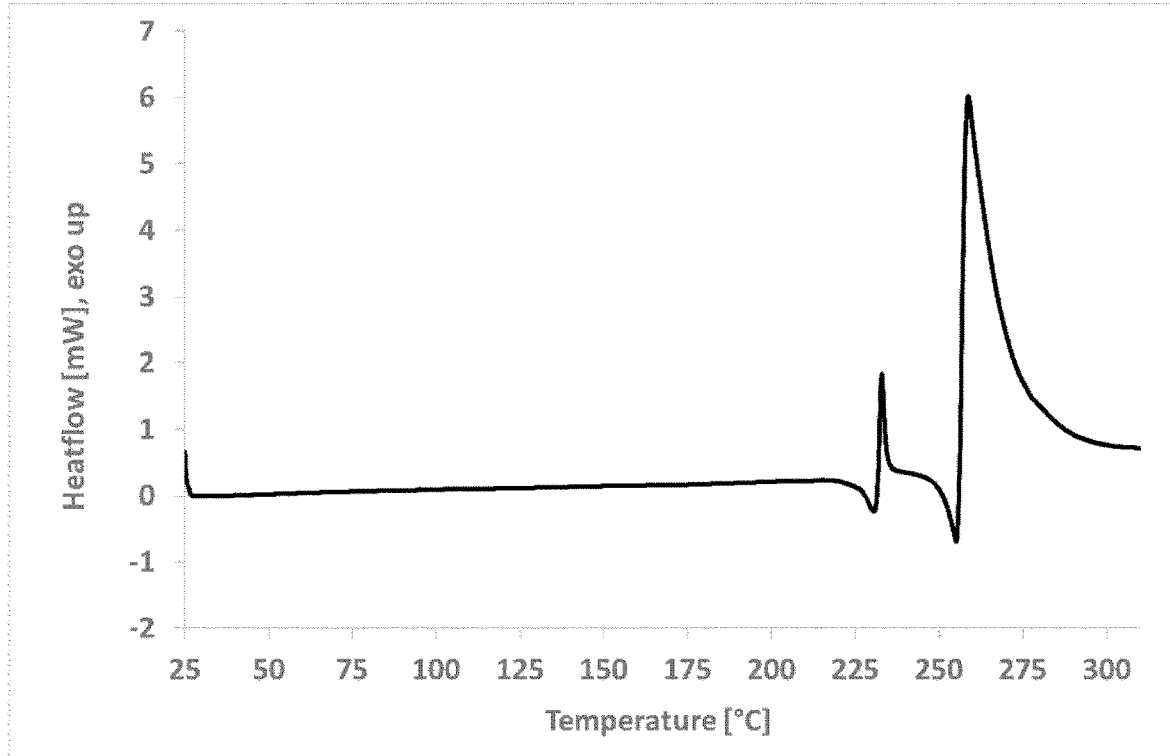
FIG. 22 shows a DSC heating curve of Form A2 of Compound 1.
Figure 23:
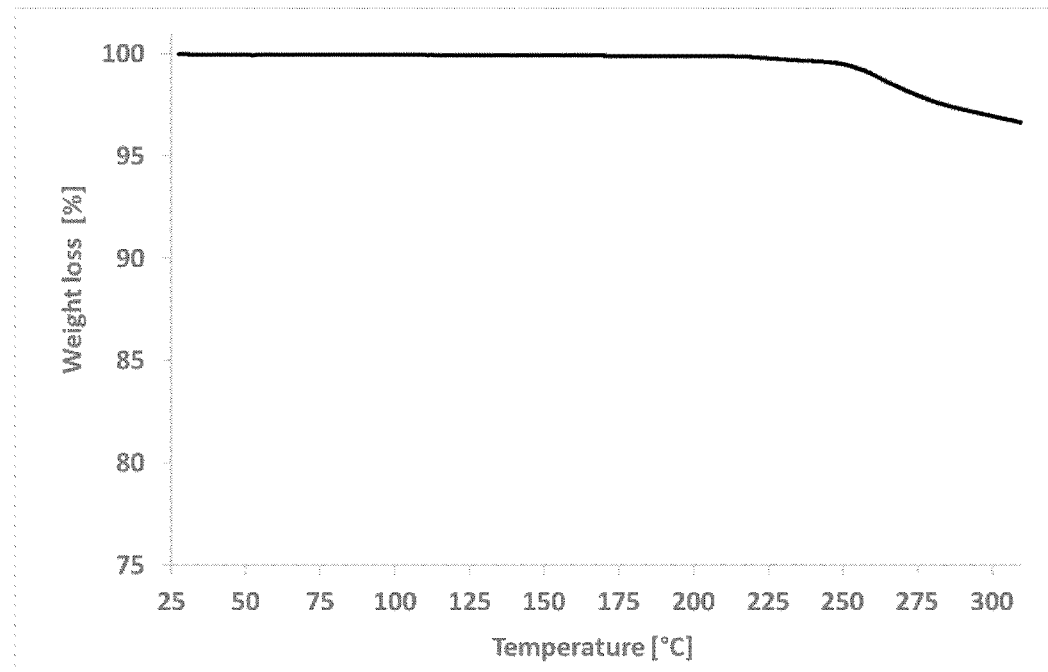
FIG. 23 shows a TGA heating curve of Form A2 of Compound 1.
Figure 24:
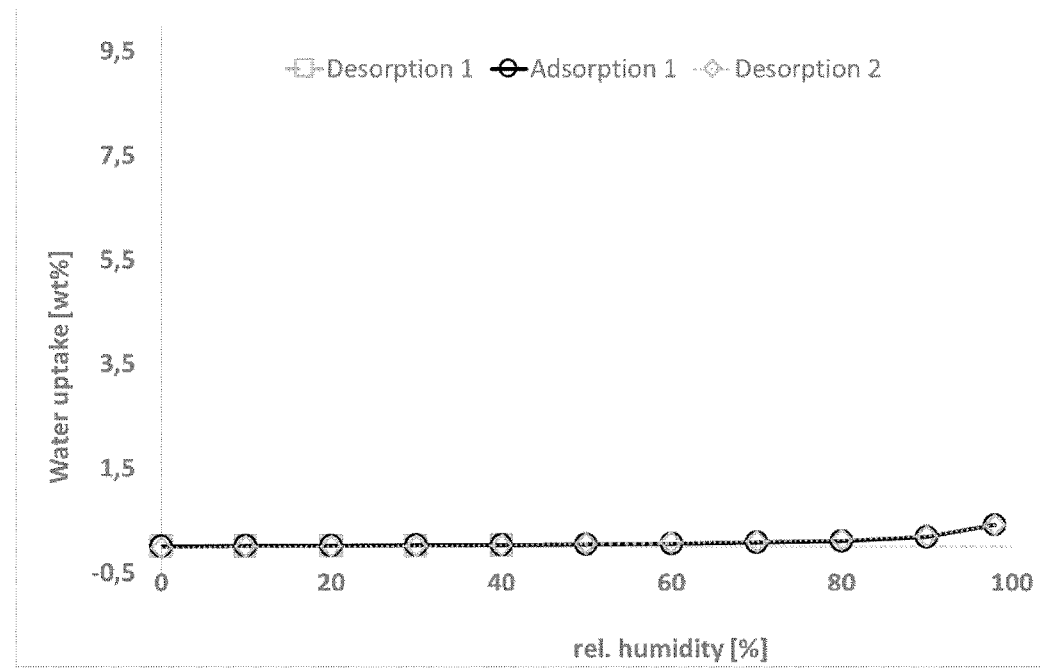
FIG. 24 shows a DVS water uptake isotherm (25° C.) of Form A2 of Compound 1.

Form A2 of Compound 1 has favourable overall properties, as further apparent from its thermal and water uptake behavior as illustrated by the DSC heating curve of (FIG. 22), the TGA heating curve (FIG. 23) and the DVS water uptake isotherm (at 25° C.) (FIG. 24). Form A2 adsorbs very little water (<2%) even up to a relative humidity of 100%, and is thus superior to Form A3, for instance.

Another advantage of Form A2 is its favourable dissolution behaviour, as illustrated in the following table, which represents the amounts of compound 1 in Form A2 dissolved in different time spans (non-sink dissolution data in FaSSIF at pH 6.5, method described in the Experimental Section):

| Time (min) | Dissolved Form A2 conc. |
|---|---|
| 5 | 163.4 µg/mL |
| 15 | 204.4 µg/mL |
| 30 | 233.2 µg/mL |
| 60 | 233.3 µg/mL |
| 120 | 224.0 µg/mL |

Form A2 can be obtained from Compound 1 by cooling crystallisation from alcohols, to name but one example. Suitable methods and reaction conditions are described in detail in EXAMPLE 7.

For instance, Form A2 crystals having favourable properties can be reproducibly prepared by a controlled crystallization process comprising:
a) Preparing a dispersion of Compound 1, for instance Compound 1 hydrate, such as Compound 1 hydrate form H2, in a suitable solvent, e.g. an alcohol,
b) Heating the dispersion to obtain a solution, preferably clear solution,
c) Controlled cooling the solution,
d) Adding seed crystals of Form A2,
e) Controlled cooling the solution with the seed crystals, for instance at a rate of about 0.1° C./min.

Suitable alcohols and crystallisation conditions, such as temperatures, can be derived from EXAMPLES 7.1 to 7.3, which are applicable beyond the specific embodiment. The present invention further pertains to anhydrous, crystalline Compound 1 in Form A2, which is obtainable by the above process or substantially in line with any of the processes described in EXAMPLES 7.1 to 7.4.

Figure 14:
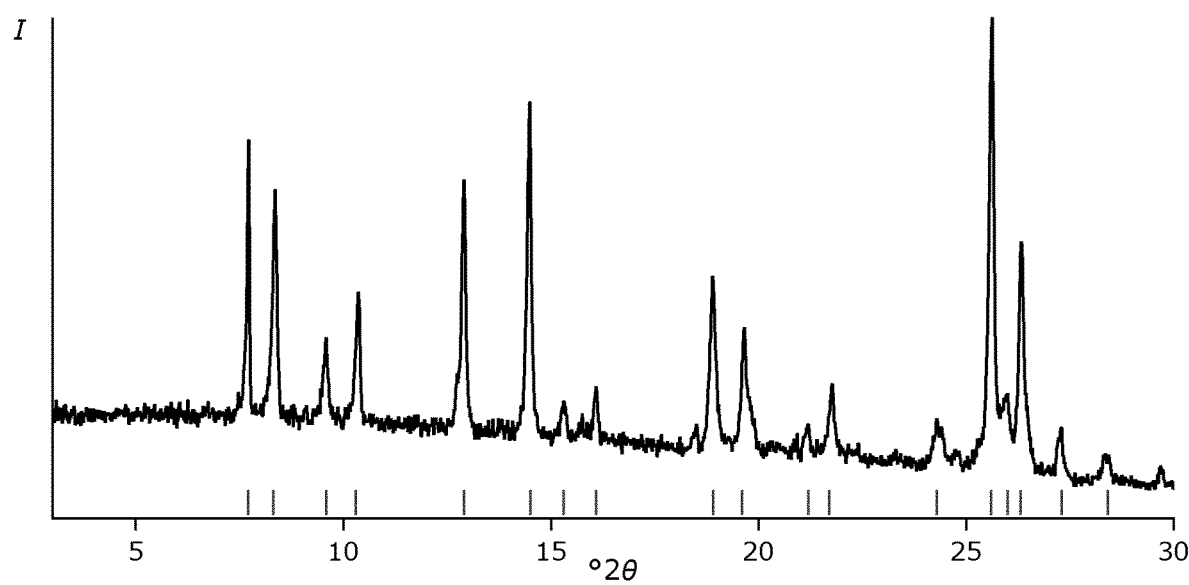
FIG. 14 depicts an X-ray powder diffraction (XRPD) pattern of solid Form A1 of Compound 1.

A further anhydrous crystalline form of Compound 1 is in the following referred to as "Form A1" and is a polymorph characterized by a powder X-ray diffraction pattern substantially in line with that depicted in FIG. 14. Suitable methods for its preparation are described in EXAMPLE 7.

Form A1 may be characterized by one or more, preferably six, and up to substantially all of the peaks in its X-ray powder diffraction pattern selected from those at about:

| Form A1 | |
|---|---|
| Peak No. | °2-Theta |
| 1 | 7.7* |
| 2 | 8.3* |
| 3 | 9.6 |

-continued

| Form A1 | |
|---|---|
| Peak No. | °2-Theta |
| 4 | 10.3* |
| 5 | 12.9* |
| 6 | 14.5* |
| 7 | 15.3 |
| 8 | 16.1 |
| 9 | 18.9* |
| 10 | 19.6 |
| 11 | 21.2 |
| 12 | 21.7 |
| 13 | 24.3 |
| 14 | 25.6* |
| 15 | 26 |
| 16 | 26.3 |
| 17 | 27.3 |

Figure 25:
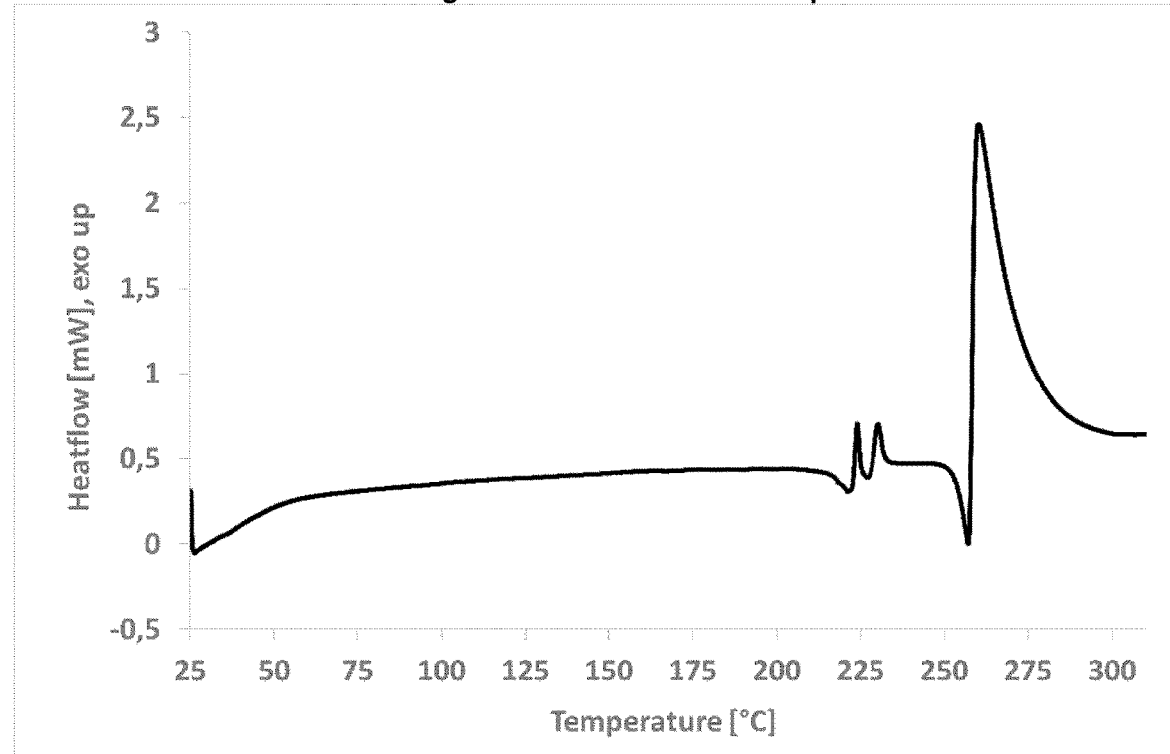
FIG. 25 shows a DSC heating curve of Form A1 of Compound 1.
Figure 26:
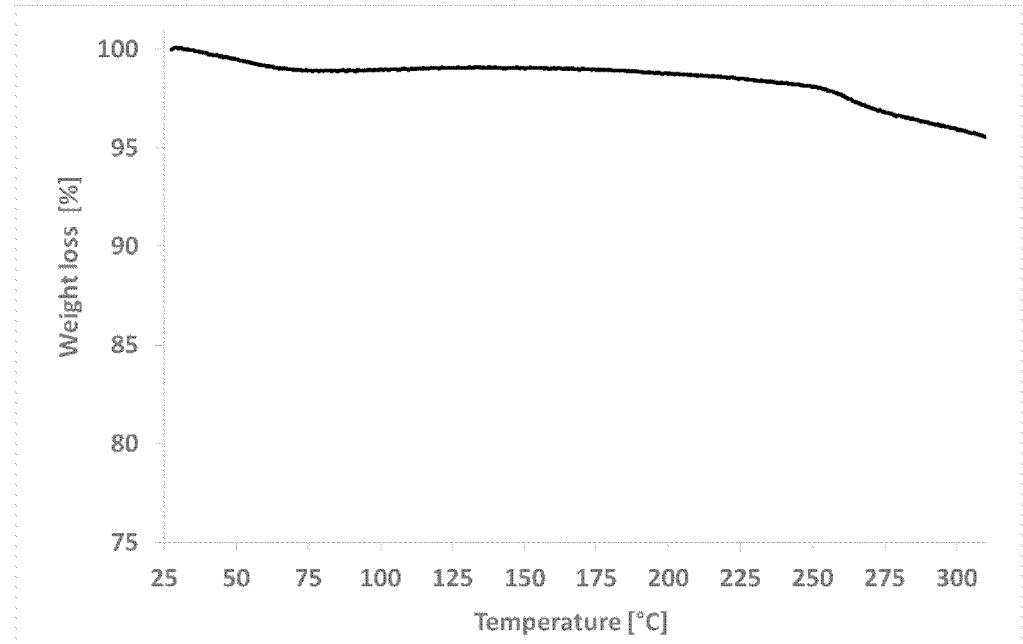
FIG. 26 depicts a TGA heating curve of Form A1 of Compound 1.

Thermal properties of Form A1 of compound 1 were evaluated by differential scanning calorimetry (DSC) and thermogravimetric analysis (TGA), as illustrated in FIGS. 25 and 26.

Figure 15:
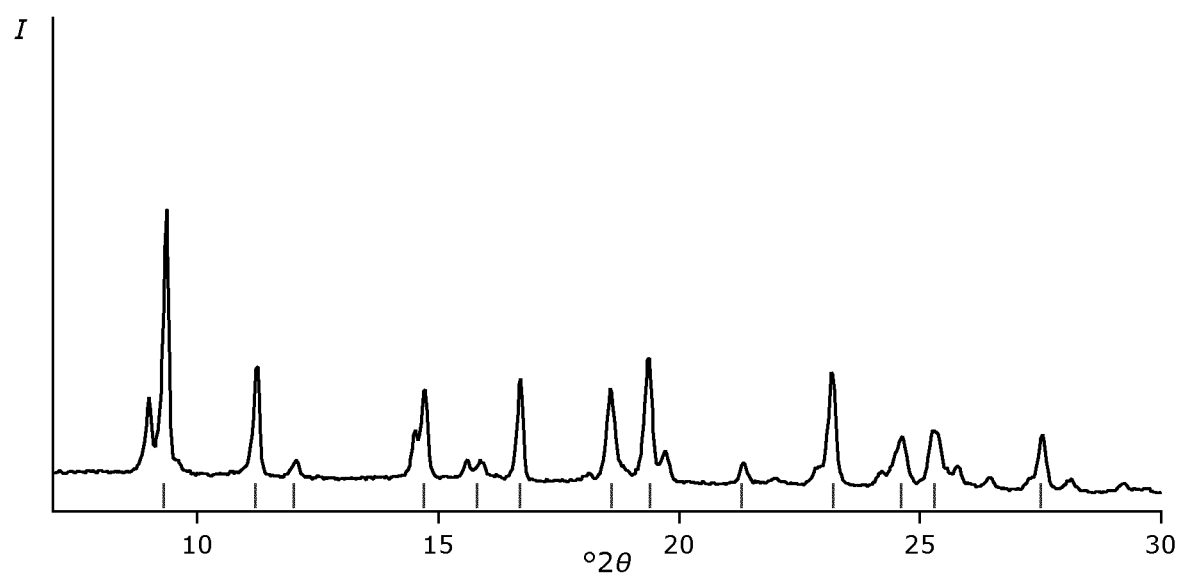
FIG. 15 depicts an X-ray powder diffraction (XRPD) pattern of solid Form A3 of Compound 1.

A third anhydrous crystalline form of Compound 1 is in the following referred to as "Form A3" and is a polymorph characterized by a powder X-ray diffraction pattern substantially in line with that depicted in FIG. 15. A suitable method for its preparation is described in EXAMPLE 7.

Form A3 may be characterized by one or more, preferably six, and up to substantially all of the peaks in its X-ray powder diffraction pattern selected from those at about:

| Form A3 | |
|---|---|
| Peak No. | °2-Theta |
| 1 | 9.3* |
| 2 | 11.2 |
| 3 | 12 |
| 4 | 14.7* |
| 5 | 15.8 |
| 6 | 16.7* |
| 7 | 18.6* |
| 8 | 19.4* |
| 9 | 21.3 |
| 10 | 23.2* |
| 11 | 24.6 |
| 12 | 25.3 |
| 13 | 27.5 |

Figure 27:
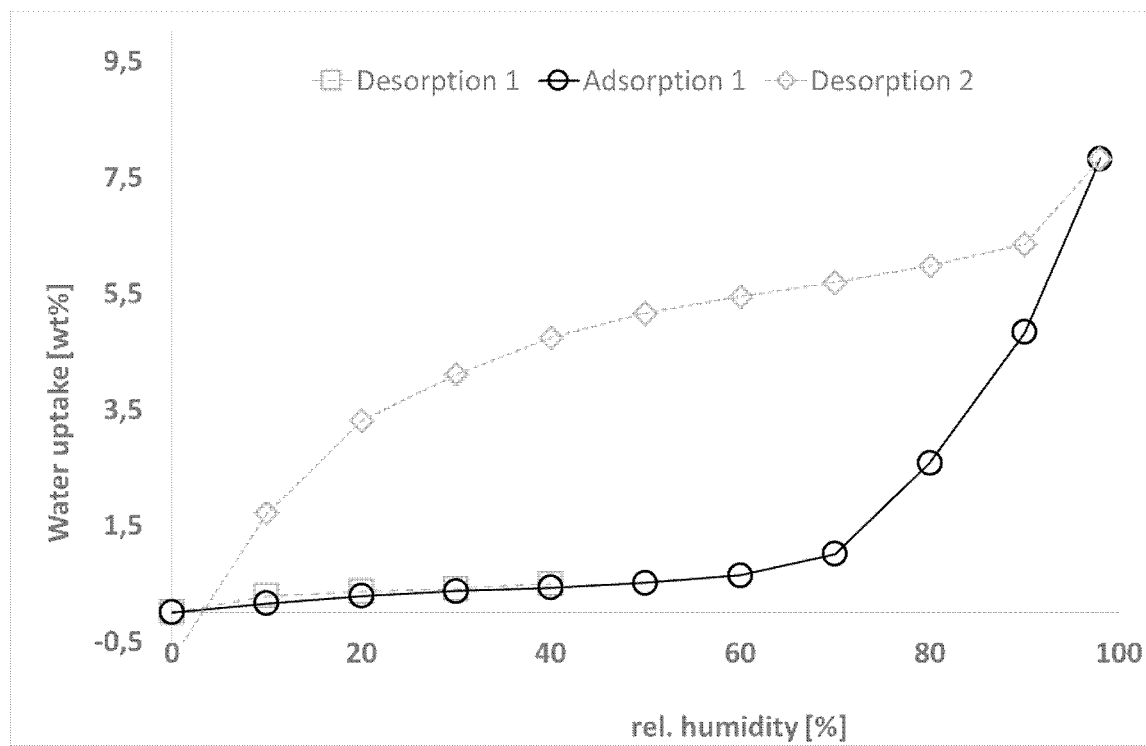
FIG. 27 shows a DVS water uptake isotherm (25° C.) of Form A3 of Compound 1.

As apparent from FIG. 27, Form A3 of Compound 1 shows very little water adsorption up to a relative humidity of about 70%. Form A3 may optionally be further characterized by the crystal system and unit cell parameters as set out in Table 7 below. Non-sink dissolution data in FaSSIF at pH 6.5 of Compound 1 in Form A3 are given in the table below:

| Time (min) | Dissolved Form A3 conc. |
|---|---|
| 5 | 135.6 µg/mL |
| 15 | 160.8 µg/mL |
| 30 | 190.3 µg/mL |
| 60 | 212.9 µg/mL |
| 120 | 219.7 µg/mL |

Figure 16:
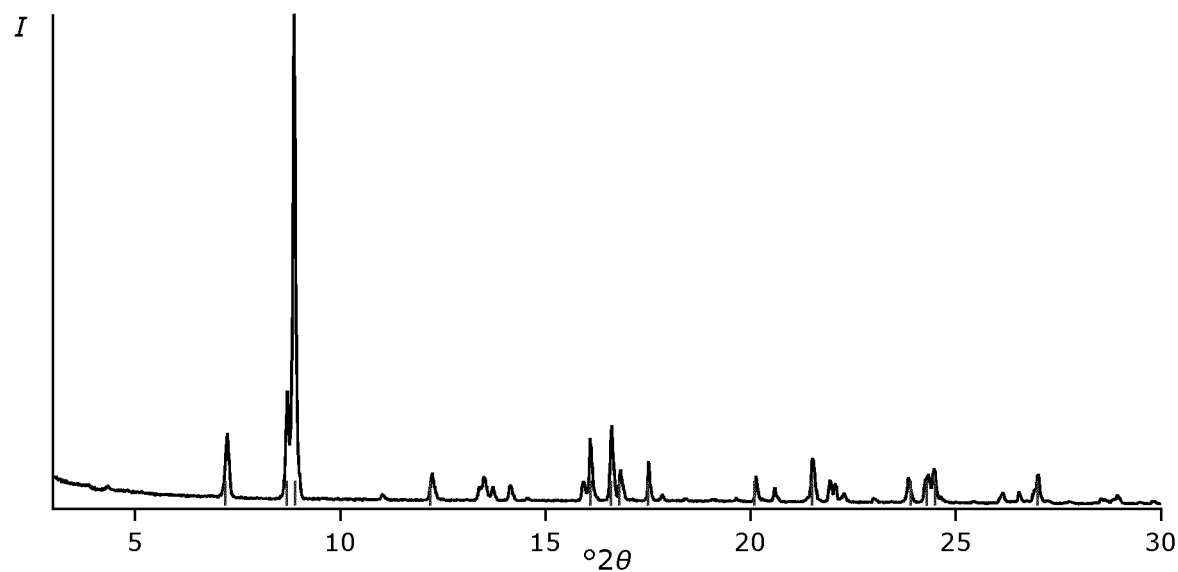
FIG. 16 depicts an X-ray powder diffraction (XRPD) pattern of solid Form NF9 of Compound 1.

A fourth anhydrous crystalline form of Compound 1 is in the following referred to as "Form NF9" and is a polymorph characterized by a powder X-ray diffraction pattern substantially in line with that depicted in FIG. 16. A suitable method for its preparation is described in EXAMPLE 7.

Form NF9 may be characterized by one or more, preferably six and up to substantially all of the peaks in its X-ray powder diffraction pattern selected from those at about:

| Form NF9 | |
|---|---|
| Peak No. | °2-Theta |
| 1 | 7.2* |
| 2 | 8.7* |
| 3 | 8.9* |
| 4 | 12.2 |
| 5 | 16.1* |
| 6 | 16.6* |
| 7 | 16.8 |
| 8 | 17.5 |
| 9 | 20.1 |
| 10 | 21.5* |
| 11 | 23.9 |
| 12 | 24.3 |
| 13 | 24.5 |
| 14 | 27 |

In a further embodiment, the present invention provides hydrates of Compound 1, preferably a solid form of Compound 1 hydrate, preferably crystalline Compound 1 hydrate. Two different hydrates respectively polymorphic forms of Compound 1 hydrates are described herein. As mentioned above, in the context of these specific solid forms, reference to Compound 1 shall be understood as a reference to the compound as such, i.e. its free (non-salt) form.

Figure 17:
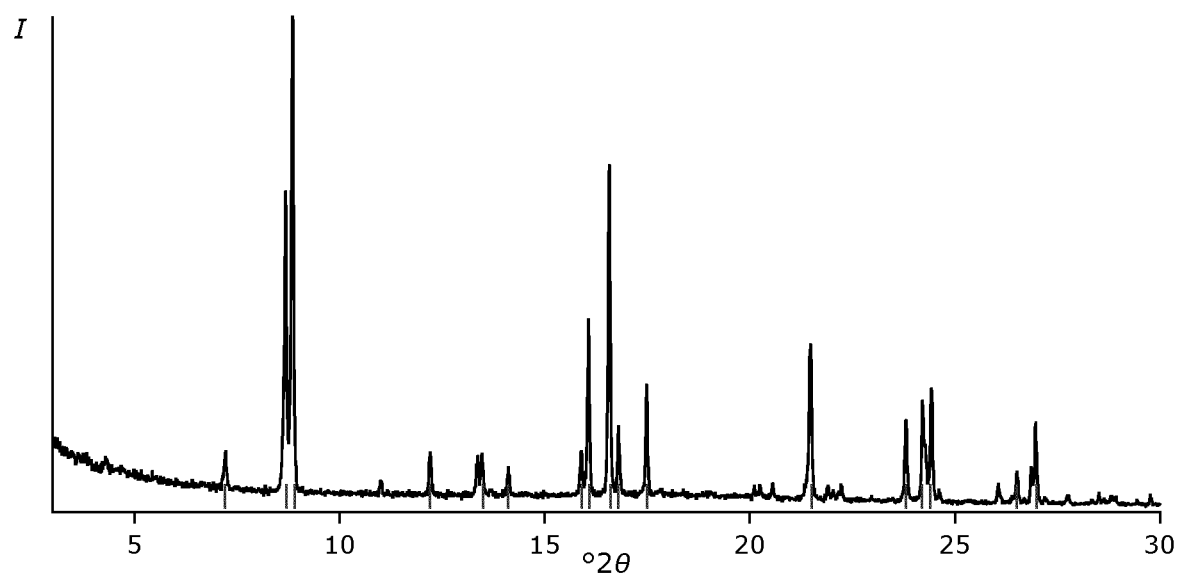
FIG. 17 depicts an X-ray powder diffraction (XRPD) pattern of solid Form H1 of Compound 1 hydrate.

A first crystalline form of a Compound 1 hydrate is in the following referred to as "Form H1" and is a polymorph characterized by a powder X-ray diffraction pattern substantially in line with that depicted in FIG. 17. Suitable methods for its preparation are described in EXAMPLE 7.

Form H1 may be characterized by one or more, preferably six and up to substantially all of the peaks in its X-ray powder diffraction pattern selected from those at about:

| Form H1 | |
|---|---|
| Peak No. | °2-Theta |
| 1 | 7.2* |
| 2 | 8.7* |
| 3 | 8.9* |
| 4 | 12.2 |
| 5 | 13.5 |
| 6 | 14.1 |
| 7 | 15.9 |
| 8 | 16.1* |
| 9 | 16.6* |
| 10 | 16.8 |
| 11 | 17.5 |
| 12 | 21.5* |
| 13 | 23.8 |
| 14 | 24.2 |
| 15 | 24.4 |
| 16 | 26.5 |
| 17 | 27 |

Figure 18:
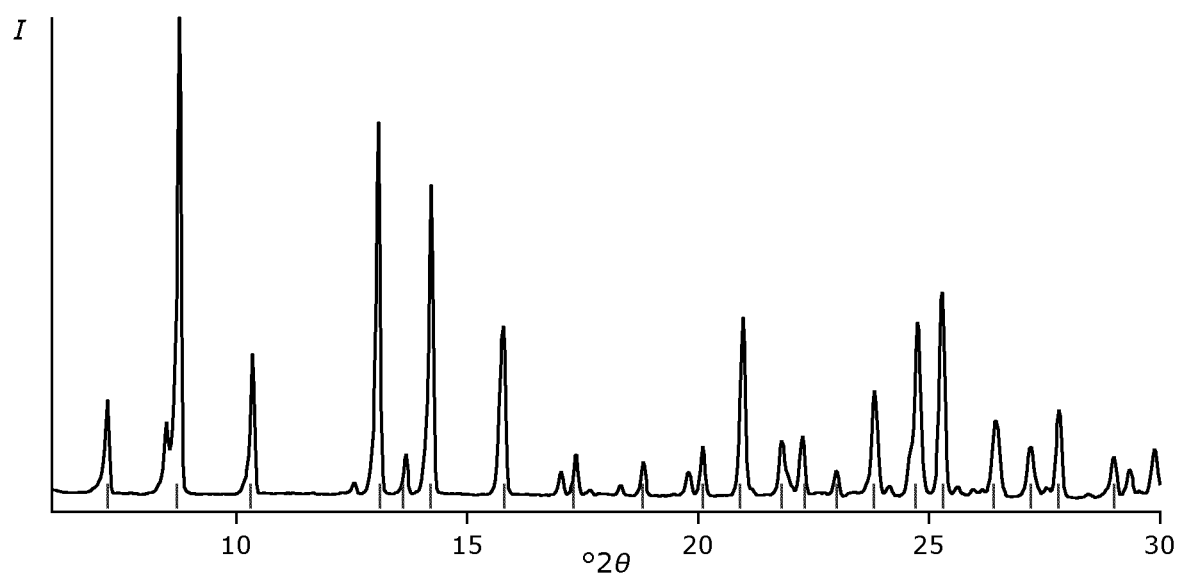
FIG. 18 depicts an X-ray powder diffraction (XRPD) pattern of solid Form H2 of Compound 1 hydrate

A second crystalline form of a Compound 1 hydrate is in the following referred to as "Form H2" and is a polymorph characterized by a powder X-ray diffraction pattern substantially in line with that depicted in FIG. 18. Suitable methods for its preparation are described in EXAMPLE 7.

Form H2 may be characterized by one or more, preferably six and up to substantially all of the peaks in its X-ray powder diffraction pattern selected from those at about:

| Form H2 | |
| --- | --- |
| Peak No. | °2-Theta |
| 1 | 7.2* |
| 2 | 8.7* |
| 3 | 10.3* |
| 4 | 13.1* |
| 5 | 13.6 |
| 6 | 14.2* |
| 7 | 15.8* |
| 8 | 17.3 |
| 9 | 18.8 |
| 10 | 20.1 |
| 11 | 20.9* |
| 12 | 21.8 |
| 13 | 22.3 |
| 14 | 23 |
| 15 | 23.8 |
| 16 | 24.7 |
| 17 | 25.3 |
| 18 | 26.4 |
| 19 | 27.2 |
| 20 | 27.8 |
| 21 | 29 |

Compound 1 hydrate in crystalline Form H2 may optionally be characterized in that is has a triclinic crystal system and a P1 space group. Form H2 may be characterized by one or more of the following parameters of its unit cell, as set out in Table 7 below.

Figure 28:
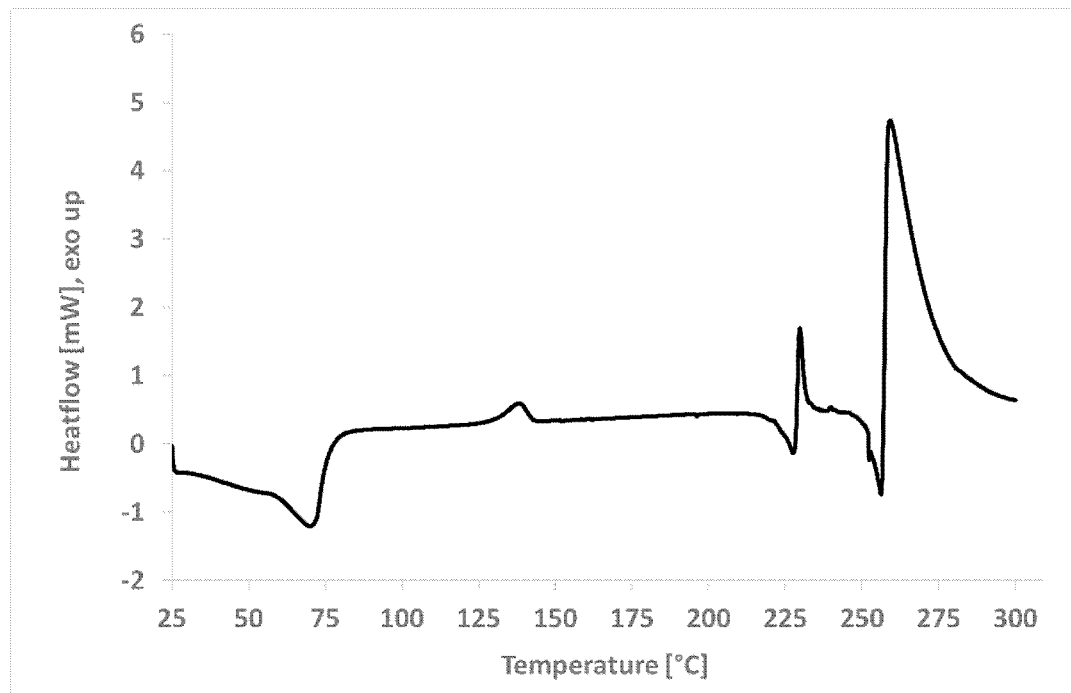
FIG. 28 depicts a DSC heating curve of Form H2 of Compound 1 (hydrate).
Figure 29:
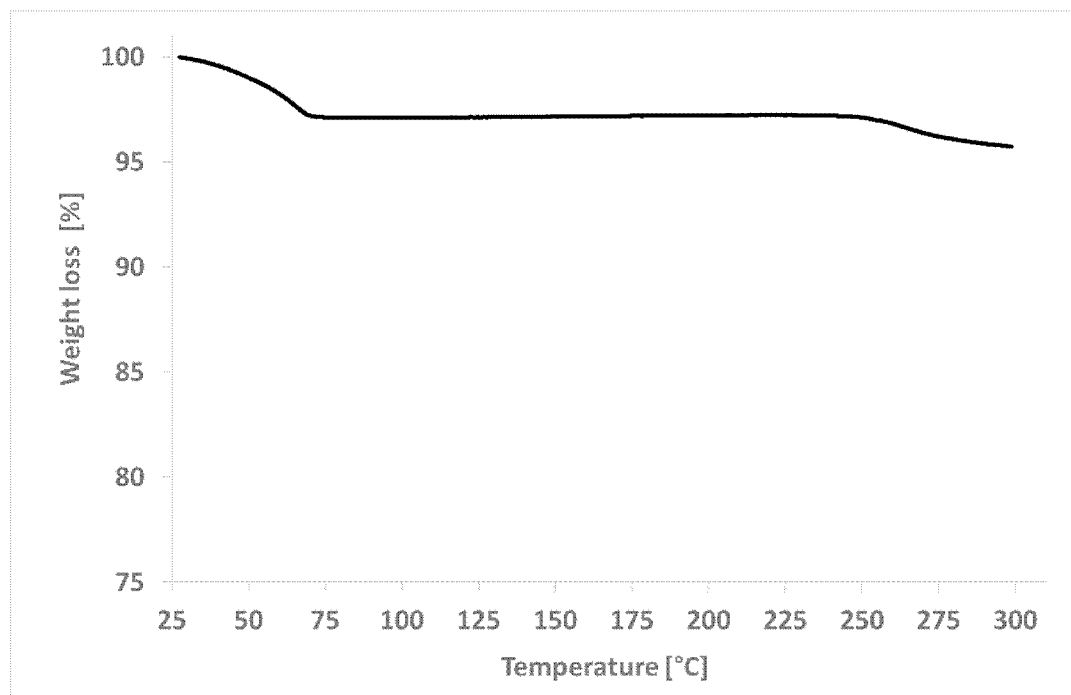
FIG. 29 shows aTGA heating curve of Form H2 of Compound 1 (hydrate).
Figure 30:
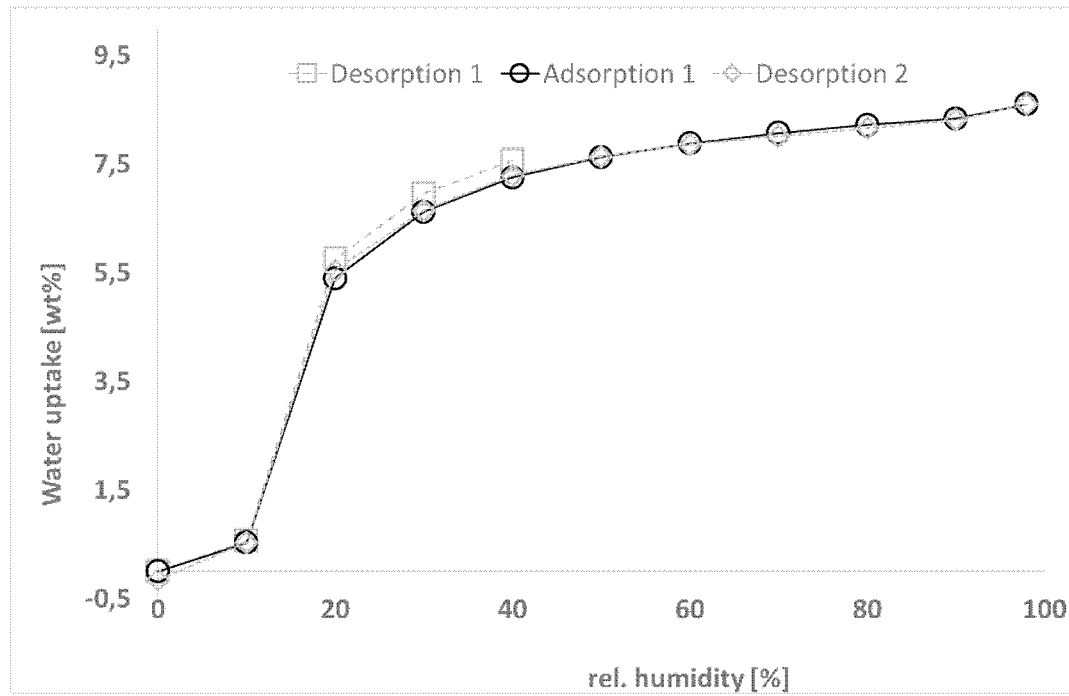
FIG. 30 shows a DVS water uptake isotherm (25° C.) of Form H2 of Compound 1 (hydrate).

Thermal and water adsorption properties of Form H2 are illustrated by FIGS. 28, 29 and 30. The non-sink dissolution data in FaSSIF (ph 6.5) for Form H2 of Compound 1 were determined to be as follows:

| Time (min) | Dissolved Fom H2 conc. |
| --- | --- |
| 5 | 42.7 µg/mL |
| 15 | 78.8 µg/mL |
| 30 | 140.8 µg/mL |
| 60 | 200.5 µg/mL |
| 120 | 218.3 µg/mL |

Figure 19:
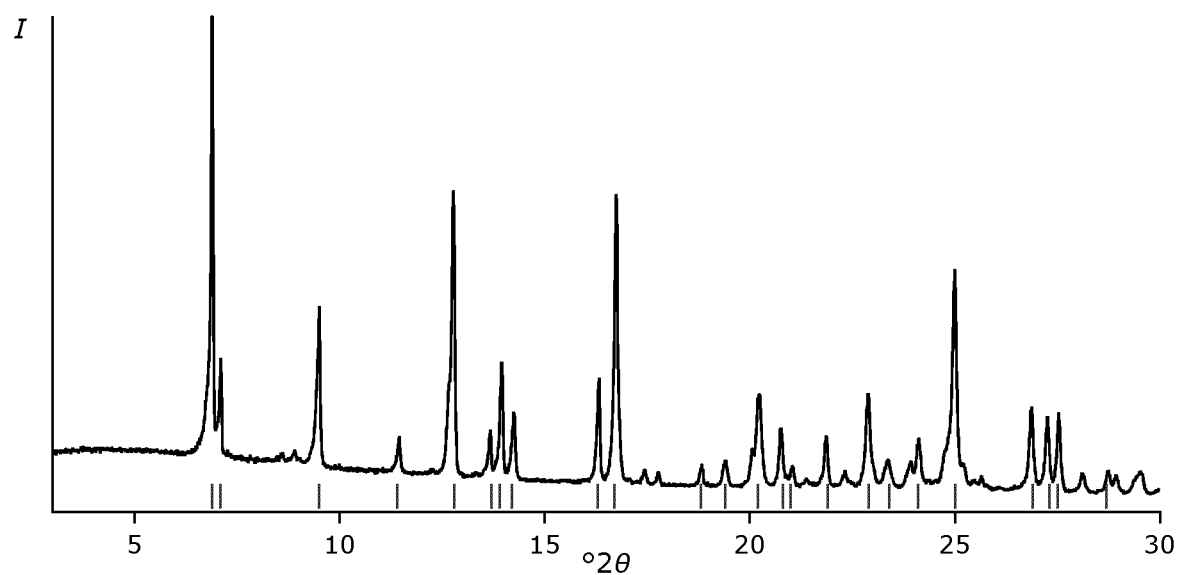
FIG. 19 depicts an X-ray powder diffraction (XRPD) pattern of solid Form NF19 of Compound 1.

A fifth crystalline form of anhydrous Compound 1 is in the following referred to as "Form NF19" and is a polymorph characterized by a powder X-ray diffraction pattern substantially in line with that depicted in FIG. 19. Suitable methods for its preparation are described in EXAMPLE 7.

Form NF19 may be characterized by one or more, preferably six and up to substantially all of the peaks in its X-ray powder diffraction pattern selected from those at about:

| Form NF19 | |
| --- | --- |
| Peak No. | °2-Theta |
| 1 | 6.9 |
| 2 | 7.1 |
| 3 | 9.5 |
| 4 | 11.4 |
| 5 | 12.8 |
| 6 | 13.7 |
| 7 | 13.9 |
| 8 | 14.2 |
| 9 | 16.3 |
| 10 | 16.7 |
| 11 | 18.8 |
| 12 | 19.4 |
| 13 | 20.2 |
| 14 | 20.8 |
| 15 | 21 |
| 16 | 21.9 |
| 17 | 22.9 |
| 18 | 23.4 |
| 19 | 24.1 |
| 20 | 25 |
| 21 | 26.9 |
| 22 | 27.3 |
| 23 | 27.5 |
| 24 | 28.7 |

Solid forms A1, A3, H1 and H2 may also, or in the alternative, be characterized by having a certain crystal system, space group and/or unit cell parameter selected from a, b, c, $\alpha$, $\beta$, $\gamma$, and V, as set out below in Table 7:

TABLE 7

| Measurement temp.<br>Crystal system<br>Space group | Form A1<br>298 K<br>triclinic<br>P1 | Form A3<br>298 K<br>triclinic<br>P1 | Form H1<br>298 K<br>monoclinic<br>P2$_1$ | Form H2<br>200 K<br>triclinic<br>P1 |
| --- | --- | --- | --- | --- |
| a | 8.940 Å | 10.553 Å | 13.206 Å | 8.542 Å |
| b | 11.022 Å | 10.984 Å | 8.697 Å | 11.249 Å |
| c | 12.509 Å | 11.530 Å | 20.791 Å | 13.150 Å |
| $\alpha$ | 106.1° | 112.8° | 90.0° | 67.3° |
| $\beta$ | 107.4° | 112.8° | 102.8° | 89.8° |
| $\gamma$ | 90.1° | 93.7° | 90.0° | 83.3° |
| V | 1125.7 Å$^3$ | 1099.2 Å$^3$ | 2328.0 Å$^3$ | 1156.6 Å$^3$ |

The present invention also pertains to the following solvate forms, which can be readily made by crystallisation from the respective solvents, but have been found to be considerably less advantageous with regard to important properties as compared to the above forms: A methanolate of Compound 1 (solid form referred to as S1), a mixed hydrate/methanolate of Compound 1 (solid form referred to as S2), a THF solvate of Compound 1 (solid form referred to as S3), 1,4-dioxane solvate forms of Compound 1 in numerous solid forms (solid forms referred to as NF11 [from slurry conversion experiment of anhydrous form at ~26 mg/200 µL in 1,4-dioxane at RT], NF29 [from cooling crystallization experiment 50-5° C. in 1,4-dioxane], NF36 [from slurry conversion experiment of anhydrous form at ~52 mg/150 µL in 1,4-dioxane at RT]), a chloroform solvate of Compound 1 (solid form referred to as NF15), acetic acid solvate forms of Compound 1 in various solid forms (solid forms referred to as NF16 [from evaporation crystallization experiment at RT in acetic acid], NF18 [from evaporation crystallization experiment at 50° C. in acetic acid]), a dichloromethane (DCM) solvate of Compound 1 (solid form referred to as NF32), a NMP (N-Methyl-2-pyrrolidone) solvate of Compound 1 (solid form referred to as NF33), an acetonitrile solvate of Compound 1 (solid form referred to as NF35), a dimethylacetamide (DMAA) solvate of Compound 1 (solid form referred to as NF37). XRPDs of solid forms of these solvates are shown in FIGS. 40 to 52, the corresponding peaks being listed in the following tables:

| Peak | 2 θ | | | | | | | |
| --- | --- | --- | --- | --- | --- | --- | --- | --- |
| # | S1 | S2 | S3 | NF11 | NF15 | NF16 | NF18 | NF29 |
| 1 | 7.2 | 8.3 | 7.5 | 7.9 | 7.9 | 6.8 | 6.8 | 7.9 |
| 2 | 8.7 | 9.8 | 8.0 | 8.1 | 9.4 | 8.5 | 6.9 | 9.6 |
| 3 | 12.5 | 10.2 | 10.3 | 8.6 | 9.6 | 8.7 | 8.5 | 10.7 |

-continued

| | | | | | | | | |
|---|---|---|---|---|---|---|---|---|
| 4 | 13.6 | 12.6 | 14.6 | 10.3 | 10.8 | 11.9 | 8.7 | 10.9 |
| 5 | 14.2 | 13.5 | 15.0 | 11.7 | 11.5 | 14.7 | 9.4 | 13.5 |
| 6 | 15.5 | 14.1 | 15.4 | 12.1 | 12.4 | 15.4 | 11.9 | 13.7 |
| 7 | 15.9 | 14.9 | 18.7 | 12.3 | 12.8 | 16.4 | 14.7 | 14.5 |
| 8 | 16.4 | 16.8 | 21.4 | 13.1 | 14.2 | 17.0 | 15.4 | 15.3 |
| 9 | 16.8 | 19.0 | 22.0 | 16.5 | 14.6 | 17.8 | 16.4 | 15.8 |
| 10 | 19.9 | 20.5 | 22.6 | 16.7 | 15.2 | 18.4 | 17.8 | 16.2 |
| 11 | 20.7 | 21.0 | 23.6 | 16.9 | 15.7 | 18.9 | 18.4 | 17.5 |
| 12 | 21.6 | 22.2 | 29.6 | 19.6 | 16.6 | 20.0 | 18.9 | 17.9 |
| 13 | 23.2 | 24.2 | | 20.1 | 19.3 | 20.4 | 20.0 | 19.3 |
| 14 | 23.5 | 24.8 | | 20.6 | 20.4 | 23.3 | 20.4 | 21.4 |
| 15 | 24.2 | 25.8 | | 21.1 | 21.6 | 24.7 | 23.3 | 22.0 |
| 16 | 24.6 | 26.2 | | 21.8 | 22.9 | 25.0 | 24.7 | 22.4 |
| 17 | 25.0 | 26.5 | | 23.8 | 24.1 | 25.7 | 25.0 | 23.2 |
| 18 | 25.8 | 27.2 | | 24.3 | 24.6 | 26.5 | 25.7 | 23.5 |
| 19 | 27.1 | 27.6 | | 24.8 | 26.6 | 27.2 | 26.5 | 24.8 |
| 20 | 28.8 | 28.4 | | 27.5 | 28.3 | 28.4 | 27.2 | 25.4 |

| Peak | 2 θ | | | | |
|---|---|---|---|---|---|
| # | NF32 | NF33 | NF35 | NF36 | NF37 |
| 1 | 7.2 | 7.6 | 7.0 | 7.9 | 7.4 |
| 2 | 8.9 | 13.4 | 8.4 | 9.6 | 9.7 |
| 3 | 9.4 | 13.8 | 9.3 | 10.7 | 11.2 |
| 4 | 10.0 | 16.3 | 10.3 | 10.9 | 12.1 |
| 5 | 10.7 | 17.2 | 12.5 | 13.7 | 12.8 |
| 6 | 11.6 | 17.8 | 12.8 | 14.5 | 13.1 |
| 7 | 13.4 | 21.5 | 13.6 | 15.4 | 14.7 |
| 8 | 14.4 | 21.9 | 14.0 | 15.8 | 16.3 |
| 9 | 14.8 | 22.7 | 14.3 | 16.2 | 17.3 |
| 10 | 16.7 | 23.5 | 15.3 | 17.9 | 18.7 |
| 11 | 18.9 | 24.3 | 16.4 | 19.2 | 18.9 |
| 12 | 21.5 | 25.2 | 16.9 | 22.0 | 20.5 |
| 13 | 21.7 | 27.4 | 19.0 | 22.4 | 21.0 |
| 14 | 22.1 | | 20.0 | 22.9 | 22.4 |
| 15 | 23.2 | | 20.2 | 23.2 | 22.7 |
| 16 | 24.6 | | 21.0 | 23.5 | 23.4 |
| 17 | 25.5 | | 24.4 | 24.9 | 25.2 |
| 18 | 26.6 | | 25.6 | 25.4 | 25.3 |
| 19 | 27.1 | | 26.5 | | 25.7 |
| 20 | 28.4 | | 27.5 | | 28.1 |

According to another embodiment, the present invention provides a pharmaceutical composition that comprises an effective amount of Compound 1 in Form A2, which is the preferred solid form. According to another embodiment, the present invention provides a method of preparing such pharmaceutical compositions described herein, for example, a pharmaceutical composition that includes an effective amount of Compound 1 in Form A2. Still another embodiment provides a method of treating cancer using a pharmaceutical composition containing an effective amount of Compound 1 in Form A2 as described herein. According to another embodiment, the present invention provides the use of a Compound 1 in Form A2 in the manufacture of a medicament for treating cancer. In a further embodiment, the present invention provides Form A2 for use as a medicament, preferably for the treatment of cancer. In harmony with what has been set out above, exemplary embodiments, ranges, purities etc. disclosed for Compound 1 are equally valid for Form A2.

According to another embodiment, the present invention provides a pharmaceutical composition that comprises an effective amount of Compound 1 in any one of the solid forms of anhydrous Compound 1 or Compound 1 hydrate as described above. According to another embodiment, the present invention provides a method of preparing such pharmaceutical compositions described herein, for example, a pharmaceutical composition that includes an effective amount of Compound 1 in one of those solid forms. Still another embodiment provides a method of treating cancer using a pharmaceutical composition containing an effective amount of Compound 1 in one of the solid forms as described herein. According to another embodiment, the present invention provides the use of a Compound 1 in a solid form as described herein in the manufacture of a medicament for treating cancer. In a further embodiment, the present invention provides a solid form of Compound 1 as described herein for use as a medicament, preferably for the treatment of cancer. In harmony with what has been set out above, exemplary embodiments, ranges, purities etc. disclosed for Compound 1 are equally valid for the solid forms.

The present invention also concerns a solid form of anhydrous Compound 1 or Compound 1 hydrate, as described herein, which is obtained or obtainable according to a method described in EXAMPLE 7.

Deuterated Embodiments

According to a further aspect, the present invention provides deuterated derivatives of compound Y. According to one embodiment, the present invention provides:

8-(1,3-dimethylpyrazol-4-yl)-1-[3-fluoro-5-(trideuteriomethoxy)-4-pyridyl]-7-methoxy-3-(trideuterio-methyl) imidazo[4,5-c]quinolin-2-one (Compound 3) and 1-[3-fluoro-5-(trideuteriomethoxy)-4-pyridyl]-7-methoxy-3-methyl-8-[3-methyl-(trideuterio-methyl)pyrazol-4-yl] imidazo[4,5-c]quinolin-2-one (Compound 4).

8-(1,3-dimethylpyrazol-4-yl)-1-[3-fluoro-5-(trideuteriomethoxy)-4-pyridyl]-7-methoxy-3-methyl-imidazo[4,5-c]quinolin-2-one (Compound 5), as well as salts thereof.

Compounds 3, 4 and 5 are represented by the following formulae:

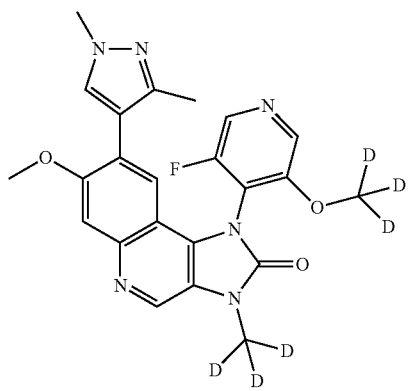

Compound 3

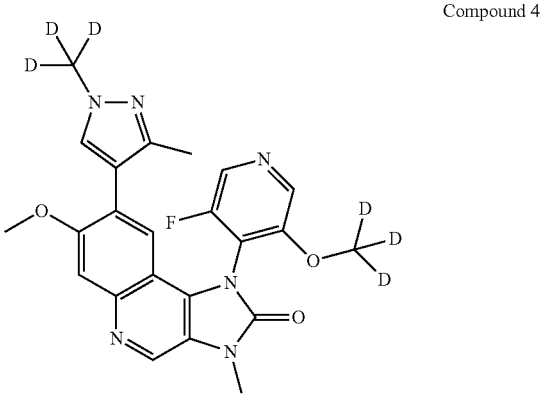

Compound 4

Compound 5

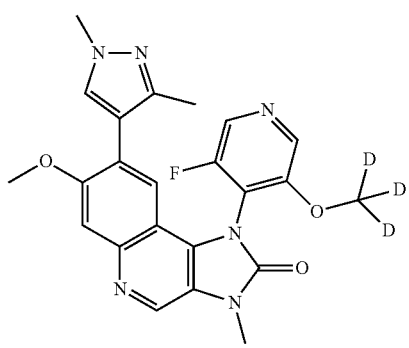

In other embodiments, the present invention provides the atropisomers 3-a, 3-b, 4-a, 4-b, 5-a, and 5-b:

Compound 3-a

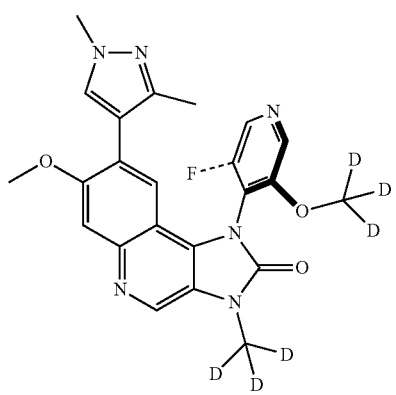

Compound 3-b

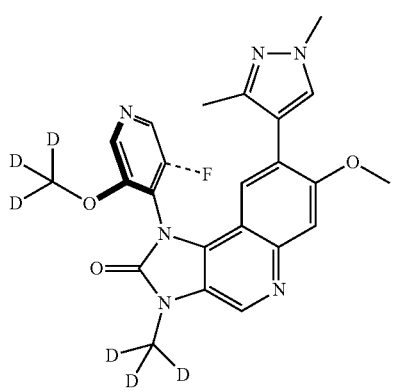

Compound 4-a

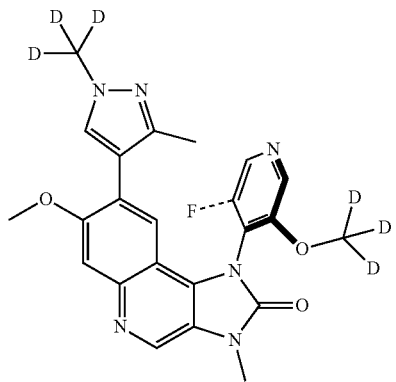

Compound 4-b

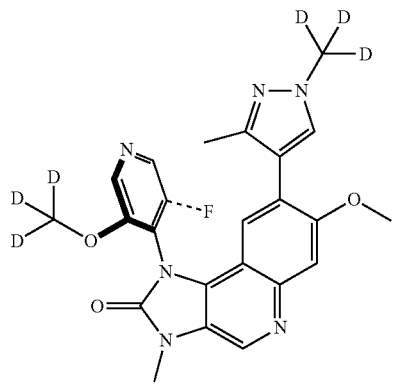

Compound 5-a

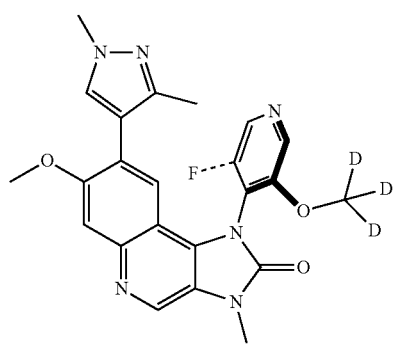

Compound 5-b

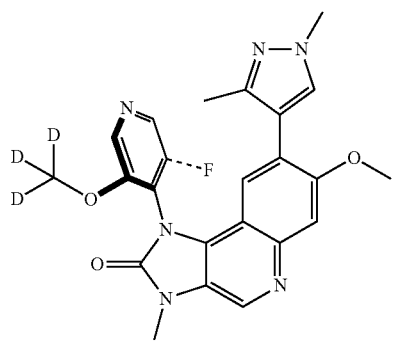

or salts thereof.

In harmony with what has been set out above with regard to Compounds 1 and 2, the present invention provides Compound 4-a, 5-a, 6-a, 4-b, 5-b, 6-b substantially free of the respective other atropisomer including any salt thereof. In further embodiments, these compounds are also provided substantially free of impurities. According to another embodiment, these compounds contain no more than about 5.0 area percent HPLC of total organic impurities relative to the total area of the HPLC chromatogram. Exemplary and preferred ranges disclosed above for Compound 1 in connection with "substantially free of Compound 2 or salt thereof", "free of impurities" and area percent of total organic impurities are, by analogy, equally applicable here in relation to the corresponding other atropisomers of the respective compound.

According to another embodiment, the present invention provides a pharmaceutical composition that comprises an effective amount of at least one of Compounds 3, 4 or 5, atropisomer or pharmaceutically acceptable salt thereof. According to another embodiment, the present invention provides a method of preparing such pharmaceutical compositions described herein. Still another embodiment provides a method of treating cancer using a pharmaceutical composition described herein. According to another embodiment, the present invention provides the use of a composition described herein in the manufacture of a medicament for treating cancer. Exemplary and preferred embodiments as disclosed above for Compound 1 are equally applicable to these compounds.

Preparation

Compounds 1 and 2 according to the present invention can be prepared starting from Compound Y, which compound has been previously described. As disclosed in WO 2016/155884, 8-(1,3-Dimethyl-1H-pyrazol-4-yl)-1-(3-fluoro-5-methoxypyridin-4-yl)-7-methoxy-3-methyl-1,3-dihydroimidazo[4,5-c]quinolin-2-one (Compound Y) can be prepared according to the following reaction sequence:

Exemplary reaction conditions for each of those steps a-e are given in EXAMPLE 1, as are methods of obtaining the starting compounds. Other suitable reaction conditions will be readily apparent to the skilled person.

Compounds 1 and 2 can then be obtained by suitable methods of separation from Compound Y, exemplary embodiments of which are provided in EXAMPLES 1, 2 and 3.

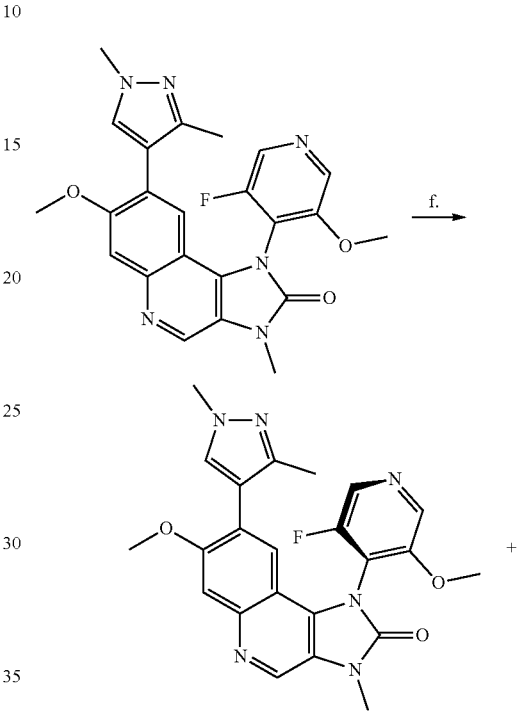

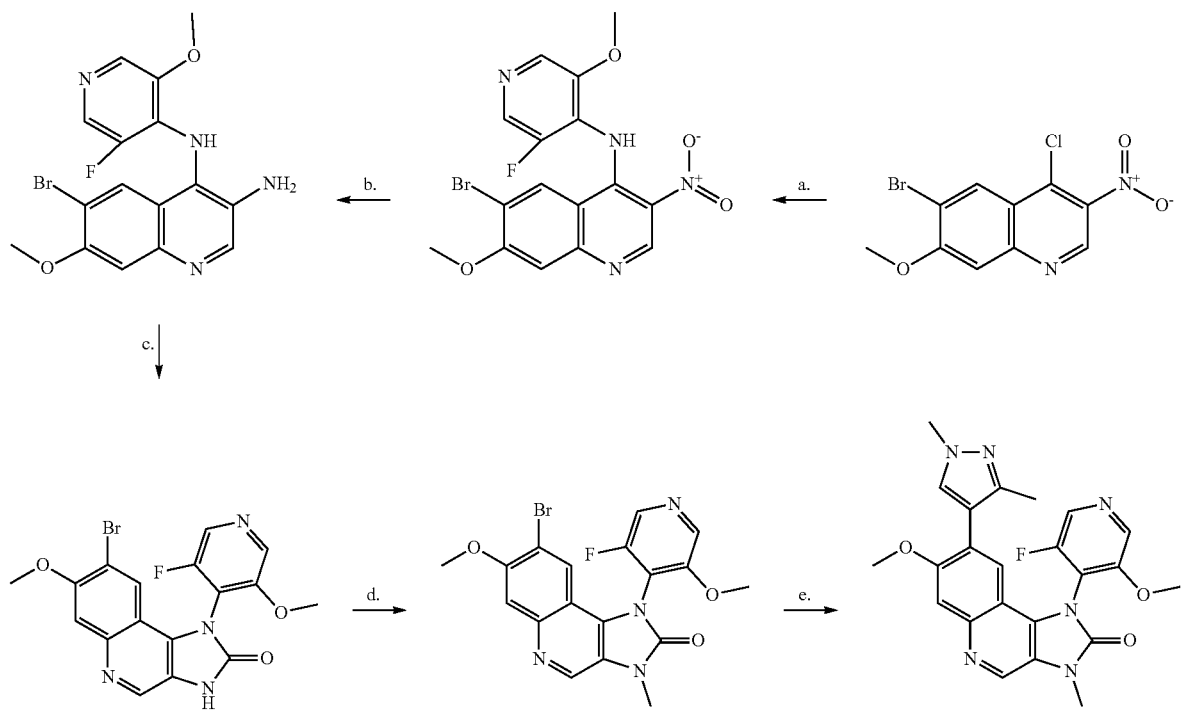

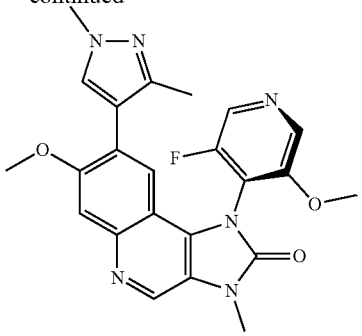

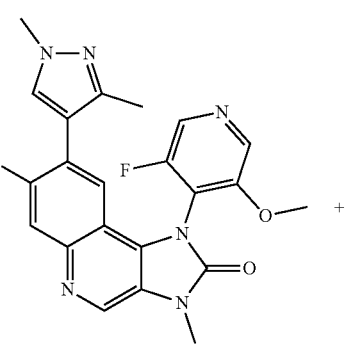

Compound Y

The atropisomers may be separated starting from Compound Y using chiral chromatography, including supercritical fluid chromatography (SFC). Examples of suitable methods are described in detail in EXAMPLES 1 and 3.

The respective undesired atropisomers can be subjected to racemization, e.g. thermal racemization, to yield Compound Y for use as new starting material, as schematically illustrated below by way of one example.

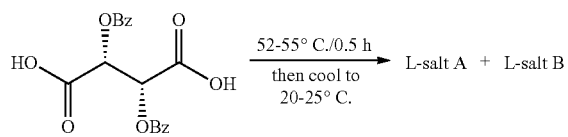

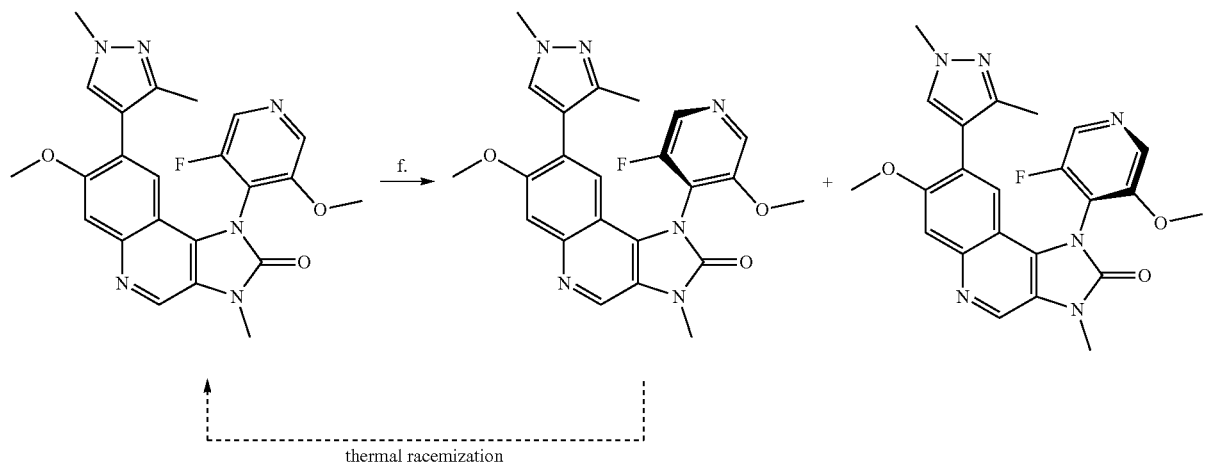

thermal racemization

In an alternative embodiment, Compounds 1 and 2 can be prepared starting from Compound Y by crystallization using an optically active acid, for instance dibenzoyltartaric acid. Reaction of Compound Y with the optically active acid gives a pair of atropisomers salts. These salts of Compounds 1 and 2 exhibit different physicochemical properties (e.g. solubility, phase distribution) and can be separated by taking advantage of these differences.

As illustrated by the scheme below, in one embodiment, Compound Y is reacted with an optically active acid, yielding a mixture of the two salts in the mother solution, with the salt of Compound 2 (L-salt B) precipitating first and being removed by filtration, the corresponding salt of Compound 1 (L-salt A) being collected only after further concentration of the mother solution and precipitation. The salt of Compound 1 is then first converted to its free form and isolated and then reacted with the corresponding other optically active form of the acid to give the corresponding salt of Compound 1, which, in a subsequent step, is converted to the free base with high optical purity. Compound 2 may meanwhile be subjected to racemization to give Compound Y as fresh starting material.

-continued

Solved A (mother liquor) +

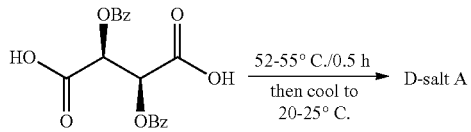

Figure 6:
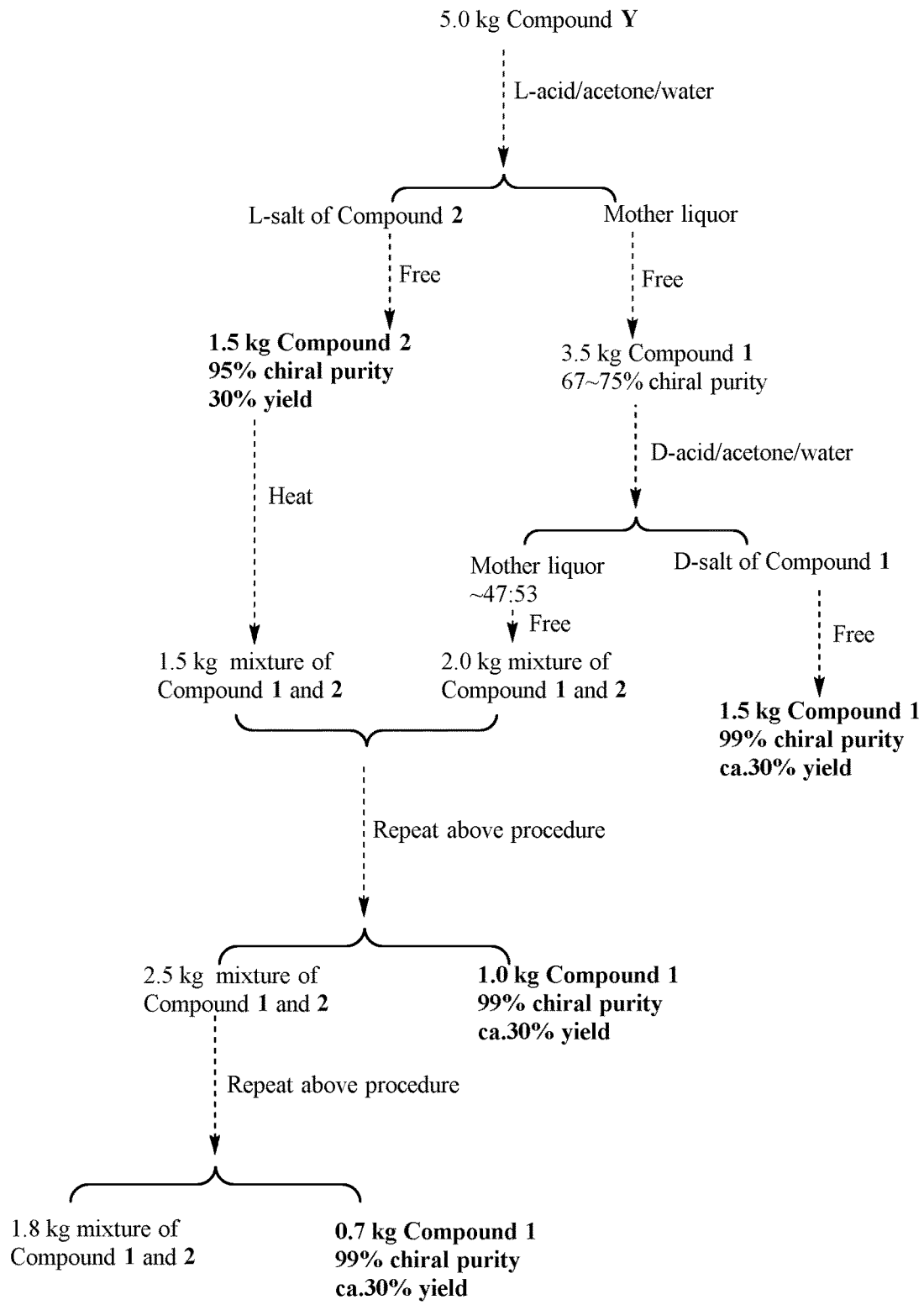
FIG. 6 depicts a flowchart of the preparation of Compound 1.

A detailed example of a suitable preparation scheme is provided in EXAMPLE 2 and FIG. 6.

The deuterated Compounds 3, 4 and 5 according to the present invention can be prepared as described in detail in EXAMPLE 6 and atropisomers, salts, solvates and solid forms prepared substantially as those of Compounds 1 and 2.

Use

In the following, any general reference to the "compounds according to the present invention" shall be meant to apply to all embodiments of the compounds of the present invention, including Compounds 1 or 2, or a pharmaceutically acceptable salt, solvate or solid form thereof, and can be read as "Compound 1 or 2, or pharmaceutically acceptable salt, solvate or solid form thereof". Likewise, any reference to deuterated compounds according to the present invention shall not only include Compounds 3, 4 or 5, but als any atropisomer, salt or solid form of any of the foregoing.

The invention also encompasses the use of the present atropisomers, pharmaceutically acceptable solid forms, solvates and salts thereof as well as deuterated ATM inhibitors, atropisomers and pharmaceutically acceptable salts thereof for the inhibition, regulation and/or modulation of the signalling cascade of ATM kinase, and thus offers novel tools for research and/or diagnostics. The invention therefore furthermore relates to the use of compounds according to the present invention, including deuterated forms thereof for the inhibition of ATM kinase. The term "inhibition" relates to any reduction in the activity which is based on the action of the specific compounds according to the invention in that the latter are capable of interacting with the target molecule in such a way that recognition, binding and blocking is made possible. The compounds are distinguished by high affinity to ATM kinase. The compounds are furthermore highly selective and thus enable substantially exclusive and direct recognition of ATM kinase. For use in research and/or diagnostics, the deuterated compounds, i.e. Compounds 3, 4 or 5, or atropisomers or salt or solid form thereof are considered useful, for instance for use in assays.

The invention generally encompasses the use of the compounds according to the invention, including deuterated compounds, in the treatment of diseases which are caused, mediated and/or propagated by the activity of ATM kinase.

The present invention therefore broadly relates to the compounds according to the invention, including deuterated compounds, for use as a medicament.

The present invention therefore also relates to the compounds according to the invention, including deuterated compounds, for use in the treatment of any disease which is caused, mediated and/or propagated by the activity of ATM kinase. The present invention correspondingly also relates to the use of compounds, including deuterated compounds, according to the invention for the preparation of a medicament for the treatment of any disease which is caused, mediated and/or propagated by the activity of ATM kinase. In other words, the present invention also discloses a compound according to the invention, including a deuterated compound, for use in the treatment of diseases which are influenced by inhibition of ATM kinase.

In addition, the compounds or deuterated compounds according to the invention can also be used as reagents for testing kinase-dependent signalling pathways in animals and/or cell culture models or in the clinical diseases mentioned in this application. As discussed herein, these signalling pathways are relevant for various diseases.

The present invention also relates to the compounds according to the present invention, including pharmaceutically acceptable salts, solvates, solid and deuterated forms thereof, for use in the treatment of cancer and/or tumours; and to the use thereof in the preparation of a medicament for the treatment of cancer and/or tumours.

The invention furthermore teaches a method for the treatment of cancer and/or tumours, in which an effective amount of at least one compound, or pharmaceutically acceptable salt, solvate, deuterated or solid form thereof according to the invention is administered to a subject to be treated. Preferred subjects in the sense of the invention are humans or animals, particularly preferably humans.

The cancer/tumour may be selected, in particular, from the group of cancer/tumour of the squamous epithelium, bladder, stomach, kidneys, head, neck, oesophagus, cervix, thyroid, intestine, liver, brain, prostate, urogenital tract, lymphatic system, larynx, lung, skin, blood and immune system, and/or the cancer may be selected from the group of monocytic leukaemia, lung adenocarcinoma, small-cell lung cancer, non-small-cell lung cancer, pancreatic cancer, colorectal cancer, gastric cancer, breast cancer, ovarian cancer, acute myeloid leukaemia, chronic myeloid leukaemia, acute lymphatic leukaemia, chronic lymphatic leukaemia, Hodgkin's lymphoma and non-Hodgkin's lymphoma. It is to be understood that sensitisation of cancer cells shall encompass cells of the same cancers and tumours mentioned above.

The present invention also relates to a medicament comprising a compound according to the invention and/or pharmaceutically acceptable salt, solvate, deuterated or solid form thereof.

The invention furthermore relates to a pharmaceutical composition comprising a therapeutically effective amount of a compound according to the invention and/or pharmaceutically acceptable salt, solvate, deuterated or solid form thereof, optionally together with at least one pharmaceutically acceptable excipient.

A "medicament" and a "pharmaceutical composition" is to be taken to mean any composition which can be employed in the treatment of patients who, at least temporarily, exhibit a pathogenic modification of the overall condition or the condition of individual parts of the patient organism, preferably as a consequence of cancer and/or tumours.

The delivery of the compounds respectively pharmaceutical composition according to the present invention into a cell or organism can be carried out in accordance with the invention in any manner which enables the ATM kinase to be brought into contact with the compounds present in the pharmaceutical composition, as a consequence of which a response is induced. The pharmaceutical composition of the present invention can be administered orally, transdermally, transmucosally, transurethrally, vaginally, rectally, pulmonarily, enterally and/or parenterally. The type of administration selected depends on the indication, the dose to be administered, individual-specific parameters, etc. In particular, various types of administration may facilitate site-specific therapy, which minimises side effects and reduces the active-compound dose. Injections may be intradermal, subcutaneous, intramuscular or intravenous. The administration can be carried out, for example, with the aid of so-called vaccination guns or by means of syringes. It is also possible to provide the substance as an aerosol, which is inhaled by the organism, preferably a human patient.

In preferred embodiments, the compounds according to the present invention (in any of their forms) are administered orally. Oral administration is favourable in terms of patient compliance. Therefore, pharmaceutical compositions are preferably oral solid pharmaceutical compositions.

It is an advantage of the compounds according to the present invention, in particular Compounds 1 and 2 and solid forms thereof, in particular Compound 1 respectively a solid form thereof, that they readily lend themselves to formulation into an oral solid dosage form, due to good stability and high bioavailability.

Compositions

Compositions respectively pharmaceutical compositions according to the present invention may be prepared using conventional solid or liquid excipients corresponding to the desired type of administration in a suitable dosage and in a manner known per se. Thus, pharmaceutically acceptable excipients known to the person skilled in the art can basically form part of the pharmaceutical composition according to the invention, where the amount of the excipient(s) which is combined with the active compound in order to prepare a single dose varies depending on the dose and the type of administration. Such pharmaceutically acceptable excipients include fillers, stabilisers, complexing agents, antioxidants, solvents, binders, lubricants, salts, buffers, preservatives, adjusters and the like. Examples of excipients of this type are water, vegetable oils, benzyl alcohols, alkylene glycol, polyethylene glycol, Kolliphor, glycerol triacetate, gelatine, carbohydrates, such as, for example, lactose or starch, hydroxypropylmethylcellulose (HPMC), magnesium stearate, talc and Vaseline.

As mentioned above, the present pharmaceutical composition is preferably for oral administration. The pharmaceutical composition can generally be in the form of a tablet, film tablet, dragee, lozenge, capsule, pill, powder, granules, syrup, juice, drops, solution, dispersion, suspension, suppository, emulsion, implant, cream, gel, ointment, paste, lotion, serum, oil, spray, aerosol, adhesive, plaster or bandage. Oral administration forms are preferably tablets, film tablets, dragees, lozenges, capsules, pills, powders, granules, syrups, juices, drops, solutions, dispersions or suspensions.

Furthermore, parenteral pharmaceutical compositions, such as, for example, suppositories, suspensions, emulsions, implants or solutions, may be considered, preferably oily or aqueous solutions. For topical application, the compounds according to the present invention may be formulated in a conventional manner with at least one pharmaceutically acceptable excipient, such as, for example, microcrystalline cellulose, and optionally further assistants, such as, for example, moisturisers, to give compositions which can be applied to the skin, such as, for example, creams, gels, ointments, pastes, powders or emulsions, or to give liquid formulations which can be applied to the skin, such as, for example, solutions, suspensions, lotions, sera, oils, sprays or aerosols.

The pharmaceutical composition could also be in the form of an injection solution. For the preparation of the injection solution, an aqueous medium, such as, for example, distilled water or physiological salt solutions, can be used. The pharmaceutical composition may also be provided in the form of a solid composition, for example in the lyophilised state, and may then be prepared for administration by injection through addition of a dissolving agent, such as, for example, distilled water or a buffer. The person skilled in the art is familiar with the basic principles of the preparation of lyophilisates.

The amount of a compound according to the present invention in the pharmaceutical composition which contains at least one pharmaceutically acceptable excipient can be 0.1 to 100 percent by weight. It is crucial that the pharmaceutical composition comprises an effective amount of the compound, optionally together with one or more pharmaceutically acceptable excipients. A simple pharmaceutical composition may be the compound according to the present invention in a solid form, such as a powder, in a hard gelatine capsule. The terms "effective amount" or "effective dose" are used interchangeably herein and denote an amount of the compound according to the present invention which has a therapeutically relevant effect on a disease or pathological change in cell, tissue, organ or mammal, preferably cancer and/or tumour.

"Therapeutically effective amount" of a compound according to the invention refers to an amount effective, at dosages and for periods of time necessary, that, when administered to a patient with an ATMi modulated or dependent condition, preferably cancer, will have the intended therapeutic effect, e.g., alleviation, amelioration, palliation, or elimination of one or more manifestations of the condition respectively cancer in the patient, or any other clinical result in the course of treating a patient. A therapeutically effective dose does not necessarily occur by administration of one dose and may occur only after administration of a series of doses. Thus, a therapeutically effective amount may be administered in one or more administrations. Such therapeutically effective amount may vary according to factors such as the disease state, age, sex, and weight of the individual, and the ability of the compound according to the invention, alone or in combination, to elicit a desired response in the individual. A therapeutically effective amount is also one in which any toxic or detrimental effects of a compound according to the invention are outweighed by the therapeutically beneficial effects.

In an embodiment of the invention, a compound according to the invention (or salt, solvate, deuterated or solid) is administered at a dose of 5 mg to 1 g per dosage unit, for instance between 10 and 750 mg per dosage unit, such as between 20 and 500 mg per dosage unit, such as 25, 50, 75, 100, 125, 150, 175, 200, 225, 250, 275, 300, 325 or 350 mg per unit. A biologically efficacious dose for Compound 1 has been estimated to be in the range of 25 to 350 mg qd.

Owing to their surprisingly strong and/or selective inhibition of ATM kinase, which regulates cellular processes via repair of double-strand DNA, the compounds of the invention can be administered in an advantageously low dose, while they achieve similar or even superior biological efficacy compared with less-potent or less-selective inhibitors. A reduced dose is typically associated with reduced medical side effects. In addition, highly selective inhibition is generally also reflected by a reduction in undesired side effects.

"Treating" or "treatment of" a condition or patient refers to taking steps to obtain beneficial or desired results, including clinical results. For purposes of this invention, beneficial or desired clinical results include, but are not limited to, alleviation, amelioration of one or more symptoms of the disease to be treated, most preferably cancer; diminishment of extent of disease; delay or slowing of disease progression; amelioration, palliation, or stabilization of the disease state; or other beneficial results. It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms. In certain embodiments, "treating" includes (1) and (2).

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors.

"Administering" or "administration of" a compound to a patient (and grammatical equivalents of this phrase) refers to direct administration, which may be administration to a patient by a medical professional, or may be self-administration, and/or indirect administration, which may be the act of prescribing a drug. E.g., a physician who instructs a patient to self-administer a drug or provides a patient with a prescription for a drug shall be regarded as administering the drug to the patient in the context of the present invention.

All of the above and further excipients or other components of a medicament or pharmaceutical formulation are familiar to the person skilled in the art and may undergo special formulation for the teaching according to the invention in routine experiments.

Combination Therapy

Medicaments and pharmaceutical compositions which comprise a compound according to the invention, and the use of these compounds for the treatment of kinase-mediated disorders are a highly promising approach for the treatment of cancer, in particular. The compounds according to the present invention may be administered as monotherapy, but preferably, as outlined above, in combination with other therapies, such as, for example, chemo- or radiotherapy. As set out above, reference to a compound shall include any salt, solvate, deuterated or solid forms thereof.

The key participation of ATM in DNA repair processes and the evidence that ATM kinase deficiency allows mammal cells to become more radiation sensitive enables therapeutic use of the ATM-specific inhibitors as part of the treatment of cancer, for example, solid tumours, by irradiation therapy and/or chemotherapy, the chemotherapy being preferably aimed at inducing DNA double-strand damage. As explained before, ATM is an attractive intervention to inhibit the repair of therapy-induced DSBs. Hence, the compounds according to the present invention, in any of their forms, are highly advantageous in combination with radiotherapy and/or DNA-damaging chemotherapy.

Accordingly, the present invention concerns a combination of a compound according to the invention and radiotherapy (RT). Accordingly, the present invention relates to a compound of the present invention, or pharmaceutically acceptable salt or solid form thereof, for use in the treatment of cancer and/or tumours in combination with radiotherapy. Expressed differently, the present invention concerns the use of a compound according to the present invention, or pharmaceutically acceptable salt or solid form thereof, for the preparation of a medicament for treating cancer and/or tumours in combination with radiotherapy and thus a method of treating cancer involving administering a compound according to the present invention or pharmaceutically acceptable salt or solid form thereof in combination with radiotherapy. The present invention further relates to a compound according to the present invention or pharmaceutically acceptable salt or solid form thereof for use in sensitizing cancer cells to ionizing radiation respectively radiotherapy (RT).

Figure 20:
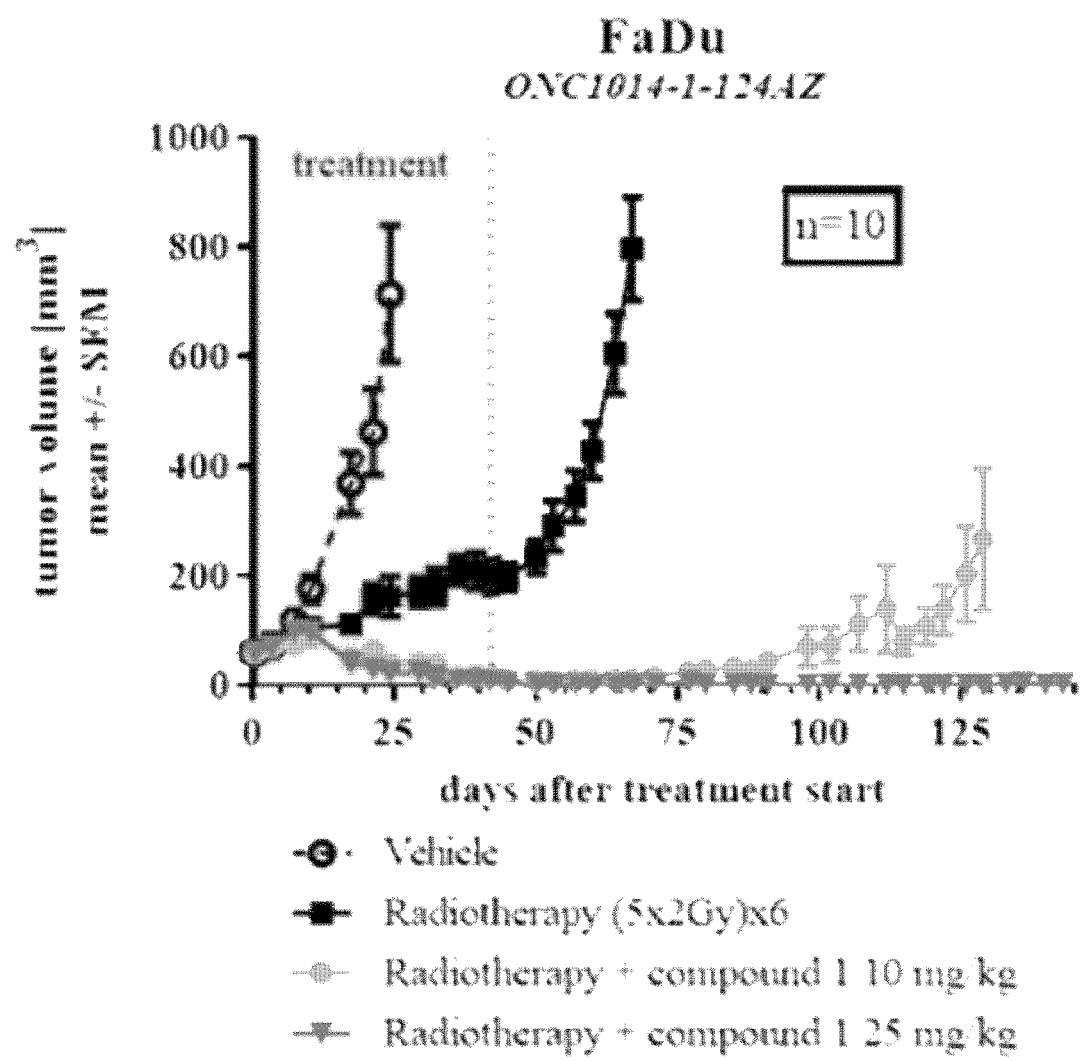
FIG. 20 shows strong tumor growth inhibition induced by irradiation (IR) and concomitant administration of oral Compound 1 (6×5 days, 2 Gy; FaDu SCCHN Tumor Model).

Compound 1 has been shown to lead to significant dose-dependent anti-tumor responses in vivo in combination with clinically relevant radiation schedules (i.e. radiotherapy). EXAMPLE 8 and FIG. 20 provide details of the results achieved.

A suitable administration regime may involve, to name but one example, administration of a RT dose of 15 Gray (Gy) given in 5 fractions (3 Gy given per fraction day) over a weeks (i.e. on 5 consecutive days, followed by 2 days without) and on the same days administration of a compound according to the invention perorally, which may be repeated at least once.

Industrial irradiation methods which are used clinically preferably include photon irradiation (classical, electromagnetic X-ray/gamma radiation), proton irradiation, heavy-ion irradiation (ionised carbon) and neutron irradiation, without being restricted thereto. These radiotherapies and other suitable irradiation therapies in the sense of the invention are known to the person skilled in the art, such as, for example, from Herrmann et al. (2006) Klinische Strahlenbiologie [Clinical Radiation Biology], Elsevier Munich, 4th Edition, 67-68; Bhide & Nutting (2010) BMC Medicine 8: 25; Choi & Hung (2010) Current Urology Reports 11(3): 172, the entirety of which is hereby incorporated herein by reference). As the most frequent application, photon irradiation has been refined technically by the IMRT (intensity-modulated radiotherapy) method and by imaging methods (three-dimensional conformal radiotherapy) in irradiation planning and performance for the most precise focusing possible.

According to a further aspect, the present invention relates to a combination of a compound according to the present invention and a DNA-damaging agent; thus to a compound according to the present invention for use in the treatment of cancer and/or a tumour in combination with a DNA-damaging agent, the use of a compound according to the invention for the preparation of a medicament for treating cancer in combination with a DNA-damaging agent and a method of treating cancer involving administration of a compound according to the present invention and a DNA-damaging agent. As generally explained herein before, compound shall include pharmaceutically acceptable salts, solid forms and solvates, in particular in relation to compositions and treatments.

Administration of the DNA-damaging agent and compound according to the present invention may be simultaneous or sequential.

As used herein, a DNA-damaging agent is an agent that is capable of inducing DNA damage in a cell, particularly preferably cancer cell, with exemplary embodiments mentioned below.

As explained before, ATM kinase is a key regulator of DNA double-strand break (DSB) repair, which is induced by widely used cancer therapeutics, such as ionizing radiation (IR) and DNA-damaging agents. Upon DSB events, ATM signals to a multitude of downstream effectors including p53. Unrepaired DSBs lead to activation of checkpoint responses, cell cycle arrest, and ultimately tumor cell death.

In one embodiment of the invention, the present invention provides a pharmaceutical composition comprising a therapeutically effective compound according to the invention and a DNA damaging agent.

A DNA-damaging agent suitable for use in the combination (therapy), including pharmaceutical composition or kit, is preferably selected from the group comprising:

alkylating agents, such as altretamine, bendamustine, busulfan, carmustine, chloroambucil, chloromethine, cyclophosphamide, dacarbazine, ifosfamide, improsulfan tosylate, lomustine, melphalan, mitobronitol, mitolactol, nimustine, ranimustine, temozolomide, thiotepa, treosulfan, mechloroetamine, carboquone, apaziquone, fotemustine, glufosfamide, palifosfamide, pipobroman, trofosfamide, uramustine:

platinum compounds, such as carboplatin, cisplatin, eptaplatin, miriplatin hydrate, oxaliplatin, lobaplatin, nedaplatin, picoplatin, satraplatin;

topoisomerase inhibitors, for example irinotecan, SN38, topotecan, camptothecin, rubitecan, belotecan, etoposide, daunorubicin, doxorubicin, aclarubicin, epirubicin, idarubicin, amrubicin, pirarubicin, valrubicin, zorubicin, amsacrine;

poly-(ADP-ribose)-polymerase (PARP) inhibitors, for example olaparib, niraparib, veliparib;

ATR (ataxia telangiectasia and Rad3 related) inhibitors, for example M6620 (VX-970: 3-[3-(4-Methylaminomethyl-phenyl)-isoxazol-5-yl]-5-[4-(propane-2-sulfonyl)-phenyl]-pyrazin-2-ylamine), M4344 (VX-803: 2-Amino-6-fluoro-pyrazolo[1,5-a]pyrimidine-3-carboxylic acid [5'-fluoro-4-(4-oxetan-3-yl-piperazine-1-carbonyl)-3,4,5,6-tetrahydro-2H-[1,4'']bipyridinyl-3'-yl]-amide), AZD-6738 (4-[4-[1-[[S(R)]—S-methylsulfonimidoyl]cyclopropyl]-6-[(3R)-3-methyl-4-morpholinyl]-2-pyrimidinyl]-1H-pyrrolo[2,3-b]pyridine) and 2-[(3R)-3-methylmorpholin-4-yl]-4-(1-methyl-1H-pyrazol-5-yl)-8-(1H-pyrazol-5-yl)-1,7-naphtyridine, DNA-modifying agents, such as amrubicin, bisantrene, decitabine, mitoxantrone, procarbazine, trabectedine, clofarabine, amsacrine, brostallicin, pixantrone, laromustine;

anticancer antibiotics, such as bleomycin, dactinomycin, doxorubicin, epirubicin, idarubicin, levamisol, miltefosine, mitomycin C, romidepsin, streptozocin, valrubicin, zinostatin, zorubicin, daunurobicin, plicamycin, aclarubicin, peplomycin, pirarubicin;

alpha emitters, such as alpharadin ($^{223}$Ra dichloride, Xofgio), $^{211}$At; $^{213}$Bi, $^{225}$Ac, $^{227}$Th;

Particular preference is given to etoposide, irinotecan, razoxane, sobuzoxane, topotecan, camptothecin, doxorubicin, amsacrine, PARP inhibitors and ATR inhibitors.

Figure 21:
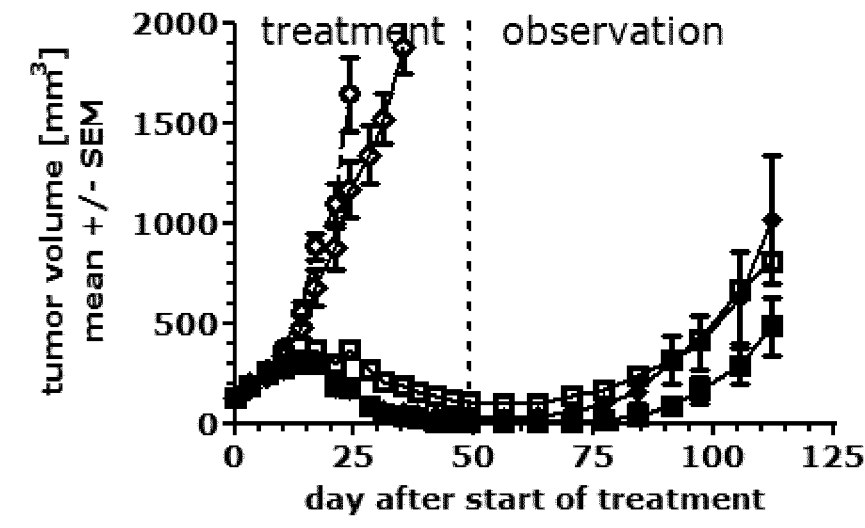
FIG. 21 shows the results of an in vivo evaluation of anti-tumor activity of Compound 1 and a comparative ATM inhibitor in combination with olaparib, in a HBCx-10 patient-derived triple-negative breast cancer xenograft model.
Figure 21:
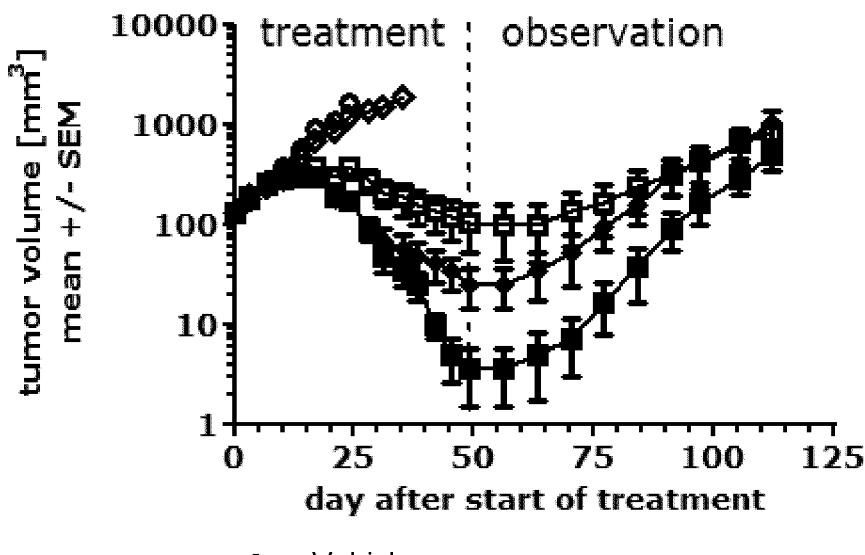

The efficacy of Compound 1 in combination with exemplary PARP inhibitor olaparib was demonstrated in a HBCx-10 patient-derived triple-negative breast cancer xenograft model, developed in immunodeficient female mice, results of which are shown in FIG. 21. More details of this experiment are described in EXAMPLE 9.

The invention can also be practised as a kit, which contains a compound according to the invention. The kit consists of separate packs (a) of an effective amount of a compound according to the invention and/or a physiologically salt, sovate or solid form thereof and (b) of an effective amount of a further active compound. The further active compound is preferably a DNA-damaging agent.

The kit may contain suitable containers, such as, for example, boxes or cartons, individual bottles, bags or ampoules. The kit may contain, for example, separate ampoules or vials, each containing an effective amount of a compound according to the invention and/or pharmaceutically acceptable salt, solvate or solid form thereof, or an effective amount of a further active compound, such as a DNA damaging agent in dissolved or lyophilised form. The kit of the invention may also contain an article which contains written instructions or points the user towards written instructions, which explain the handling of the compounds of the invention.

In summary, it should be noted that the compounds according to the invention can be used individually and/or in combination with other treatment measures, such as, for example, surgical interventions, immunotherapy, radiotherapy and/or chemotherapy. The latter relate to targeted therapy with any desired active compound (chemical or biological, including nMEs: new molecular entities, NCEs: new chemical entities and NBEs: new biological entities) as monotherapy and/or on-target/off-target combination therapy.

All documents cited in the description are hereby intended to be incorporated in their entirety into the disclosure of the present invention by way of reference.

It goes without saying that this invention is not restricted to the specific compounds, pharmaceutical compositions, uses and methods as described herein, since such things can vary. It furthermore goes without saying that the terminology used here serves exclusively the purpose of description of particular embodiments and is not intended to restrict the scope of protection of the invention. As used here in the specification, including the appended claims, word forms in the singular, such as, for example, "a" or "the", include the equivalent in the plural, so long as the context does not specifically indicate otherwise. For example, the reference to "a compound" includes a single compound or a plurality of compounds, which may in turn be identical or different, or the reference to "a method" includes equivalent steps and methods which are known to the person skilled in the art. Referring to subject-matter as "comprising" certain features shall interpreted as meaning that the subject-matter shall include those features, but that it does not exclude the presence of other features, as long as these do not render the subject-matter unworkable.

Experimental

The compounds according to the invention exhibit advantageous properties, as demonstrated by a variety of parameters and experimental results. The experimental methods used for the analysis and characterization of the compounds according to the invention, in all their forms, are provided below.

Assays

Measurement of the kinase activity is a technique which is well known to the person skilled in the art. Generic test systems for the determination of the kinase activity using substrates, for example histone (Alessi et al. (1996) FEBS Lett. 399(3): 333) or the basic myelin protein, are described in the literature (Campos-Gonzalez & Glenney (1992) JBC 267: 14535). Various assay systems are available for the identification of kinase inhibitors. In the scintillation proximity assay (Sorg et al. (2002) J Biomolecular Screening 7: 11) and the flashplate assay, the radioactive phosphorylation of a protein or peptide as substrate are measured using ATP. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are useful as assay methods (Sills et al. (2002) J Biomolecular Screening 191). Other non-radioactive ELISA methods use specific phospho-antibodies (phospho-ABs). The phospho-AB binds only the phosphorylated substrate. This binding can be detected by chemiluminescence using a second peroxidase-conjugated anti-sheep antibody.

For the purposes of the present invention, relevant on-target properties of the compounds were assessed using the following assays:

ATM Kinase Assay—Determination of ATM Inhibition ($IC_{50}$ ATM):

The $IC_{50}$ value was determined with the aid of a biochemical ATM kinase assay. The assay consists of two steps: the enzymatic reaction and the detection step. Firstly, ATM (ataxia telangiectasia mutated) protein and the test substance are incubated at different concentrations with addition of substrate protein p53 and ATP. ATM mediates the phosphorylation of p53 at several positions, including at amino acid S15. The amount of phosphorylated p53 is determined with the aid of specific antibodies and the TR-FRET technique. The enzymatic ATM assay is carried out as TR-FRET (HTRF™, Cisbio Bioassays) based 384-well assay. In the first step, purified human recombinant ATM (human ATM, full length, GenBank ID nM_000051, expressed in a mammal cell line) is incubated in assay buffer for 15 minutes with the ATM inhibitor in various concentrations and without test substance as negative or neutral control. The assay buffer comprises 25 mM HEPES pH 8.0, 10 mM mg ($CH_3COO)_2$, 1 mM $MnCl_2$, 0.1% BSA and 0,01% Brij® 35, 5 mM dithiothreitol (DTT). The test-substance solutions were dispensed into the microtitre plates using an ECHO 555 (Labcyte). In the second step, purified human recombinant c-myc-labelled p53 (human p53, full length, GenBank ID BC003596, expressed in Sf21 insect cells) and ATP are added, and the reaction mixture is incubated at 22° C. for 30-35 minutes. The pharmacologically relevant assay volume is 5 μl. The final concentrations in the assay during incubation of the reaction mixture are 0.3-0.4 nM ATM, 50-75 nM p53 and 10 μM ATP. The enzymatic reaction is stopped by addition of EDTA. The formation of phosphorylated p53 as the result of the ATM-mediated reaction in the presence of ATP is detected via specific antibodies [labelled with the fluorophorene europium (Eu) as donor and d2 as acceptor (Cisbio Bioassays)] which enable FRET. 2 μl of antibody-containing stop solution (12.5 mM HEPES pH 8.0, 125 mM EDTA, 30 mM sodium chloride, 300 mM potassium fluoride, 0.1006% Tween-20, 0.005% Brij® 35, 0.21 nM anti-phospho-p53(ser15)-Eu antibody and 15 nM anti-cmyc-d2 antibody) are added to the reaction mixture. After incubation, usually for 2 hours (between 1.5 and 15 h), for signal development, the plates are analysed in a plate reader (EnVision, PerkinElmer) using TRF mode (and with laser excitation). After excitation of the donor europium at a wavelength of 340 nM, the emitted fluorescence light both of the acceptor d2 at 665 nM and also of the donor Eu at 615 nM is measured. The amount of phosphorylated p53 is directly proportional to the quotient of the amounts of light emitted, i.e. the relative fluorescence units (RFU) at 665 nM and 615 nM. The measurement data were processed by means of Genedata Screener software. $IC_{50}$ determinations are carried out, in particular, by fitting a dose/action curve to the data points by means of nonlinear regression analysis.

$IC_{50}$=half-maximum inhibitory concentration
ATP=adenosine triphosphate
TR-FRET=time-resolved fluorescence resonance energy transfer
HTRF®=homogeneous time resolved fluorescence
HEPES=2-(4-(2-hydroxyethyl)-1-piperazinyl)ethane-sulfonic acid
$Mg(CH_3COO)_2$=magnesium acetate
$MnCl_2$=manganese(II) chloride
BSA=bovine serum albumin
EDTA=ethylenediamine tetraacetate
TRF time resolved fluorescence The abbreviations apply throughout, unless indicated to the contrary.

The assay for determining the IC50 value at an ATP concentration of 1000 μM differs from the above assay only in said ATP concentration.

Cellular pCHK2 Assay:

For the identification of substances which inhibit the phosphorylation of the protein kinase CHK2 (checkpoint kinase 2) at the amino acid threonine 68, an immunofluorescence-based "high content" analysis assay was used in HCT116 cells.

In vitro cell-based immunofluorescence assay for the identification of inhibitors of bleomycin-induced phosphorylation of CHK2 (phospho-Thr68) in the human colon carcinoma cell line HCT116:

HCT116 cells are sown out in a defined cell density in 384-well plates in culture medium (DMEM high glucose, 2 mM GlutaMax, 1 mM Na pyruvate, 10% FCS) and incubated overnight at 37° C. and 10% of $CO_2$. On the following day, the test substances are added in a defined concentration range (1 nM to 30 μM) in combination with 10 μM bleomycin, where the concentration of the solvent DMSO is kept constant at 0.5%. After incubation for four hours at 37° C. and 10% of $CO_2$, the cells are fixed (5 min, 4% formaldehyde in PBS), permeabilised (10 min, 0.2% Triton X-100 in PBS) and, after blocking of nonspecific binding sites (10% goat serum, 1% BSA in PBS), incubated overnight at 4° C. with a specific anti-pCHK2 antibody (cell signalling #2661). pCHK2 (Thr68) is determined using an Alexa488-labelled secondary anti-rabbit IgG antibody. Parallel staining of DNA with propidium iodide enables determination of the cell count. The pCHK2 signal is detected using a high-content imager (Molecular Devices IMX Ultra) and automatic image analysis using the MetaXpress software belonging to the instrument. The number of cell nuclei which have a pCHK2 signal above a defined background is determined.

DMEM: Dulbecco's Modified Eagle Medium; FCS: Fetal calf serum, PBS: phosphate buffered saline (abbreviations apply throughout, unless indicated otherwise)

Furthermore, the effect, in particular inhibition, of other kinases and thus the selectivity of the compounds according to the invention can be determined with the aid of the following assays:

ATR/ATRIP Kinase Assay

The $IC_{50}$ value was determined by an ATR/ATRIP enzymatic assay. The assay comprises two steps: the enzymatic reaction and the detection step. First, a mixture of ATR/ATRIP protein (Ataxia Telangiectasia and Rad3-related protein/ATR interacting protein), the compound in question at different concentrations, p53 as substrate protein and adenosine triphosphate (ATP) are incubated in assay buffer. ATR phosporylates p53 at Ser15 and other residues. The amount of phosphorylated p53 is then detected using specific antibodies and the TR-FRET assay technology.

In detail: The ATR/ATRIP enzymatic assay is performed as a TR-FRET- (HTRF™, Cisbio Bioassays) based 384-well assay. In a first step, purified human recombinant ATR/ATRIP (human ATR, full length, GenBank ID: NM_001184.3, and human ATRIP, full length, GenBank ID AF451323.1, co-expressed in a mammalian cell line) is incubated in assay buffer for 15 minutes at 22° C. with test compound at different concentrations or without test compound (as a negative control). The assay buffer contains 25 mM HEPES pH 8.0, 10 mM $Mg(CH_3COO)_2$, 1 mM $MnCl_2$, 0.1% BSA, 0.01% Brij® 35, and 5 mM dithiothreitol (DTT). An Echo 555 (Labcyte) is used for dispensing of compound solutions. Then, in a second step, purified human recombinant cmyc-tagged p53 (human p53, full length, GenBank ID: B0003596, expressed in Sf21 insect cells) and ATP are added and the reaction mixture is incubated for 25-35 minutes, typically 25 minutes, at 22° C. The pharmacologically relevant assay volume is 5 μl. The final concentrations in the assay during incubation of the reaction mixture are 0.3-0.5 nM, typically 0.3 nM, ATR/ATRIP, 50 nM p53, and 0.5 μM ATP. The enzymatic reaction is stopped by the addition of EDTA. The generation of phosphorylated p53 as a result of the ATR mediated reaction in the presence of ATP is detected by using specific antibodies [labeled with the fluorophores europium (Eu) as donor and d2 as acceptor (Cisbio Bioassays)] enabling FRET. For this purpose, 2 µl of antibody-containing stop solution (12.5 mM HEPES pH 8.0, 125 mM EDTA, 30 mM sodium chloride, 300 mM potassium fluoride, 0.006% Tween-20, 0.005% Brij® 35, 0.21 nM anti-phospho-p53(Ser15)-Eu antibody, 15 nM anti-cmyc-d2 antibody) are added to the reaction mixture. Following signal development for 2 h the plates are analyzed in an EnVision (PerkinElmer) microplate reader using the TRF mode with laser excitation. Upon excitation of the donor europium at 340 nm the emitted fluorescence light of the acceptor d2 at 665 nm as well as from the donor Eu at 615 nm are measured. The amount of phosphorylated p53 is directly proportional to the ratio of the amounts of emitted light i.e. the ratio of the relative fluorescence units (rfu) at 665 nm and 615 nm. Data are processed employing the Genedata Screener software. In particular, $IC_{50}$ values are determined in the usual manner by fitting a dose-response curve to the data points using nonlinear regression analysis.

For abbreviations, see above list.

pCHK1 Cellular Assay

Chk1 kinase acts downstream of ATR and has a key role in DNA damage checkpoint control. Activation of Chk1 involves phosphorylation of Ser317 and Ser345 (regarded as the preferential target for phosphorylation/activation by ATR) and occurs in response to blocked DNA replication and certain forms of genotoxic stress. Phosphorylation at Ser 345 serves to localize Chk1 to the nucleus following checkpoint activation.

This assay measures a decrease in phosphorylation of Chk1 (Ser 345) in HT29 colon adenocarcinoma cells following treatment with compound and hydroxyurea (which promotes fork stalling because of dNTP depletion) and using an immunocytochemical procedure and high content imaging.

For the assay HT29 cells are plated in culture medium (DMEM high Glucose (no phenol red), 2 mM Glutamax, 1 mM Pyruvate, 10% FCS into Greiner 384 well plates, black, µclear #781090 (2500 cells/well/30 µl) and incubated for at least 20 hours at 37° C., 10% CO2 and 90% rH. Diluted test compounds (1 nM-30 µM final) and hydroxyurea (3 mM final) are added simultaneously and cells are incubated for 4 h at 37° C. After fixation/permeabilisation with 100% MeOH (−20° C. cold) and permeabilisation with 0.2% Triton X-100 a complete immunocytochemical procedure is performed using a specific anti-pChk1 antibody (Cell Signaling, #2348BF) and fluorescently labelled secondary antibody (Alexa Fluor® 488 goat anti-rabbit F(ab')2 fragment, Invitrogen A11070) and parallel nuclear staining for cell counting.

The nuclear localised pChk1 signal is detected on an ImageXpress Ultra confocal high content reader and reported as % positive cells (nuclei).

DNA-PK Assay

The kinase assay was performed as HTRF® based 384-well assay. In a first step DNA-PK protein complex was incubated with or without test compound for 15 min at 22° C. After addition of the STK-substrate 1-biotin (Cisbio), Mg-ATP, DNA and staurosporine the reaction mixture was incubated for 60-80 min (depending on activity of DNA-PK protein complex) at 22° C. An Echo 555 (Labcyte) was used for dispensing of compound solutions. The assay buffer consisted of 25 mM HEPES pH 7.4, 11 mM $MgCl_2$, 80 mM KCl, 0.45 mM EDTA, and 0.5 mM EGTA, and contained 1 mM dithiothreitol (DTT), 0.17% BSA, and 0.01% Tween® 20. The pharmacologically relevant volume was 5 µl. The final concentrations in the assay during incubation of the reaction mixture were 50-100 ng/well DNA-PK protein complex (depending on activity of DNA-PK protein complex), 1 µM STK-substrate 1-biotin, 10 µM Mg-ATP, 80 ng/well DNA from calf thymus, and 1 µM staurosporine. The enzymatic reaction was stopped by addition of EDTA. The generation of phosphorylated STK-substrate 1-biotin as result of the DNA-PK mediated reaction was detected via a specific anti-phospho STK-antibody (Cisbio) labeled with Europium (Eu) as donor and streptavidin labeled with XL665 (Cisbio) as acceptor allowing FRET. For this purpose, 4 µl of antibody- and streptavidin-containing stop solution (12.5 mM HEPES pH 8.0, 125 mM EDTA, 30 mM sodium chloride, 300 mM potassium fluoride, 0.006% Tween-20, 0.005% Brij® 35, 0.179 nM anti-phospho-STK antibody, 160 nM Streptavidin-XL665) were added to the reaction mixture. Following signal development for 1 h the plates were analyzed on a Rubystar or Pherastar microplate reader (BMG Labtech). The amount of phosphorylated substrate was directly proportional to the ratio of fluorescence units (excitation wavelength 337 nm) at the emission wavelengths 665 nm (Phosphopeptide-sensitive wavelength/emission of XL665) to the units at 620 nm (reference wavelength Europium). IC50-values were calculated using Genedata Screener® software. (Molecular Cancer Therapeutics 2003, 1257-1264; DNA-dependent protein kinase inhibitors as drug candidates for the treatment of cancer; A. Kashishian, H. Douangpanya, D. Clark, S. T. Schlachter, C. Todd Eary, J. G. Schiro, H. Huang, L. E. Burgess, E. A. Kesicki, and J. Halbrook.)

MgATP=magnesium 5'-O-[hydroxy({[(hydroxyphosphinato)oxy]phosphinato}oxy)phosphoryl]adenosine Tween 20=polysorbate 20

EGTA=ethylene glycol bis(aminoethyl ether) N,N,N',N'-tetraacetic acid

BSA=Bovine Serum Albumin

EDTA Ethylendiamine Tetraacetate pDNA-PK Cellular Assay

HCT116 cells are cultured in MEM alpha medium with 10% fetal calf serum and 2 mM glutamine at 37° C. and 10% CO2. The cells were detached from the bottom of the culture vessels using trypsin/EDTA, centrifuged in centrifuge tubes, taken up in fresh medium and the cell density was determined. 100,000 cells were seeded in 1 ml of culture medium per well of a 24-well cell culture plate and cultured overnight. The next day, 10 µM bleomycin (DNA intercalator and DNA double-strand breaker inducer) and the test substances in fresh culture medium were added to the cells and cultured for a further six hours. Cell lysis was then performed and the cell lysates were spotted on a 96-well ELISA plate (Sigma-Aldrich WH0005591M2: total DNA-PK, Abcam ab18192 or Epitomics EM09912: phospho-serine 2056 DNA-PK), which was blocked and coated with DNA-PK specific antibody, and incubated at 4° C. overnight. Subsequently, the 96-well ELISA plates were treated with a detection antibody (Abcam ab79444: total DNA-PK) and a streptavidin-HRP conjugate. The development of the enzymatic reaction was carried out using a chemiluminescent reagent, the chemiluminescence was measured using the Mithras LB940. The signals with the phospho-DNA-PK specific antibody were normalized to the signal with the antibody against the whole protein DNA-PKc. $IC_{50}$ values or percentages were determined by referencing the signal level of the bleomycin-treated vehicle control group (100% of the control). The DMSO control was used as blank.

MEM: Minimum Essential Medium; DMSO: dimethylsulfoxide

PDE2A1 Assay

A commercially available assay was used (Cerep, catalog ref. 4071, SOP no 1C1054), which is designed to evaluate the effects of compounds on the activity of the human phosphodiesterase-2A1 quantified by measuring the formation of 5'AMP from cAMP using a human recombinant enzyme expressed in Sf9 cells.

The test compound, reference compound or water (control) are added to a buffer containing 40 mM Tris/HCl (pH 7.4), 8 mM $MgCl_2$ and 1.7 mM EGTA/NaOH, 1.8 µM cAMP and 1 µCi [$^3$H]cAMP.

Thereafter, the reaction is initiated by addition of the enzyme (about 2.5 U) and the mixture is incubated for 20 min at 22° C.

For basal control measurements, the enzyme is omitted from the reaction mixture.

Following incubation SPA beads are added.

After 30 min at 22° C. under shaking, the amount of [$^3$H]5'AMP is quantified with a scintillation counter (Topcount, Packard).

The results are expressed as a percent inhibition of the control enzyme activity.

The standard inhibitory reference compound is EHNA (erythro-9-(2-hydroxy-3-nonyl) adenine), which is tested in each experiment at several concentrations to obtain an inhibition curve from which its $IC_{50}$ value is calculated.

Bibliographic reference: Maurice D. H., Ke H., Ahmad F., Wang Y., Chung J. and Manganiello V. C. (2014), Advances in targeting cyclic nucleotide phosphodiesterases, Nat. Rev. Drug Discov., Vol. 13 Issue 4: p. 290.

PDE4D2 Assay

A commercially available assay of Cerep was used (Catalog ref. 4077; SOP no 101045) The assay is designed to evaluate the effects of test compounds on the activity of the human phosphodiesterase-4D2 quantified by measuring the formation of 5'AMP from cAMP using a human recombinant enzyme expressed in Sf9 cells.

The test compound, reference compound or water (control) are added to a buffer containing 40 mM Tris/HCl (pH 7.4) and 8 mM $MgCl_2$, 450 nM cAMP and 0.0125 µCi [$^3$H]cAMP.

Thereafter, the reaction is initiated by addition of the enzyme (about 1.5 U) and the mixture is incubated for 20 min at 22° C.

For basal control measurements, the enzyme is omitted from the reaction mixture.

Following incubation SPA (scintillation proximity assay) beads are added.

After 30 min at 22° C. under shaking, the amount of [$^3$H]5'AMP is quantified with a scintillation counter (Topcount, Packard).

The results are expressed as a percent inhibition of the control enzyme activity.

The standard inhibitory reference compound is Ro 20-1724, which is tested in each experiment at several concentrations to obtain an inhibition curve from which its $IC_{50}$ value is calculated.

Bibliographic reference as above.

PDE42A1 Assay

A commercially available assay of Cerep was used (Catalog ref. 4074; SOP no 1C1056), which is designed to evaluate the effects of compounds on the activity of the human phosphodiesterase-4A1A quantified by measuring the formation of 5'AMP from cAMP using a human recombinant enzyme expressed in Sf9 cells.

The test compound, reference compound or water (control) are added to a buffer containing 40 mM Tris/HCl (pH 7.4) and 8 mM $MgCl_2$, 450 nM cAMP and 0.25 µCi [$^3$H]cAMP.

Thereafter, the reaction is initiated by addition of the enzyme (about 10U) and the mixture is incubated for 20 min at 22° C.

For basal control measurements, the enzyme is omitted from the reaction mixture.

Following incubation SPA beads are added.

After 30 min at 22° C. under shaking, the amount of [$^3$H]5'AMP is quantified with a scintillation counter (Topcount, Packard).

The results are expressed as a percent inhibition of the control enzyme activity.

The standard inhibitory reference compound is Ro 20-1724, which is tested in each experiment at several concentrations to obtain an inhibition curve from which its $IC_{50}$ value is calculated.

Bibliographic reference as above.

Additional parameters considered of importance are determined as follows:

Test Method Microsomal Stability (Intrinsic Clearance)

A microsomal stability assay is used to measure in vitro clearance (Clint). The assay involves measuring the rate of disappearance of a compound due to its intrinsic attitude to be metabolized ("intrinsic" meaning that the disappearance is not affected by other properties like permeability, binding etc. that play a role when quantifying in vivo clearance). The microsomal stability (intrinsic clearance, Clint) and, thus, metabolic stability is generally given as µl/min/mg protein. It can be visualized as the volume of solution that 1 mg of microsomes is able to clear of the compound in one minute.

Instrumentation

A Tecan Genesis workstation (RSP 150/8) was used for to perform the microsomal incubations. Analysis was carried out using a Waters ACQUITY UPLC system coupled to an ABSciex AP13000 mass spectrometer. Data analysis was performed using Assay Explorer (Symyx).

UPLC Conditions

Column: Acquity UPLC BEH C18, 2.1×50 mm, 1.7 µm (Waters)

Mobile phases: A=0.1% formic acid in water; B=acetonitrile

| Gradient Time | % A | % B |
|---|---|---|
| initial | 90 | 10 |
| 0.47 | 5 | 95 |
| 0.65 | 5 | 95 |
| 0.66 | 90 | 10 |

Flow rate: 0.750 mL/min; Detection: ESI, MRM; Injection: 10 µL; Column temperature: 50° C.

Chemicals

Potassium phosphate buffer: 0.05 M potassium phosphate buffer pH 7.4 containing 1 mM $MgCl_2$ NADPH (nicotinamide adenine dinucleotide phosphate): 22.5 mg NADPH-$Na_4$ in 1.8 ml potassium phosphate buffer Acetonitrile: 50 Vol % acetonitrile (1 volume acetonitrile, 1 volume water)

DMSO: 20 Vol % DMSO in water

Stock solution of 20 mg/ml human or mouse liver microsomes (protein)/ml in phosphate buffer Stock solution of 10 mM compound in 100% DMSO Microsomal Incubation Dilution of test compounds was done in 2 steps starting from a 10 mM stock solution of the respective compound in 100% DMSO. First 4 μl stock solution was added to 196 μl of 20 Vol % DMSO. In a second step, 10 μl of the first dilution were added to 1590 μl potassium phosphate buffer to achieve a final concentration of 1.25 μM in the final compound dilution. Thus, the amount of organic solvent in the assay was kept to a minimum (<1%).

The human or mouse liver microsome (protein) solution to be used in the assay was prepared by mixing 750 μl stock solution (20 mg/ml) and 2250 μl potassium phosphate buffer to a final concentration of 5 mg/ml.

Incubation was carried out on a 96 deep well incubation plate. 160 μl per well of the final compound dilution were transferred onto the incubation plate. Four samples of each compound dilution were assayed. 20 μl/well liver microsome solution was added to each well and the samples were then preincubated for 5 min at 37° C. and 800 rpm agitation. Two reference compounds (verapamil and dextromethorphan) were used in parallel in every experiment and for each species (human or mouse microsomes) to ensure system performance and for comparison.

On a separate stop plate, 160 μl acetonitrile were added per well.

After preincubation, i.e. at time $t_1$=0 minutes, 18 μl samples of incubated compound solution and were transferred and added per well (containing acetonitrile) on the stop plate to prevent a reaction (0 minutes control samples, 4 samples per compound). Equally, 18 μl samples of incubated reference compound solution were transferred and added per well (containing acetonitrile) on the stop plate at time $t_1$=0 minutes and again after 30 minutes ($t_4$), solubility and chemical stability of the compound were checked.

To start the reaction, 26 μl NADPH solution (cofactor) was added to all wells comprising preincubated compound dilution or reference solution with the exception of those wells comprising preincubated compound dilution that were to be used as the 30 minutes control samples, where 26 μl phosphate buffer were added instead. Incubation was then continued at 37° C. and 800 rpm agitation.

In the final assay solutions (i.e. in each well comprising solution of compound, microsomes (protein) and NADPH respectively phosphate buffer), the final protein concentration was 0.5 mg/ml and the compound concentration 1 mg/ml.

After $t_2$=5 minutes, $t_3$=10 minutes and $t_4$=20 minutes of incubation time (i.e. after start of the reaction), 20 μl samples of incubated compound solution (4 samples per compound) and reference compound solution were transferred and added per well of acetonitrile on the stop plate.

After $t_4$=30 minutes of incubation time, 20 μl samples of incubated compound solution (4 samples per compound) and 20 μl samples of the 30 minutes control samples (containing buffer instead of NADPH) as well as 20 μl samples of incubated reference compound solution were transferred and added per well of acetonitrile on the stop plate.

The quenched samples were centrifuged at 4000 g for 1 h at 4° C. 80 μl of the supernatant were transferred into 96 well plates for analysis by LC-MS/MS.

Data Analysis

The microsomal/metabolic stability of each compound was determined by measurement of the change in LC-MS/MS peak area over time. Data are fitted according to a log linear model in line with Michaelis/Menten. The Clint value is calculated from the slope (k) of the linear log transformed concentration per time plot divided by the amount of microsomes (0.5 mg/ml): Clint (μl/min/mg protein)= k*1000/protein concentration. Assay Explorer software was used to automatically calculate the slope k of the decline.

Kv11.1 (hERG) Ion Channel Activity (Patch Clamp Assay)

Method for the detection and characterisation of test substances which interfere with the Kv11.1 (hERG) channel: Kv11.1 (hERG, human ether a-go-go related gene) is a potassium channel which plays a central role for repolarisation of the cells in the ventricular cardiomyocytes.

The patch-clamp measurement was carried out at room temperature in whole-cell configuration on human embryonic kidney cells (HEK293) which have been transfected in a stable manner with the hERG gene.

The whole-cell configurations were carried out using an automated patch clamp device (Patchliner™, Nanion Technologies, Munich). This is a glass chip-based system with which automated whole-cell measurements on up to 8 cells simultaneously are possible. The glass chip has a hole of defined size to which the cell is transferred into the Gigaseal by application of a reduced pressure and brought into the whole-cell configuration. Buffer, cell suspension and test substances were added to microchannels of the chip using a Teflon-coated pipette.

The cells were clamped to a holding potential of −80 mV. For measurement of substance-promoted inhibition of the Kv11.1 channel, the following voltage protocol was applied at 10-second intervals: 51 ms/−80 mV, 500 ms/+40 mV, 500 ms/−40 mV, 200 ms/−80 mV. The leakage current is subtracted by means of the P4 method. The cells were resuspended in extracellular buffer (EC) and applied to the chip. After the cell had been collected, the seal was improved by addition of a seal enhancer buffer. As soon as the whole-cell configuration had been reached, the seal enhancer buffer was washed out and replaced by extracellular buffer. The measurement started in EC for 1.5 min. DMSO (vehicle control, 0.1% of DMSO) was then applied, and the control current was recorded for 3 min. The test substance was subsequently added twice in the same concentration, and the potassium current was measured for 3.5 min in each case.

If the measurement result of a test substance at an initial concentration of 10 μM was smaller than (−)50% effect (threshold value) (for example (−)60% effect), the test substance was, in order to determine a dose/action relationship, added cumulatively in increasing concentration, where each concentration was measured for 5 min.

The reference substance used was the Kv11.1 (hERG) ion channel blocker quinidine. The effects of test substances and quinidine were standardised to the associated vehicle control. The effect on the Kv11.1 (hERG) channel activity was assessed from the potassium current at −40 mV. For the calculation, the current was evaluated for the respective final trace. A test-substance-induced inhibition of the Kv11.1 (hERG) channel was standardised to the vehicle control (0.1% of DMSO).

During the measurement, an aliquot of the test substance was taken for concentration determination. The sample was measured immediately by HPLC, and the final concentration was determined from a calibration curve.

If the measurement result of a test substance at an initial concentration of 10 μM is greater than or equal to (−)50% effect (threshold value) (for example (−)30% effect, i.e. 30% inhibition at 10 µM), the $K_i$ is calculated in accordance with the following formula: $K_i=1.0E-5\times(100+\% \text{ effect})/(-\% \text{ effect})$, [M].

The measurement result of (−)30% effect at a test substance concentration of 10 µM gives a $K_i$ of 23 µM.

Cytochrome P-450 Enzymes (CYP)

In the human organism, drug substances are converted to water-soluble compounds by enzyme systems to facilitate their excretion. These enzyme systems include microsomal cytochrome P-450 enzymes, CYPs for short. The assay is designed to identify whether a compound may be a strong inhibitor for defined CYP isoforms. This involves the use of recombinant CYP isoforms and their reductase obtained by overexpression in insect cells infected with baculovirus. The CYP reaction is performed through inhibition of the CYP isoform being tested along with a luminometric CYP substrate under NADPH-regenerating conditions. The luminometric P450-Glo™ substrates are derivatives of beetle luciferin ((4S)-4,5-dihydro-2-(6-hydroxybenzothiazolyl)-4-thiazolecarboxylic acid or D-luciferin), a substrate of firefly luciferase from beetles. The luminometric P450-Glo™ substrates do not react directly with luciferase, but are converted by the respective CYP isoform to a luciferin product which is luminescent upon reaction with luciferin detection reagent (LDR). This allows enzyme activity to be quantified rapidly through the luminosity. The extent of inhibition is measured by determining the IC50 value (Crespi et al., Methods Enzymol. 357:276-284, 2002). The following commercially available screening systems/assays are used: P450-Glo™ CYP1A2 Screening System (Promega Corporation; V9770); P450-Glo™ CYP2C8 Assay (Promega Corporation; V8782); P450-Glo™ CYP2C9 Screening System (Promega Corporation; V9790); P450-Glo™ CYP2C19 Screening System (Promega Corporation; V9880); P450-Glo™ CYP2D6 Screening System (Promega Corporation; V9880); P450-Glo™ CYP3A4 Screening System (Luciferin-PPXE) (Promega Corporation; V9910).

Bioavailability

The predicted bioavailability in humans is derived from the measured bioavailabilities in the preclinical species: Mouse, rat and dogs (Beagle) and is calculated for the predicted pharmacologically effective dose in humans (in silico GastroPlus simulation).

Powder X-Ray Diffraction (PXRD) Method:

The X-ray powder diffractograms (XRPD), such as those depicted in FIGS. 7B and 10 to 19 (and others), were obtained using the following methodology: Samples were prepared in a combinatorial 96-well-plate (comprising an X-ray amorphous foil as bottom), or between X-ray amorphous films. Measurements have been performed in transmission geometry with Cu-$K_{\alpha 1}$ radiation on a Stoe StadiP 611 diffractometer. Scans were from 0-36° 2θ simultaneously (step width of 0.03° 2θ, 30 seconds per step), or covering 1-65° 2θ (step width of 0.015° 2θ, 15 seconds per step), respectively.

Single-Crystal X-Ray Diffraction:

Single crystal X-Ray Structure data were obtained using a SuperNova diffractometer from Agilent, equipped with CCD Detector using Cu Kα radiation. Measurements were performed at 200 K (Form H2) or at 298 K (Forms A1, A2, A3, H1), respectively. Single crystal data were used for the determination of crystal system and unit cell parameters.

Differential Scanning calorimetry (DSC):

DSC scans were acquired on a Mettler-Toledo heat-flux Differential Scanning calorimeter with autosampler, using a nitrogen inert gas atmosphere (50 mL/min). Overview scans were carried out in Al 40 µL pans with open lids from 25-300° C. at 5° C./min.

Thermogravimetric Analysis (TGA):

TGA scans were acquired on a Mettler-Toledo Thermogravimetric Analyser with autosampler, using a nitrogen inert gas atmosphere (50 mL/min). Overview scans were carried out in Al 100 µL pans without lids from 25-300° C. at 5° C./min. Experiments were baseline-corrected with a blank run from an empty Al 100 µL pan without lid, using the same temperature profile.

Dynamic Vapor Sorption (DVS):

DCS water vapour sorption isotherms were acquired on DVS instrument with microbalance and incubator (DVS-Intrinsic, Surface Measurement Systems, SMS). Powder samples were accurately weighed into disposable Al pans and placed on the sample position of the DVS instrument. A nitrogen overall follow rate of 200 mL/min (combined dry and humid stream) was used for humidification. Water vapour sorption isotherms were acquired at 25° C., using an initial desorption segment 1 from 40% RH (relative humidity) to 0% RH (with 10% RH steps), an adsorption segment from 0% RH to 98% RH (with 10% RH steps and a final 8% RH step, respectively), and a final desorption segment 2 from 98% RH to 0% RH (with an initial 8% RH step and 10% RH steps, respectively). For all RH steps, an equilibrium condition of dm/dt≤0.0005 wt %/min was used, with a minimum RH step time of 10 minutes and a maximum RH step time (timeout) of 360 minutes.

Non-Sink Dissolution Profiles of Solid-State Forms:

Non-sink dissolution profiles for solid-state forms were acquired using shaked-flask method with excess solid material in FaSSIF medium (pH 6.5) with time-resolved sampling for determination of dissolved quantities of API.

Approx. 10-20 mg of solid sample were weighed into glass vials. 7 ml of respective medium (prewarmed to 37° C.) were added and the suspension was shaken at 450 rpm at 37° C. After 5 min, 10 min, 15 min, 30 min, 60 min, 120 min, 24 h and 48 h, 1 ml suspension was withdrawn and filtered through a 0.2 µm syringe filter. Clear filtrate was analysed by HPLC after suitable dilution to measure the amount of compound/form (may also be referred to as API) dissolved.

FaSSIF: 3 mM sodium taurocholate; 0.75 mM lecithin; 105.9 mM sodium chloride; 28.4 mM monobasic sodium phosphate and 8.7 mM sodium hydroxide, pH 6.5

HPLC Method for pH-Dependent Solubility & Miniaturised Non-Sink Dissolution:

Levels of dissolved compound/form were analysed by HPLC, with the following conditions:

Column: Chromolith RP-18e 100-3 mm
Solvent A: water/formic acid (999:1; v/v)
Solvent B: acetonitrile/formic acid (999:1; v/v)
Injection volume: 5 µL
Column temperature: 37° C.
HPLC-Gradient:

| Time (minutes) | Eluent A (%) | Eluent B (%) | Flow (mL/min) |
|---|---|---|---|
| 0.0 | 90 | 10 | 1.7 |
| 0.3 | 90 | 10 | 1.7 |
| 2.0 | 10 | 90 | 1.7 |
| 2.75 | 10 | 90 | 1.7 |

EXAMPLES

The following Examples illustrate the invention described above; they are not, however, intended to limit the scope of the invention in any way. The Examples should, in particular, be interpreted in such a way that they are not restricted to the features or feature combinations specifically illustrated, but instead the illustrative features can be freely amended or combined so long as the object of the invention is achieved. The beneficial effects of the compounds, combinations, and compositions of the present invention can also be determined by other analytical method and experimental set-ups known as such to the person skilled in the pertinent art. Likewise, modifications to the methods of preparation, in particular reaction conditions, will be readily apparent to the skilled person.

Example 1: Preparation of Compounds 1 and 2

Compound Y is prepared accordance with the procedure disclosed in WO 2016/155884, followed by separation of Compounds 1 and 2 from Compound Y:

a. Synthesis of 6-bromo-N-(3-fluoro-5-methoxy-4-pyridyl)-7-methoxy-3-nitro-quinolin-4-amine Under a dry nitrogen atmosphere, a solution of 3-fluoro-5-methoxypyridin-4-amine (447 mg, 3.02 mmol) dissolved in N,N-dimethylformamide (5 mL) was provided. Then, sodium hydride (504 mg, 12.6 mmol, 60%) was added to the solution and stirring continued for 5 minutes at room temperature. 6-Bromo-4-chloro-7-methoxy-3-nitro-quinoline (800 mg, 2.52 mmol) was then added to the reaction mixture, followed by 15 minutes of stirring at room temperature, then by quenching of the reaction through addition of ice water (100 mL). The precipitate was filtered off, washed with ice water and dried to give 1.00 g (94%) 6-bromo-N-(3-fluoro-5-methoxy-4-pyridyl)-7-methoxy-3-nitro-quinolin-4-amine as a yellow solid.

b. Synthesis of 6-bromo-$N^4$-(3-fluoro-5-methoxy-4-pyridyl)-7-methoxy-quinoline-3,4-diamine 6-Bromo-N-(3-fluoro-5-methoxy-4-pyridyl)-7-methoxy-3-nitro-quinolin-4-amine (990 mg, 2.20 mmol) dissolved in

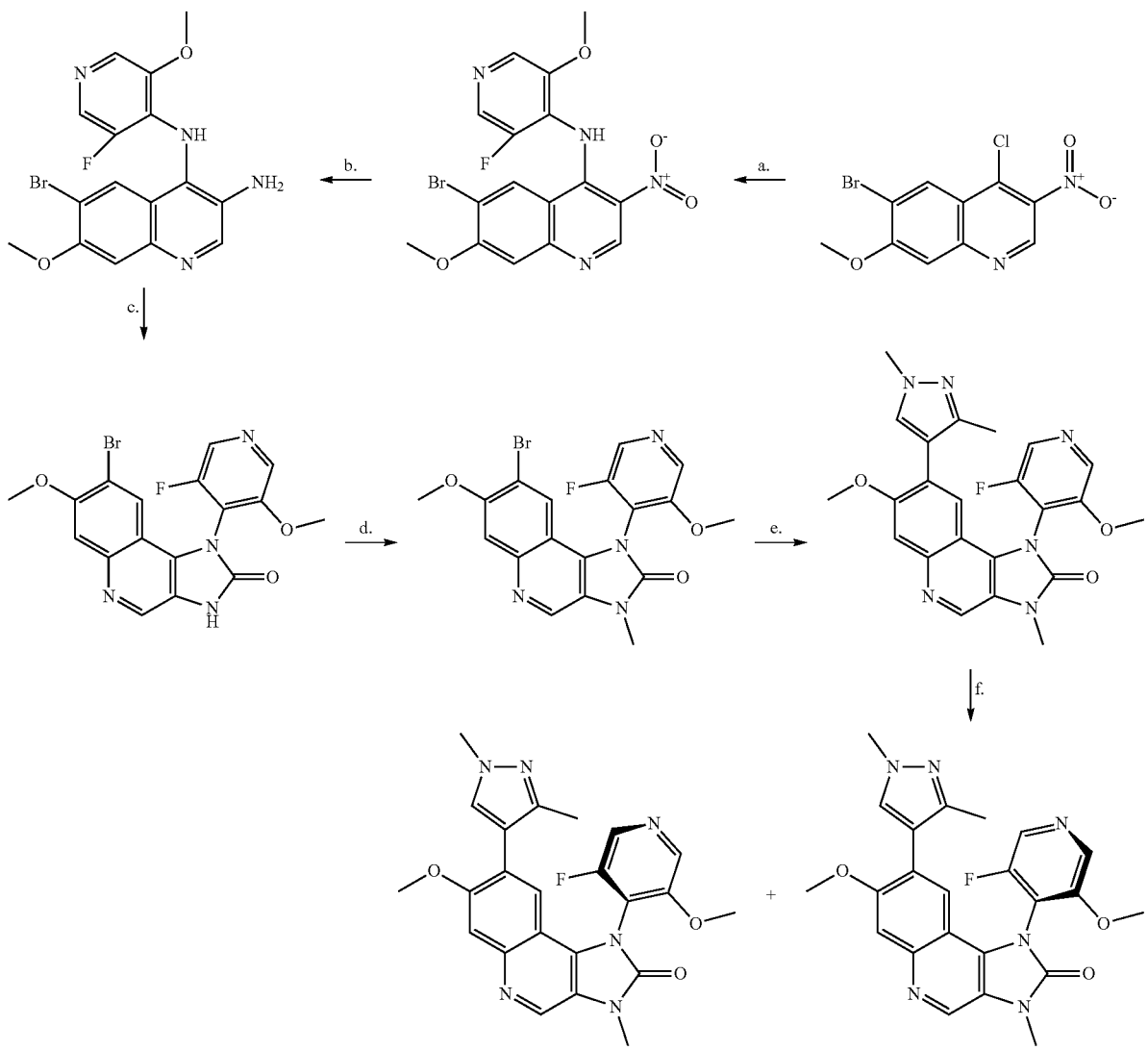

methanol (100 mL) was provided under a protective nitrogen atmosphere. Then, Raney-Ni (100 mg, 1.17 mmol) was added to the solution, and the reaction mixture was stirred for 30 minutes under a hydrogen atmosphere at normal pressure. After introducing nitrogen, the suspension was filtered and the filtrate dried under vacuum. The filtrate was evaporated to dryness under vacuum. The residue was crystallized from a mixture of ethyl acetate/petroleum ether, yielding 0.86 g (99%) 6-bromo-$N^4$-(3-fluoro-5-methoxy-4-pyridyl)-7-methoxy-quinoline-3,4-diamine as a yellow solid.

c. Synthesis of 8-bromo-1-(3-fluoro-5-methoxy-4-pyridyl)-7-methoxy-3H-imidazo[4,5-c]quinolin-2-one A solution of 6-bromo-$N^4$-(3-fluoro-5-methoxy-4-pyridyl)-7-methoxy-quinoline-3,4-diamine (0.85 g, 2.20 mmol) dissolved in tetrahydrofuran (20 mL) was provided. Then, 1,1'-carbonyldiimidazole (1.84 g, 11.3 mmol) and Hünig's-base (1.46 g, 11.3 mmol) were added. The reaction mixture was heated to 40° C. and stirred for 16 hours. The reaction was then quenched by the addition of ice water (200 mL). The precipitate was filtered off, washed with ice water and dried to give 0.87 g (94%) 8-bromo-1-(3-fluoro-5-methoxy-4-pyridyl)-7-methoxy-3H-imidazo[4,5-c]quinolin-2-one as a light yellow solid.

d. Synthesis of 8-bromo-1-(3-fluoro-5-methoxy-4-pyridyl)-7-methoxy-3-methyl-imidazo[4,5-c]quinolin-2-one In a dry protective nitrogen gas atmosphere, 8-bromo-1-(3-fluoro-5-methoxy-4-pyridyl)-7-methoxy-3H-imidazo[4,5-c]quinolin-2-one (0.86 g, 1.94 mmol) dissolved in N,N-dimethylformamide (5 mL) was provided. Then, sodium hydride (388 mg, 9.71 mmol, 60%) and methyl iodide (2.76 g, 19.4 mmol) were added. The reaction mixture was stirred for 10 minutes at room temperature. Then the reaction was quenched by the addition of ice water (100 mL). The resulting precipitate was filtrated and dried under vacuum to give 0.70 g (80%) 8-bromo-1-(3-fluoro-5-methoxy-4-pyridyl)-7-methoxy-3-methyl-imidazo[4,5-c]quinolin-2-one as a light yellow solid.

e. Synthesis of 1-(3-fluoro-5-methoxy-4-pyridyl)-7-methoxy-3-methyl-8-(1,3-dimethylpyrazol-4-yl)imidazo[4,5-c]quinolin-2-one Under an argon inert gas atmosphere in closed equipment 8-bromo-1-(3-fluoro-5-methoxy-4-pyridyl)-7-methoxy-3-methyl-imidazo[4,5-c]quinolin-2-one (150 mg, 0.33 mmol), 1-3-dimethyl-4-(tetramethyl-1,3,2-dioxaborolan-2-yl)-1H-pyrazole (88.4 mg, 0.40 mmol), Pd(PPh$_3$)$_4$ (76.6 mg, 0.07 mmol) and potassium carbonate (91.6 mg, 0.66 mmol) in 1,4-dioxane (15 mL) and water (5 mL) were provided. The reaction mixture was heated to 80° C. with stirring for 2 hours. This was followed by cooling to room temperature and reducing the reaction mixture to dryness under vacuum. The residue was chromatographically purified using silica (ethyl acetate/methanol=97:3, parts by volume). The eluate was reduced to dryness and the resulting raw product purified by means or preparative RP-HPLC (water/acetonitrile). After reducing the product fractions, 1-(3-fluoro-5-methoxy-4-pyridyl)-7-methoxy-3-methyl-8-(1,3-dimethylpyrazol-4-yl)imidazo[4,5-c]quinolin-2-one (70 mg, 47%) was obtained as a colourless solid.

f. Separation of 8-(1,3-dimethyl-1H-pyrazol-4-yl)-1-(Ra)-(3-fluoro-5-methoxy-pyridin-4-yl)-7-methoxy-3-methyl-1,3-dihydro-imidazo[4,5-c]quinolin-2-one and 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one 1-(3-fluoro-5-methoxy-4-pyridyl)-7-methoxy-3-methyl-8-(1,3-methylpyrazol-4-yl)imidazo[4,5-c]quinolin-2-one (50.0 mg, 0.11 mmol) as obtained above was separated via chiral HPLC using SFC to give Compounds 1 and 2. The substance was applied to chiral column Lux Cellulose-2 and separated at a flow of 5 mL/min with CO$_2$/2-propanol+0.5% diethylamine (75:25) as the solvent and using detection at a wavelength of 240 nm. Reducing the product fractions at reduced pressure yielded 8-(1,3-Dimethyl-1H-pyrazol-4-yl)-1-(Ra)-(3-fluoro-5-methoxy-pyridin-4-yl)-7-methoxy-3-methyl-1,3-dihydro-imidazo[4,5-c]quinolin-2-one (25.0 mg, 50%) and 8-(1,3-Dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one) (22.1 mg, 44%), both as colourless solids.

The starting compounds are readily obtainable, for instance as shown below:

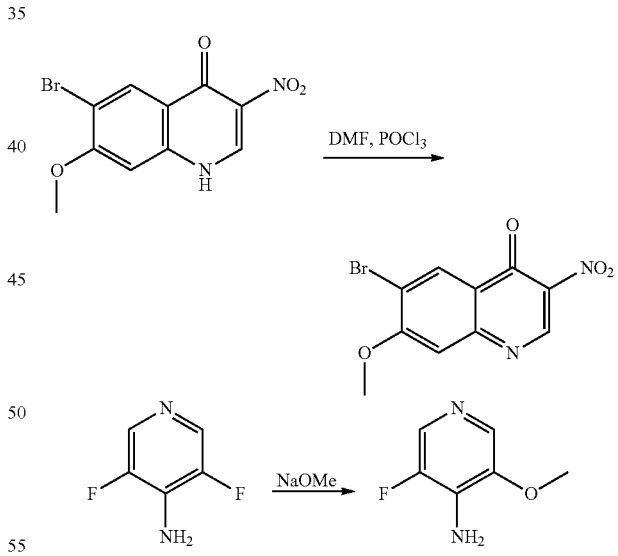

Example 2: Isolation of the Atropisomers and Purification of Compound 1

Compounds 1 and 2 can be isolated from Compound Y as shown in Scheme 1 and in FIG. 6 and as discussed in detail below. One of ordinary skill in the art will appreciate that the process described below is equally applicable for compounds 3-a and 3-b from 3, 4-a and 4-b from 4, as well as 5-a and 5-b from 5.

Scheme 1: Preparation of the Chiral Salts

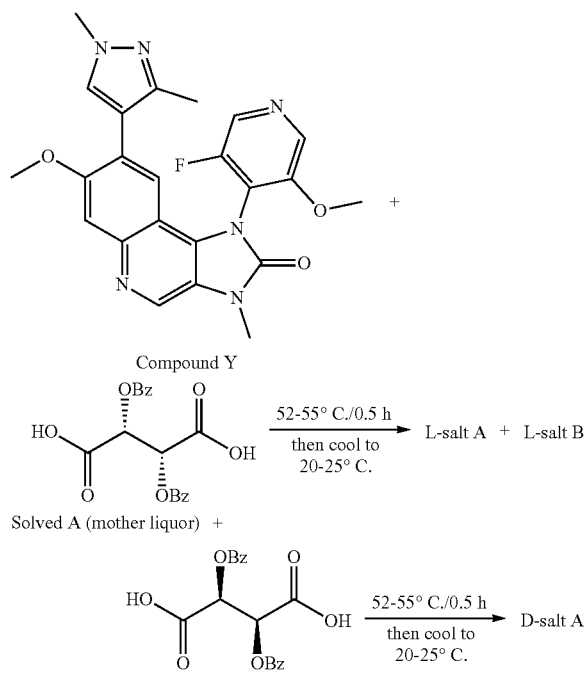

Step 1:
1. Into a 200 L reactor, acetone (108 L, 20 vol.), purified water (8.13 L, 1.5 vol.) and Compound Y (5.42 Kg, 1.0 eq.) were added at 20-25° C.
2. Charged with dibenzoyl-L-tartaric acid (4.33 Kg, 1.0 eq.).
3. Heated to 52-55° C. to give a clear solution, stirred for 0.5 h at 52-55° C.
4. Cooled to 20~25° C.
5. Filtered and washed filter cake with acetone (5.4 L, 1 vol.) once.
6. Collected the cake and dried to give the L-salt B (L-salt of Compound 2) (light yellow solid with 95.9% of chiral purity).
7. Concentrated the mother solution and obtained the L-salt A (L-salt of Compound 1).
8. Into a 100 L reactor was added L-salt A and DCM (38 L, 7 vol.), pH adjusted to 8-9 with saturated NaHCO$_3$ solution.
9. Collected the dichloromethane (DCM) layer, extracted the saturate NaHCO$_3$ with DCM (16.3 L, 3 vol.), combined the DCM layers, washed the DCM layer with H$_2$O (10.8 L, 2 vol).
10. Concentrated the DCM layer. Then, acetone (5.4 L, 1 vol.) was added at 20~25° C.
11. Stirred at 20-25° C. for 1 h.
12. Filtered, collected the cake and dried to give the Compound 1 (3.50 Kg, white solid with 73.2% of chiral purity, Y:64.6%).

Step 2:
1. Into a 50 L flask was added L-salt B and DCM (16.2 L, 3 vol.), pH adjusted to 8-9 with saturated NaHCO$_3$ solution.
2. Collected the DCM layer, extracted the aqueous layer with DCM (5.4 L, 1 vol.), combined the DCM layers, washed the DCM layer with H$_2$O (5.4 L, 1 vol.).
3. Exchanged the DCM with 2-ethoxyethanol (1.8 L, 0.3 vol.) twice under vacuum at 40~50° C.
4. Adjusted the volume with 2-ethoxyethanol to 5.4 L (1 vol.).
5. Heated to 128-130° C. to give a slurry, stirred for 44 h at 128-130° C.
6. IPC (Ratio 49.5:50.5).
7. Cooled to 15-20° C.
8. Filtered and washed the cake with methyl-tert.-butyl-ether (2.7 L, 0.5 vol).
9. Collected the cake and dried to give the Compound Y (1.60 kg, off-white solid, overall yield: 29.5%).

Step 3:
1. Into a 100 L reactor was added acetone (70 L, 20 vol.) at 20~25° C., stirred and added Compound 1 (3.5 Kg, 1.0 eq.), charged water (5.3 L, 1.5 vol.).
2. Charged with Dibenzoyl-D-tartaric acid (2.8 Kg, 1.0 eq.) at 35~40° C., heated to 52~55° C. to give a clear solution, stirred for 0.5 h at 52~55° C.
3. Cooled to 20-25° C. with oil bath and stirred for 17 h at 20~25° C.
4. Filtered and washed the cake with acetone (3.5 L, 1 vol.).
5. Collected the cake to give the D-salt A (D-salt of Compound 1) (light yellow solid with 98.7% chiral purity).
6. Concentrated the mother solution, then saturated NaHO$_3$ solution (15.5 L, 3.5 vol.) and H$_2$O (15.5 L, 3.5 vol.) was added.
7. Stirred for 0.5 h at 20~25° C.
8. Filtered and washed the cake with H$_2$O (3.5 L, 1 vol.).
9. Collected the filter cake and dried to give the Compound Y (1.53 Kg, white solid with a ratio of 50.3:49.7, Y:43.7%).

Step 4:
1. Into a 50 L reactor was added D-salt A (D-salt of Compound 1) and acetone (17.5 L, 5 vol.), warmed to 52~55° C. to give a slurry solution, stirred for 0.5 h at 52~55° C.
2. Cooled to 20-25° C. and stirred for 17 h at 20~25° C.
3. Filtered and washed the cake with acetone (3.5 L, 1 vol).
4. Collected the filter cake and dried to give the D-salt A (3.23 Kg, light yellow solid with 99.2% of chiral purity).
5. Into a 50 L reactor was added D-salt A, then saturated NaHCO$_3$ solution (16 L, 5 vol.) and H$_2$O (16 L, 5 vol.) was added.
6. Stirred for 0.5 h at 20-25° C.
7. Filtered and washed the cake with H$_2$O (16 L, 5 vol.).
8. Collected the cake and dried to give the Compound 1 (1638 g, white solid with 99.1% chiral purity and 99.9% of HPLC, overall yield: 30.2%).

Example 3: Chromatographic Separation, Purification and Analysis 3.1 Compounds 1 and 2 can be isolated from Compound Y using chromatography on a chiral stationary phase (see, e.g., Chiral Liquid Chromatography; W. J. Lough, Ed. Chapman and Hall, New York, (1989); Okamoto, "Optical resolution of dihydropyridine enantiomers by high-performance liquid chromatography using phenylcarbamates of polysaccharides as a chiral stationary phase", J. of Chromatogr. 513:375-378, (1990)). Compounds 1 and 2 can be isolated by chromatography on chiral stationary phase, for example, a Chiralpak IC column (5 mm, 150×4.6 mm I.D.) e.g., using isocratic elution with a mobile phase containing: H$_2$O/ACN 50/50 v/v (ACN: acetonitrile; v: volume). One of ordinary skill in the art will appreciate that the same procedure can be applied for compounds 3-a and 3-b, 4-a and 4-b as well as 5-a and 5-b.

Figure 5:
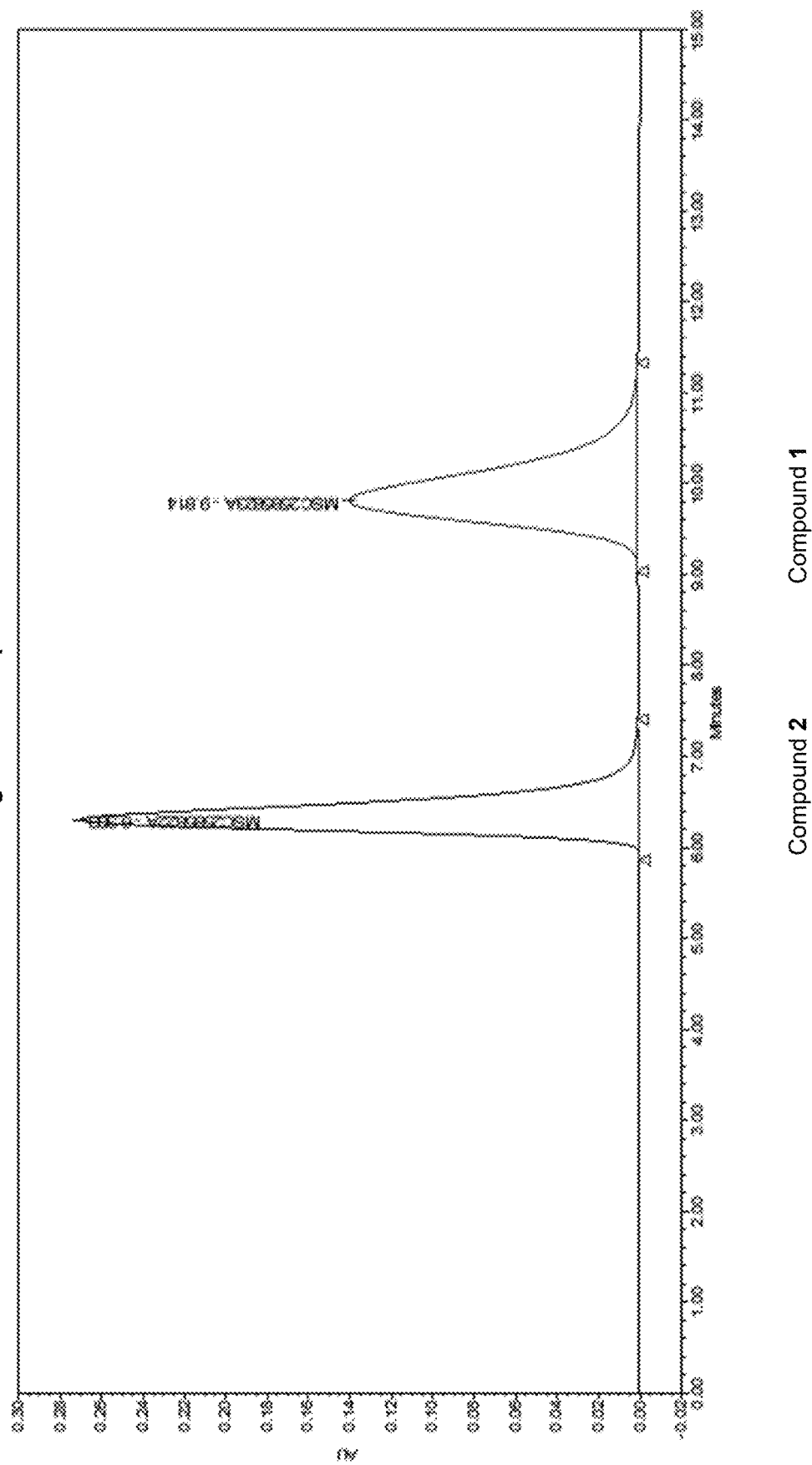
FIG. 5 depicts an HPLC chromatogram of Compounds 1 and 2.

A thus obtained chromatogram is illustrated in FIG. 5 (Column and elution as mentioned above, flow 1.00 ml/min, UV @ 260 nm; $T_c$ and $T_s$: 25±5° C., $S_{conc}$ 0.20 mg/ml, injected volume 10 ml)

3.2 As an alternative to the SFC conditions mentioned above, preparative supercritical fluid chromatography may be used, involving for instance: Chiralpak AS-H (20 mm×250 mm, 5 μm) column; isocratic elution (20:80 ethanol:$CO_2$ with 0.1% v/v $NH_3$), BPR (back-pressure reg.): about 100 bar above atmospheric pressure; a column temperature of 40° C., a flow rate of 50 ml/min, an injection volume of 2500 μl (125 mg) and a detector wavelength of 265 nm. 3.3 For the analysis of the purity of the respective atropisomers, again, SFC may be applied, for instance using the following set-up: Chiralpak AS-H (4.6 mm×250 mm, 5 μm) column; isocratic elution (20:80 ethanol:$CO_2$ with 0.1% v/v $NH_3$), BPR (back-pressure reg.): about 125 bar above atmospheric pressure; a column temperature of 40° C., a flow rate of 4 ml/min, an injection volume of 1 μl and a detector wavelength of 260 nm.

Example 4: Stability of Compounds 1 and 2

Quantum Mechanics Calculations of Rotational Barriers

LaPlante et al. (ChemMedChem, 2011, 6(3), 505-513) describe a quantum-mechanical workflow to estimate energy barriers to axial rotation of drug-like molecules. A similar approach was applied: 3D structures of all input molecules have been generated using CORINA (Corina version 3.6, Molecular Networks, Germany) and subsequently been minimized with Macromodel (version 11.1, Schrödinger, LLC, New York, NY). Based on these input structures rotational energy barriers were calculated from relaxed dihedral angle scans using the program Jaguar (version 9.1 release 14, Schrödinger, LLC, New York, NY) employing the B3LYP/6-31G** method with a torsion angle increment of 15°. The structures were optimized prior to the torsion scan using the same level of theory. Default parameters have been used except that the maximum number of minimization steps was set to 500 and the stop_rxn flag has been introduced to avoid artificial bond breaks. For all calculations, representative molecular fragments have been used. The dihedral obtained from the molecular mechanics minimized structure has been used to define the starting value for the dihedral scan, e.g. for Compound 1 of this invention or for "LaPlante reference Compound 1" values have been set to 47.32° and 35.8° respectively. For each torsion about the axial bond QM energy values have been calculated in 24 steps. The torsion profile has been obtained by plotting the torsion angle values to the calculated energies. The lowest energy barrier for each compound has been determined that allows for interconversion between both isomers. For reference compounds 1-6 experimentally determined interconversion rates and deduced energy barriers are known. The computationally energy barriers for reference compounds 1-6 are between 9.865 and 31.316 kcal/mol. These values have been fitted to experimental determined interconversion rates.

Calculations for Compound 1 of this invention and of Compound 2 of this invention revealed a high predicted rotational barrier of 29.205 kcal/mol that translates into a highly stable atropisomer with a predicted rotational half-life in the range of years (>10 years). The required temperature for onset of racemization of either enantiomeric atropisomer is >100° C.

One of ordinary skill in the art will appreciate that these values are also exemplary for compounds 3-a and 3-b, 4-a and 4-b as well as 5-a and 5-b.

Example 5: Pharmaceutically Acceptable Salts of Compound 1

Salts of Compound 1 (Compounds 1-a), which are pharmaceutically acceptable, were prepared as shown and discussed in detail below.

Preparation of Fumarate-Salt (Form NF6):

Approx. 20 mg of 8-(1,3-Dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one were dissolved in 1 mL THF at 50° C. (p.a. grade) in a 4 mL glass vial with closed cap, equipped with a magnetic stirring bar, and by using a magnetic stirrer. At 50° C., approx. 5.7 mg fumaric Acid (~1.1 eq.) were added into the hot solution, and cooled down to 5° C. at a cooling rate of 0.1 K/min. The mixture was repeatedly heated to 50° C. (within approx. 30 min) and cooled down to 5° C. (at 0.1 K/min) under stirring, prior to a final equilibration step at 5° C. for several hours. To increase yield of salt formation in the cooled solution, the mixture was further exposed to n-pentane slow anti-solvent vapor diffusion in a closed vial configuration. Finally obtained solid material was separated by centrifugation and gently dried under a nitrogen purge.

Preparation of Napsylate-Salt (Form NF7)—Alternative 1:

Approx. 10 mg of 8-(1,3-Dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one were dissolved in ~250 μL Acetone at 50° C. (p.a. grade) in a 4 mL glass vial with closed cap, equipped with a magnetic stirring bar, and by using a magnetic stirrer. At 50° C., approx. 5.6 mg napthalene-2-sulfonic Acid (~1.2 eq.) were added into the hot solution, and cooled down to 5° C. at a cooling rate of 0.1 K/min. The mixture was repeatedly heated to 50° C. (within approx. 30 min) and cooled down to 5° C. (at 0.1 K/min) under stirring, prior to a final equilibration step at 5° C. for several hours. Finally obtained solid material was separated by centrifugation and gently dried under a nitrogen purge.

Preparation of Napsylate-Salt (Form NF7)—Alternative 2:

Approx. 11.5 mg of 8-(1,3-Dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one were dissolved in ~250 μL THF (tetrahydrofuran) at 50° C. (p.a. grade) in a 4 mL glass vial with closed cap, equipped with a magnetic stirring bar, and by using a magnetic stirrer. At 50° C., approx. 6.6 mg napthalene-2-sulfonic Acid (~1.2 eq.) were added into the hot solution, and cooled down to 5° C. at a cooling rate of 0.1 K/min. The mixture was repeatedly heated to 50° C. (within approx. 30 min) and cooled down to 5° C. (at 0.1 K/min) under stirring, prior to a final equilibration step at 5° C. for several hours. Finally obtained solid material was separated by centrifugation and gently dried under a nitrogen purge.

Preparation of Edisylate-Salt (Form NF8):

Approx. 12.6 mg of 8-(1,3-Dimethyl-1H-pyrazol-4-yl)-1-(Sa)-(3-fluoro-5-methoxy-pyridin-4-yl)-7-methoxy-3- methyl-1,3-dihydro-imidazo[4,5-c]quinolin-2-one were dissolved in ~250 μL Acetone at 50° C. (p.a. grade) in a 4 mL glass vial with closed cap, equipped with a magnetic stirring bar, and by using a magnetic stirrer. At 50° C., approx. 6.1 mg Ethanedisulfonic Acid (~1.2 eq.) were added into the hot solution, and cooled down to 5° C. at a cooling rate of 0.1 K/min. The mixture was repeatedly heated to 50° C. (within approx. 30 min) and cooled down to 5° C. (at 0.1 K/min) under stirring, prior to a final equilibration step at 5° C. for several hours. Finally obtained solid material was separated by centrifugation and gently dried under a nitrogen purge.

| Parameter | Fumarate | Napsylate | | Edisylate |
|---|---|---|---|---|
| | | Salt stoichiometry | | |
| | API: Fumarate 1.0:0.9 | API: Napsylate 1:1 | API: Napsylate 1:1 | API: Edisylate 1:1 |
| Melting point | >180° C. | ~209° C. | n.d. | ~223° C. |

Example 6: Preparation of Compounds 3, 4 and 5

Synthesis of 8-(1,3-dimethylpyrazol-4-yl)-1-[3-fluoro-5-(trideuteriomethoxy)-4-pyridyl]-7-methoxy-3-methyl-imidazo[4,5-c]quinolin-2-one

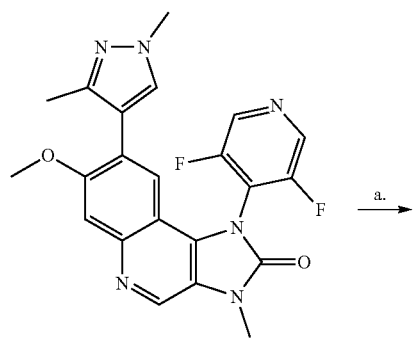

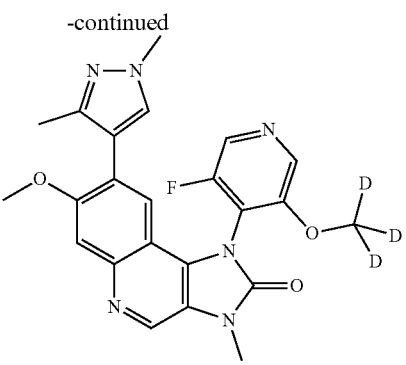

Step a:

Into a sealed tube was placed: 1-(3,5-difluoropyridin-4-yl)-8-(1,3-dimethyl-1H-pyrazol-4-yl)-7-methoxy-3-methyl-1H,2H,3H-imidazo[4,5-c]quinolin-2-one (90.0 mg, 0.20 mmol, 95%), potassium carbonate (85.3 mg, 0.62 mmol), CD₃OD (0.30 mL, 6.74 mmol), N,N-dimethylformamide (3 mL). The mixture was stirred for 1 h at 100° C. 10 mL of water was added and the resulting solution was extracted three times with ethyl acetate (10 mL) and the combined organic layers were dried over anhydrous sodium sulfate, filtered and the filtrate was concentrated to dryness under vacuum. The crude residue was purified by preparative HPLC (SHIMADZU(HPLC-10): Column: Atlantis Prep T3 OBD Column, 19*250 mm, 10 μm; mobile phase: water (10 mmol/L NH₄HCO₃) and acetonitrile (hold 34% acetonitrile for 10 min); Detector: UV 254 nm) to yield 35 mg (38%) of 8-(1,3-dimethyl pyrazol-4-yl)-1-[3-fluoro-5-(trideuteriomethoxy)-4-pyridyl]-7-methoxy-3-methyl-imidazo[4,5-c]quinolin-2-one as a white solid. Meting point 260-262° C. HPLC/MS (purity) 97%. Rt 1.98 min (method A). [M+H]+ 452. 1H NMR (400 MHz, DMSO-d6) ppm=8.92 (s, 1H), 8.70 (d, J=9.5 Hz, 2H), 7.83 (s, 1H), 7.54 (s, 1H), 7.00 (s, 1H), 3.94 (s, 3H), 3.78 (s, 3H), 3.60 (s, 3H), 1.75 (s, 3H).

Synthesis of 8-(1,3-dimethylpyrazol-4-yl)-1-[3-fluoro-5-(trideuteriomethoxy)-4-pyridyl]-7-methoxy-3-(trideuteriomethyl)imidazo[4,5-c]quinolin-2-one

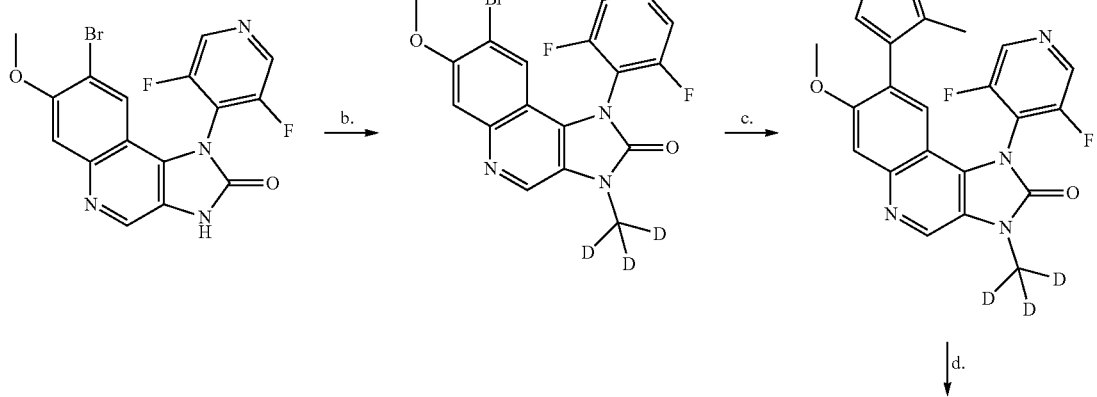

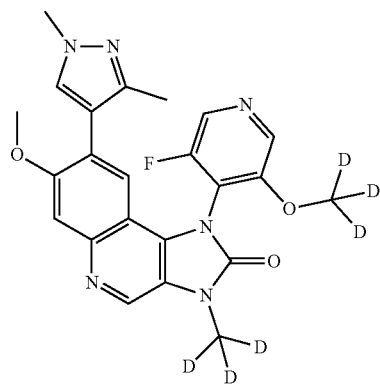

Step b:

Into a round-bottom flask was placed 8-bromo-1-(3,5-difluoropyridin-4-yl)-7-methoxy-1H,2H,3H-imidazo[4,5-c]quinolin-2-one (3.00 g, 6.96 mmol, 94%) in N,N-dimethylformamide (50 mL). Sodium hydride (1.39 g, 34.8 mmol, 60%) was added at 0° C. within 5 min, followed by the addition of $CD_3I$ (3.18 g, 20.9 mmol, 95%). The resulting solution was stirred for 15 min at room temperature. To the mixture, 500 mL of ice water was added and the solids were collected by filtration. This resulted in 2.95 g (99%) of 8-bromo-1-(3,5-difluoro-4-pyridyl)-7-methoxy-3-trideuteriomethyl)imidazo[4,5-c]quinolin-2-one as a yellow solid. HPLC/MS (purity) 99%. Rt 0.93 min (method B). [M+H]+ 424, 426.

Step c:

Into a sealed tube purged and maintained with an inert atmosphere of argon was placed 8-bromo-1-(3,5-difluoro-4-pyridyl)-7-methoxy-3-trideuteriomethyl)imidazo-[4,5-c]quinolin-2-one (1.80 g, 4.20 mmol, 99%), 1,3-dimethyl-4-(tetramethyl-1,3,2-dioxaborolan-2-yl)-1H-pyrazole (1.97 g, 8.43 mmol, 95%), Pd(PPh$_3$)$_4$ (540 mg, 0.42 mmol, 90%), potassium carbonate (1.22 g, 8.39 mmol, 95%), dioxane (50 mL) and water (10 mL). The mixture was stirred for 2 h at 80° C. and concentrated under vacuum to dryness. The residue was purified by column chromatography (methanol/ethyl acetate, 13:87) resulting in 1.35 g (71%) of 1-(3,5-difluoro-4-pyridyl)-8-(1,3-dimethylpyrazol-4-yl)-7-methoxy-3-(trideuteriomethyl)imidazo[4,5-c]quinolin-2-one as a yellow solid. HPLC/MS (purity) 97%. Rt 0.91 min (method C). [M+H]+ 440.

Step d:

Into a sealed tube purged and maintained with an inert atmosphere of argon was placed 1-(3,5-difluoro-4-pyridyl)-8-(1,3-dimethylpyrazol-4-yl)-7-methoxy-3-(trideuteriomethyl)imidazo[4,5-c]quinolin-2-one (1.35 g, 2.96 mmol), N,N-dimethylformamide (30 mL), potassium carbonate (818 mg, 5.92 mmol) and CD$_3$OD (2.76 mL, 2.24 g, 62.2 mmol). The mixture was stirred for 2 h at 100° C. 100 mL of water was added and the resulting mixture was extracted with three times with 200 mL of ethyl acetate. The combined organic layers were washed with twice with 100 mL of brine. The organic layer was dried over anhydrous sodium sulfate, concentrated to dryness and the crude product was crystallized from methanol/acetonitrile (1:25) to yield in 1.50 g (66%) of 8-(1,3-dimethylpyrazol-4-yl)-1-[3-fluoro-5-(trideuteriomethoxy)-4-pyridyl]-7-methoxy-3-(trideuteriomethyl)imidazo[4,5-c]quinolin-2-one as an off-white solid. Melting point 266-271° C. HPLC/MS (purity) 97%. Rt 2.00 min (method C). [M+H]+ 455. 1H NMR (300 MHz, DMSO-d6) ppm=8.87 (s, 1H), 8.65 (d, J=7.5 Hz, 2H), 7.78 (s, 1H), 7.49 (s, 1H), 6.95 (s, 1H), 3.89 (s, 3H), 3.28 (s, 3H), 1.71 (s, 3H).

Synthesis of 1-[3-fluoro-5-(trideuteriomethoxy)-4-pyridyl]-7-methoxy-3-methyl-8-[3-methyl-1-(trideuteriomethyl)pyrazol-4-yl]imidazo[4,5-c]quinolin-2-one

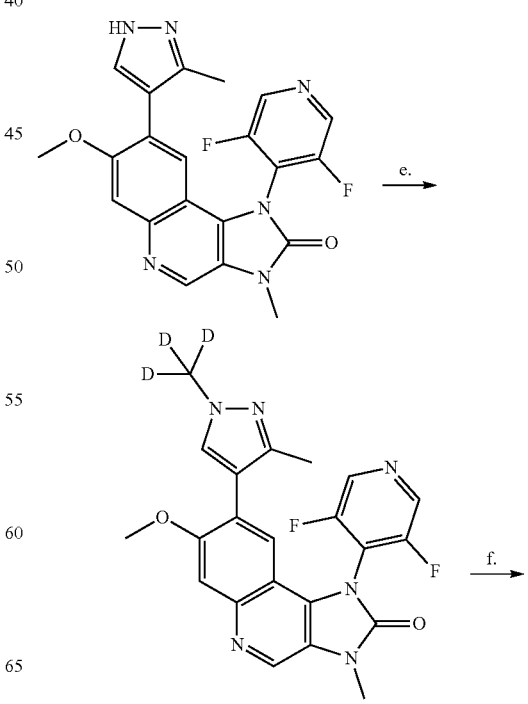

-continued

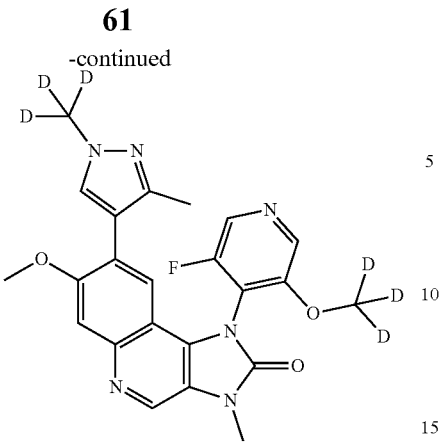

Step e:
Into a round-bottom flask, was placed 1-(3,5-difluoropyridin-4-yl)-7-methoxy-3-methyl-8-(3-methyl-1H-pyrazol-4-yl)-1H,2H,3H-imidazo[4,5-c]quinolin-2-one (890 mg, 1.89 mmol, 90%) in N,N-dimethylformamide (30 mL). Sodium hydride (377 mg, 9.43 mmol, 60%) was added at 0° C. in 5, followed by CD$_3$I (1.44 g, 9.44 mmol, 95%). The resulting mixture was stirred for 8 h at room temperature. 200 mL of ice water was added and solution was extracted with four times with 200 mL of ethyl acetate. The combined organic layers were washed twice with 100 mL of brine. The organic phase was dried over anhydrous sodium sulfate, concentrated to dryness and purified by column chromatography with dichloromethane/methanol (19:1) to yield 400 mg (47%) of 1-(3,5-difluoro-4-pyridyl)-7-methoxy-3-methyl-8-[3-methyl-1-(trideuteriomethyl)pyrazol-4-yl]imidazo[4,5-c]quinolin-2-one as a yellow solid. HPLC/MS (purity) 98%. Rt 0.68 min (method D). [M+H]+ 440.

Step f:
Into a sealed tube purged and maintained with an inert atmosphere of argon was placed 1-(3,5-difluoro-4-pyridyl)-7-methoxy-3-methyl-8-[3-methyl-1-(trideuteriomethyl)pyrazol-4-yl]imidazo[4,5-c]quinolin-2-one (380 mg, 0.84 mmol, 98%), N-methyl-2-pyrrolidone (20 mL), potassium carbonate (368 mg, 2.53 mmol, 95%) and CD$_3$OD (2.45 mL, 53.9 mmol, 98%). The mixture was stirred for 4 h at 100° C. 100 mL of water was added and the resulting solution was extracted 5 times with 100 mL of ethyl acetate. The combined organic layers were washed twice with 100 mL of brine, dried over anhydrous sodium sulfate, concentrated to dryness and purified by column chromatography with dichloromethane/methanol (10:1) to yield in 300 mg (74%) of 1-[3-fluoro-5-(trideuteriomethoxy)-4-pyridyl]-7-methoxy-3-methyl-8-[3-methyl-1-(trideuteriomethyl)pyrazol-4-yl]imidazo[4,5-c]quinolin-2-one as an orange solid. HPLC/MS (purity) 95%. Rt 0.65 min (method D). [M+H]+ 455. 1H NMR (300 MHz, DMSO-d6) ppm=8.87 (s, 1H), 8.65 (d, J=7.5 Hz, 2H), 7.78 (s, 1H), 7.49 (s, 1H), 6.95 (s, 1H), 3.89 (s, 3H), 3.55 (s, 3H) 1.71 (s, 3H).

HPLC Method A:
Column: Shim-pack XR-ODS, 3.0*50 mm, 2.2 µm; mobile phase A: water/0.05% TFA, mobile phase B: acetonitrile/0.05% TFA; flow rate: 1.0 mL/min; gradient: 5% B to 100% B in 2.2 min, hold 1.0 min; 254 nm.

HPLC Method B:
Column: Shim-pack XR-ODS, 3.0*50 mm, 2.2 µm; mobile phase A: water/0.05% TFA, mobile phase B: acetonitrile/0.05% TFA; flow rate: 1.2 mL/min; gradient: 5% B to 100% B in 2.0 min, hold 0.7 min; 254 nm.

HPLC Method C:
Column: Poroshell HPH-C18, 3.0*50 mm, 2.7 µm; mobile phase A: water/5 mM NH$_4$HCO$_3$, mobile phase B: acetonitrile; flow rate: 1.3 mL/min; gradient: 10% B to 95% B in 2.1 min, hold 0.6 min; 254 nm.

HPLC Method D:
Column: Ascentis Express C18, 3.0*50 mm, 2.7 µm; mobile phase A: water/0.05% TFA, mobile phase B: acetonitrile/0.05% TFA; flow rate: 1.5 mL/min; gradient: 5% B to 100% B in 1.2 min, hold 0.5 min; 254 nm.

Example 7: Solid Forms and Solvates of Compound 1

A. Solid Form A2 Preparation
Solid Form A2 of Compound 1 was prepared by different cooling crystallization processes from alcohols:

7.1 Compound 1 was dissolved in 1-propanol at a concentration of approx. 50 mg/mL at 50° C. under stirring. The resulting clear solution was cooled to −20° C. at a cooling rate of 0.1° C./min., with a final hold period of at least 1 h at −20° C. Solid-liquid separation was performed by filtration over vacuum suction, and the filtrated solid sample was dried under dynamic nitrogen purge overnight.

7.2 Compound 1 was dissolved in iso-butylalcohol at a concentration of approx. 40 mg/mL at 50° C. under stirring. The resulting clear solution was cooled to −20° C. at a cooling rate of 0.1° C./min., with a final hold period of at least 1 h at −20° C. Solid-liquid separation was performed by filtration over vacuum suction, and filtrated solid sample was dried under dynamic nitrogen purge overnight.

7.3 Compound 1 hydrate form H2 (the preparation of which is described below) was dispersed in 2-PrOH at a concentration level of 12% (m/m; relative to dry mass of Compound 1). The resulting dispersion was heated to 80° C. under stirring to obtain a clear solution. An initial cooling ramp from 80 to 70° C. was run at a rate of 0.5° C./min, with a subsequent hold time at 70° C. At 70° C., seed crystals of anhydrous Form A2 (ground particles<50 µm; approx. 4.5% rel. to quantity in reactor) were added. The seed crystals were pre-dispersed in approx. 1 mL 2-PrOH per 100 mg seed quantity. A hold time of 10 min was applied after seeding at 70° C. A cooling ramp from 70° C. to 5° C. was run at 0.1° C./min, followed by a hold time of 3 hours at the final end temperature (5° C.). Solid-liquid separation was performed by filtration over vacuum suction, and filtrated solid sample was dried under dynamic nitrogen purge at 70° C. overnight.

In an alternative method, Form A2 was prepared by slurry conversion from a different polymorphic form as follows:

7.4 Solid material, in particular a different polymorphic form of Compound 1, most preferably hydrate Form H2 (the preparation of which is described below), was dispersed in approx. 5.2 vol.-eq. ethylacetate and stirred at RT for 21 h. The precipitate was filtered off with suction and dried for at least 72 h at 60° C. under vacuum.

B. Solid Form A1 Preparation
Solid Form A1 of Compound 1 was Prepared by the Following Two Methods:

7.5 Approx. 50 mg of 8-(1,3-Dimethyl-1H-pyrazol-4-yl)-1-(3-fluoro-5-methoxy-pyridin-4-yl)-7-methoxy-3-methyl-1,3-dihydro-imidazo[4,5-c]quinolin-2-one (racemic mixture) were subject to SFC chiral separation, using a Lux Cellulose-2 column, and solvent mixture of CO$_2$/2-Propanol+0.5% DEA (75:25) at a flow rate of 5 mL/min. Obtained fraction was rinsed with dichloromethane, and concentrated at 30° C. bath temperature to obtain a solid.

7.6 Approx. 10 mg of 8-(1,3-Dimethyl-1H-pyrazol-4-yl)-1-(Sa)-(3-fluoro-5-methoxy-pyridin-4-yl)-7-methoxy-3- methyl-1,3-dihydro-imidazo[4,5-c]quinolin-2-one dissolved in 100 µL dichloromethane (DCM) were evaporated at RT (RT: room temperature, approx. 20-25° C.) to obtain a powder.

C. Solid Form A3 Preparation 7.7 Approx. 12 mg of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one solid material, representing an alternative morphic form other than A3, most preferably representing form A2, were dispersed in approx. 40 µL THF, and stirred at RT (20-25° C.) for approx. 4 weeks. The obtained solid was separated by centrifugation, and gently dried at ambient conditions to obtain a powder.

D. Solid Form NF9 Preparation:

Solid Form NF9 of Compound 1 was Prepared by the Following Two Methods:

7.8 Approx. 100 mg of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one, dissolved in 2000 µL dichloromethane, were rapidly flash-evaporated under vacuum at RT (approx. 20-25° C.) to obtain a powder.

7.9 Approx. 20 mg of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one, dissolved in 1000 µL acetone at 50° C., was added with 1 eq. benzoic acid. The solution was cooled down to RT (approx. 20-25° C.). The solution was then subject to vapor diffusion crystallization at RT (approx. 20-25° C.) using a reservoir of n-pentane, slowly diffusion into the solution via gas phase diffusion. After few days a solid crystallized, which was separated by centrifugation and gently dried under nitrogen purge to obtain a powder.

E. Solid Hydrate Form H1 Preparation

Solid Form H of Compound 1 Hydrate was Obtained by the Following Two Methods:

7.10 Approx. 12-13 mg of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one solid material, representing an alternative morphic form other than H1, most preferably form A2, were dispersed in approx. 200 µL methanol, and stirred at RT (20-25° C.) for 5 days. The obtained solid was separated by centrifugation, and gently dried at ambient conditions to obtain a powder.

7.11 Approx. 12 mg of 8-(1,3-Dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one, dissolved in 750 µL 1-propanol, were evaporated at RT (approx. 20-25° C.) to obtain a powder.

F. Solid Hydrate Form H2 Preparation 7.12 Approx. 19 g of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one solid material, representing an alternative morphic form other than H2, most preferably representing form A2, were dispersed in approx. 80 mL DI water, and stirred at RT (20-25° C.) for approx. 4 days. The obtained solid was separated by vacuum filtration, and dried at 50° C. under a nitrogen purge to obtain a powder.

7.13 Approx. 13-14 mg of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one, dissolved in 250 µL THF, were rapidly poured into a reservoir of 1500 µL DI water at RT (approx. 20-25° C.) under turbulent stirring. The obtained precipitate was separated by centrifugation, and gently dried at ambient conditions to obtain a powder.

G. Solid Form NF19 Preparation 7.14 Approx. 48 mg of 8-(1,3-dimethyl-1H-pyrazol-4-yl)-1-(Sa)-(3-fluoro-5-methoxy-pyridin-4-yl)-7-methoxy-3-methyl-1,3-dihydro-imidazo[4,5-c]quinolin-2-one, dissolved in 1500 µL methanol, were evaporated at 50° C. to obtain a powder.

Example 8: Combination with Radiotherapy

In an in vivo pharmacology study (FaDu SSCHN tumor model), combination treatment of concomitant Compound 1 and fractionated irradiation for 6 weeks (6×5 days, 2 Gy per fraction), strongly enhanced the efficacy of IR (irradiation) in a dose-dependent manner in line with the level of target engagement, as shown in FIG. 20. In detail:

The anti-tumor efficacy of the ATM inhibitor compound 1 was assessed in combination with irradiation (IR) in NMRI nu/nu mice bearing xenografts of the human squamous cell head and neck model FaDu.

One of the control groups was treated with vehicle only. The other control group was treated with IR only at 30 fractions IR of 2 Gy in a 5 days on/2 days off schedule and over a period of 6 weeks. Two groups were treated with the combination of IR (as in the IR only control) and compound 1 with an oral dose of 10 mg/kg, or 25 mg/kg 30 min prior to each IR fraction.

Example 9: Combination with PARP Inhibition

The efficacy of Compound 1 in combination with olaparib was demonstrated in a HBCx-10 patient-derived triple-negative breast cancer xenograft model, developed in immunodeficient female mice, results of which are shown in FIG. 21.

Seventy (70) mice with a subcutaneously growing HBCx-10 tumor (P20.1.4/0) between 62.5 and 196.0 mm³ were allocated to treatment when their mean and median tumor volume reached 131.16 and 126.00 mm³ respectively.

The study comprised various groups of 10 mice each:

In group 1, vehicle olaparib was administered at 10 ml/kg p.o. qd×28 combined with vehicle methocel administered at 10 ml/kg p.o. (3d on/4d off)×4;

In group 2, olaparib was dosed at 50 mg/kg p.o. qd×49;

In group 3, comparative ATM inhibitor ATMix alone was given p.o. (3d on/4d off)×5;

In group 4, olaparib was dosed at 50 mg/kg p.o. qd×49 combined with ATMix p.o. (3d on/4d off)×7;

In group 5, olaparib was dosed at 50 mg/kg p.o. qd×49 combined with Compound 1 at 100 mg/kg p.o. (3d on/4d off)×7.

Tumors were measured biweekly during the treatment period and once a week during the follow-up period.

p.o. perorally—d day—qd quaque die—one a day

The invention claimed is:

1. A compound, represented by the following formula

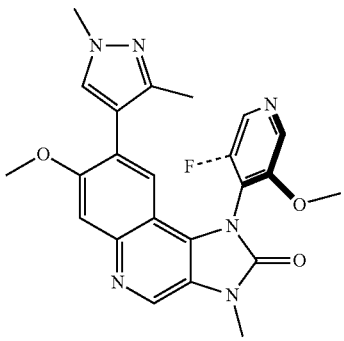

Compound 1 or pharmaceutically acceptable salt thereof.

2. A pharmaceutical composition, comprising: the compound or pharmaceutically acceptable salt thereof according to claim 1, and a pharmaceutically acceptable excipient.

3. Compound 1 according to claim 1.

4. A pharmaceutically acceptable salt of Compound 1 according to claim 1, wherein the pharmaceutically acceptable salt of Compound 1 is selected from the group consisting of Compound 1 fumarate, Compound 1 napsylate, and Compound 1 edisylate.

5. A solid anhydrous form of Compound 1 according to claim 1.

6. The solid anhydrous form of Compound 1 according to claim 5, wherein one or more peaks in a powder X-ray diffraction pattern is selected from those at about 7.3, about 9.6, about 11.1, about 12.0, about 12.7, and about 16.2 degrees 2-theta ±0.2 degrees 2-theta.

7. The solid anhydrous form of Compound 1 according to claim 5, wherein the solid anhydrous form of Compound 1 has a monoclinic crystal system and a $P2_1$ space group and/or the following parameters of its unit cell:

| | | | |
|---|---|---|---|
| a | 7.457 Å | α | 90.0° |
| b | 15.982 Å | β | 90.0° |
| c | 18.246 Å | γ | 90.0° |
| V | 2174.5 Å$^3$. | | |

8. A pharmaceutical composition, comprising:
the solid anhydrous form of Compound 1 according to claim 5, and a pharmaceutically acceptable excipient.

* * * * *